United States Patent
Rathod et al.

(10) Patent No.: US 9,238,653 B2
(45) Date of Patent: *Jan. 19, 2016

(54) ANTIMALARIAL AGENTS THAT ARE INHIBITORS OF DIHYDROOROTATE DEHYDROGENASE

(75) Inventors: Pradipsinh K. Rathod, Seattle, WA (US); David Floyd, Pennington, NJ (US); Jeremy Burrows, Geneva (CH); Alka Marwaha, Seattle, WA (US); Ramesh Gujjar, Seattle, WA (US); Jose Coteron-Lopez, Madrid (ES); Margaret Phillips, Dallas, TX (US); Susan A. Charman, Victoria (AU); David Matthews, Encinitas (CA)

(73) Assignees: BOARD OF REGENTS, THE UNIVERSITY OF TEXAS SYSTEM, Austin, TX (US); MMV MEDICINES FOR MALARIA VENTURE, Geneva (CH); UNIVERSITY OF WASHINGTON, Seattle, WA (US)

( * ) Notice: Subject to any disclaimer, the term of this patent is extended or adjusted under 35 U.S.C. 154(b) by 478 days.

This patent is subject to a terminal disclaimer.

(21) Appl. No.: 13/499,031

(22) PCT Filed: Sep. 28, 2010

(86) PCT No.: PCT/US2010/050532
§ 371 (c)(1),
(2), (4) Date: Aug. 10, 2012

(87) PCT Pub. No.: WO2011/041304
PCT Pub. Date: Apr. 7, 2011

(65) Prior Publication Data
US 2012/0302586 A1 Nov. 29, 2012

Related U.S. Application Data

(60) Provisional application No. 61/246,863, filed on Sep. 29, 2009.

(51) Int. Cl.
C07D 487/04 (2006.01)
A61K 31/519 (2006.01)
A61P 33/06 (2006.01)

(52) U.S. Cl.
CPC .................... C07D 487/04 (2013.01)

(58) Field of Classification Search
CPC ............................ C07D 487/04; A61K 31/519
USPC ............................ 544/281; 514/259.1, 259.3
See application file for complete search history.

(56) References Cited

U.S. PATENT DOCUMENTS

| 5,478,825 A | 12/1995 | Reiter et al. |
| 2008/0027079 A1 | 1/2008 | Phillips et al. |
| 2009/0209557 A1 | 8/2009 | Phillips et al. |

FOREIGN PATENT DOCUMENTS

| JP | 05148267 | 6/1993 |
| WO | WO 2007/149211 | 12/2007 |
| WO | WO 2009/082691 | 7/2009 |

OTHER PUBLICATIONS

Phillips, M. et al. "Triazolopyrimidine-Based Dihydroorotate Dehydrogenase Inhibitors with Potent and Selective Activity against the Malaria Parasite *Plasmodium falciparum*" *Journal of Medicinal Chemistry*, Jun. 2008, pp. 3649-3653, vol. 51, No. 12.

Gujjar, R. et al. "Lead Optimization of Aryl and Aralkyl Amine-Based Triazolopyrimidine Inhibitors of *Plasmodium falciparum* Dihydroorotate Dehydrogenase with Antimalarial Activity in Mice" *Journal of Medicinal Chemistry*, 2011, pp. 3935-3949, vol. 54.

Deng, X. et al. "Structural Plasticity of Malaria Dihydroorotate Dehydrogenase Allows Selective Binding of Diverse Chemical Scaffolds" *Journal of Biological Chemistry*, Sep. 25, 2009, pp. 26999-27009, vol. 284, No. 39.

(Continued)

*Primary Examiner* — Susanna Moore
(74) *Attorney, Agent, or Firm* — Saliwanchik, Lloyd & Eisenschenk

(57) ABSTRACT

Inhibitors of parasitic dihydroorotate dehydrogenase enzyme (DHOD) are candidate therapeutics for treating malaria. Illustrative of such therapeutic agents include the compound:

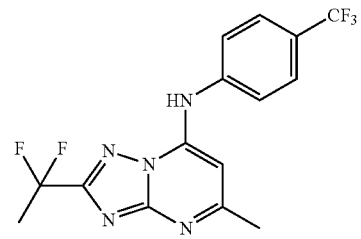

and a triazolopyrimidine class of compounds that conform to Formula IX:

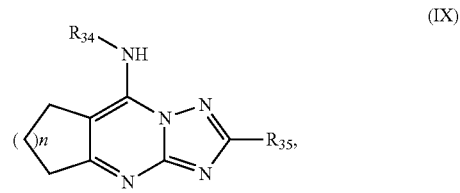

and their solvates, stereoisomers, tautomers and pharmaceutically acceptable salts.

19 Claims, No Drawings

(56) References Cited

OTHER PUBLICATIONS

Gujjar, R. et al. "Identification of a Metabolically Stable Triazolopyrimidine-Based Dihydroorotate Dehydrogenase Inhibitor with Antimalarial Activity in Mice" *Journal of Medicinal Chemistry*, 2009, pp. 1864-1872, vol. 52, No. 7.

Guiguemde, W. A. et al. "Chemical genetics of *Plasmodium falciparum*" *Nature*, May 20, 2010, pp. 311-315, vol. 465.

Coteron, J. et al. "Structure-Guided Lead Optimization of Triazolopyrimidine-Ring Substituents Identifies Potent *Plasmodium falciparum* Dihydroorotate Dehydrogenase Inhibitors with Clinical Candidate Potential" *Journal of Medicinal Chemistry*, 2011, pp. 5540-5561, vol. 54.

Ojha, P. et al. "Chemometric modeling, docking and in silico design of triazolopyrimidine-based dihydroorotate dehydrogenase inhibitors as antimalarials" *European Journal of Medicinal Chemistry*, 2010, pp. 4645-4656, vol. 45.

Gamo, F.-J. et al. "Thousands of chemical starting points for antimalarial lead identification" *Nature*, May 20, 2010, pp. 305-310, vol. 465.

Baldwin, J. et al. "High-throughput Screening for Potent and Selective Inhibitors of *Plasmodium falciparum* Dihydroorotate Dehydrogenase" *The Journal of Biological Chemistry*, Jun. 10, 2005, pp. 21847-21853, vol. 280, No. 23.

Written Opinion in International Application No. PCT/US2010/050532, Jun. 16, 2011, pp. 1-4.

Marwaha, A. et al. "Bioisosteric Transformations and Permutations in the Triazolopyrimidine Scaffold to Identify the Minimum Pharmacophore Required for Inhibitory Activity against *Plasmodium falciparum* Dihydroorotate Dehydrogenase" *Journal of Medicinal Chemistry*, 2012, pp. 7425-7436, vol. 55.

Deng, X. et al. "Fluorine Modulates Species Selectivity in the Triazolopyrimidine Class of *Plasmodium falciparum* Dihydroorotate Dehydrogenase Inhibitors" *Journal of Medicinal Chemistry*, 2014, pp. 1-14.

CAS registry No. RN: 951587-53-4 (2007), 946359-78-0 (2007), 933200-74-9 (2007), 900886-29-5 (2006), 900296-94-8 (2006), 890622-16-9 (2006), pp. 1-9.

ANTIMALARIAL AGENTS THAT ARE INHIBITORS OF DIHYDROOROTATE DEHYDROGENASE

CROSS-REFERENCE TO RELATED APPLICATIONS

This application is the U.S. national stage application of International Patent Application No. PCT/US2010/050532, filed Sep. 28, 2010, which claims the benefit of U.S. Provisional Patent Application No. 61/246,863, filed Sep. 29, 2009.

GOVERNMENT RIGHTS

This invention was funded by NIH R01 AI053680 and NIH UO1 AI075594. The U.S. Government has certain rights in this invention.

The invention claimed in this application arose as a result of activities undertaken within the scope of a joint research agreement and was made by or behalf of parties to a joint research agreement in effect on, or before, the date the claimed invention was made. The parties to the joint research agreement were Board of Regents, University of Texas System, University of Washington, Medicines for Malaria Venture and Monash University.

BACKGROUND OF THE INVENTION

The present invention relates to novel anti-malarial agents and inhibitors of dihydroorotate dehydrogenase.

Malaria is a disease that is prevalent in many developing countries. Nearly 40% of the world's population is at risk for contracting this disease, which has been a major cause of mortality throughout history. In the United States travelers to these endemic regions are at risk for contracting the disease. The widespread emergence of drug resistance in many tropical countries has compromised many of the current chemotherapies and there is a continued need for new chemotherapeutic approaches.

Malaria is a disease caused by a parasite transmitted by the bite of an infected female *Anopheles* mosquito. When an infecting sporozoite parasite enters the bloodstream it rapidly infects both liver and red blood cells and differentiates into merozoites. Asexual reproduction of the merozoite within erythrocytes results in the rupture and subsequent reinfection of other red blood cells. This cyclic process results in clinical symptoms, which include headaches, sweating, vomiting, malaise, delirium and acute fever and may be fatal if not treated. Malaria in humans is caused by 4 species of parasitic protozoa belonging to the genus *Plasmodium*. Of these, *P. falciparum* is the most deadly and the greatest threat to travelers abroad while *P. malariae, P. vivax* and *P. ovale*, though infrequently fatal in healthy adults, can cause morbidity in the endemic areas.

Various medications are presently used for the treatment of malaria. However, many of these medications are costly and some exhibit significant toxicity and undesirable side effects in humans. The most common drug for treating malaria is chloroquine. Other drugs include quinine, mefloquine, atovaquone/proguanil, doxycycline, artesunate, hydroxychloroquine, halofantrine, pyrimethamine-sulfadoxine, and primaquine. Drug choice often depends on one of the four types of malaria parasites.

Malaria parasites rely on de novo pyrimidine biosynthesis to provide precursors for DNA and RNA synthesis, hence for proliferation. The parasite does not have pyrimidine nucleoside or base salvage pathways, thus the enzymes in the de novo pathway are essential to parasite survival. In contrast, mammalian cells have salvage pathways that provide an alternative route to these essential metabolites.

Dihydroorotate dehydrogenase (DHODH) is an essential enzyme of the pyrimidine salvage pathway, and a number of lines of evidence suggest that it is an important target for the development of new chemotherapy against malaria. DHODH is a flavin-dependent mitochondrial enzyme that catalyzes the fourth reaction in the salvage pathway; coenzyme Q is utilized as the oxidant. The enzyme has a number of properties that make it a particularly strong candidate as a new drug target in the parasite Inhibitors of human DHODH have proven efficacy for the treatment of rheumatoid arthritis demonstrating that the target pathway can be effectively blocked in vivo. The X-ray structures of DHODH reveal that the inhibitor binding pocket of the enzyme is highly variable between species, providing a structural basis for the design of species-specific inhibitors.

A need exists for a method of treating malaria. There is also a need for an anti-malarial agent to overcome current drug resistance problems with existing therapy. Further, anti-malarial agents are needed that selectively inhibit malarial DHODH but exhibit no substantial toxicity against mammalian, especially human DHODH.

Accordingly, this invention provides novel potent anti-malarial agents and methodology of treating malaria using novel potent anti-malarial agents. The invention also provides potent anti-malarial agents that are selective inhibitors of *P. falciparum* dihydroorotate dehydrogenase and active against chloroquine-sensitive and resistant malarial strains.

SUMMARY OF THE INVENTION

The present invention relates to novel compounds for inhibiting the activity of *Plasmodium falciparum* dihydroorotate dehydrogenase. The compounds display selective inhibition of *Plasmodium falciparum* dihydroorotate dehydrogenase over human dihydroorotate dehydrogenase.

The present invention also relates to methods for preventing or treating diseases associated with the action of *Plasmodium falciparum* dihydroorotate dehydrogenase, such as malaria.

One embodiment of the invention provides a compound that is selected from the following table:

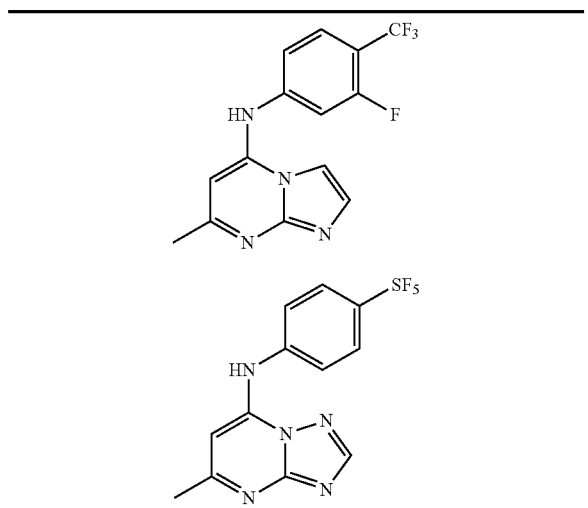

| 3 -continued | | 4 -continued | |
|---|---|---|---|
| 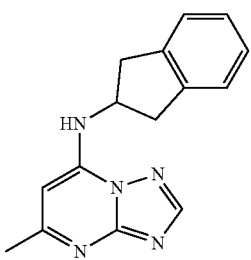 [SMILES: Cc1cc(NC2Cc3ccccc3C2)n2ncnc2n1] | | 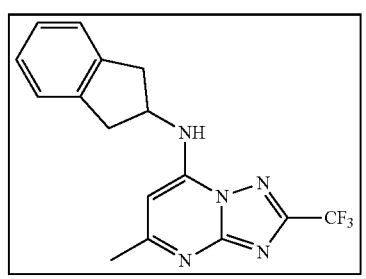 | |
| 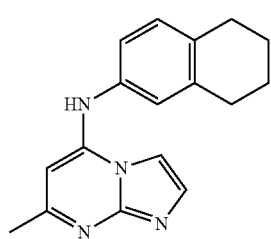 [SMILES: Cc1cc(Nc2ccc3c(c2)CCCC3)n2ccnc2n1] | | 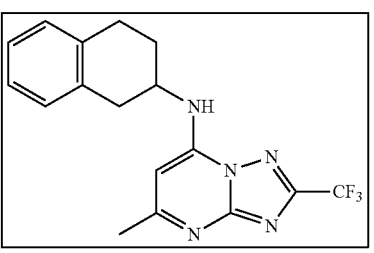 | |
| 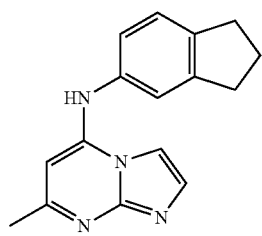 [SMILES: Cc1cc(Nc2ccc3c(c2)CCC3)n2ccnc2n1] | | 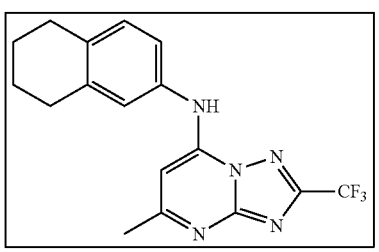 | |
| 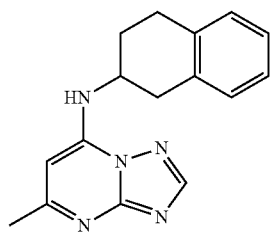 [SMILES: Cc1cc(NC2CCc3ccccc3C2)n2ncnc2n1] | | 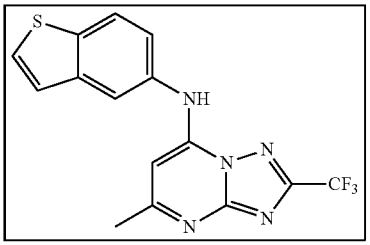 | |
| 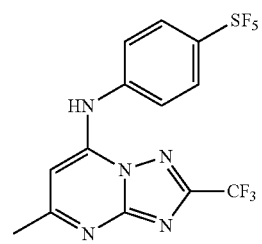 | | 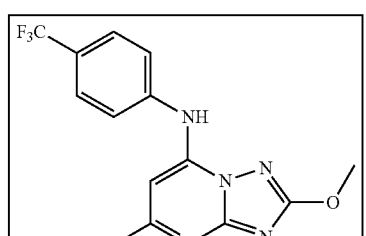 | |
| 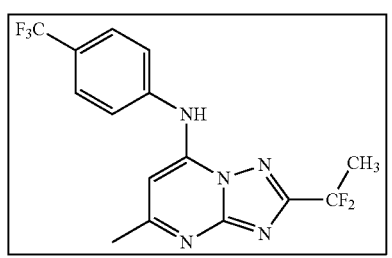 [SMILES: Cc1cc(Nc2ccc(C(F)(F)F)cc2)n2nc(C(C)(F)F)nc2n1] | | 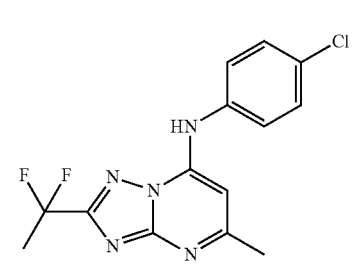 [SMILES: Cc1cc(Nc2ccc(Cl)cc2)n2nc(C(C)(F)F)nc2n1] | |

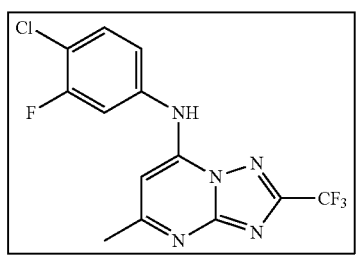 [SMILES: Cc1cc(Nc2ccc(Cl)c(F)c2)n2nc(C(F)(F)F)nc2n1]
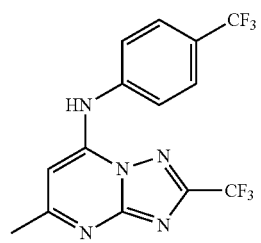 [SMILES: Cc1cc(Nc2ccc(C(F)(F)F)cc2)n2nc(C(F)(F)F)nc2n1]
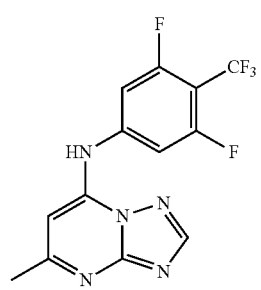 [SMILES: Cc1cc(Nc2cc(F)c(C(F)(F)F)c(F)c2)n2ncnc2n1]
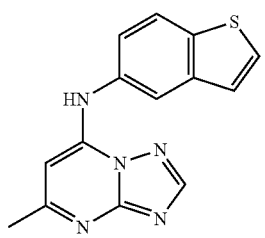 [SMILES: Cc1cc(Nc2ccc3sccc3c2)n2ncnc2n1]
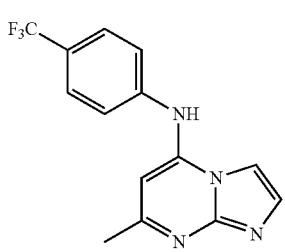
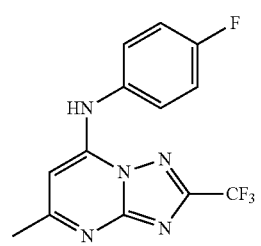 [SMILES: Cc1cc(Nc2ccc(F)cc2)n2nc(C(F)(F)F)nc2n1]
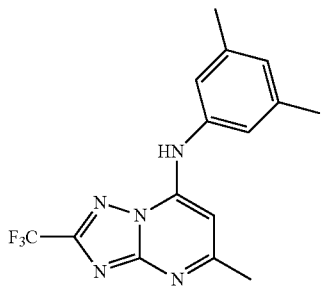 [SMILES: Cc1cc(C)cc(Nc2cc(C)nc3nc(C(F)(F)F)nn23)c1]
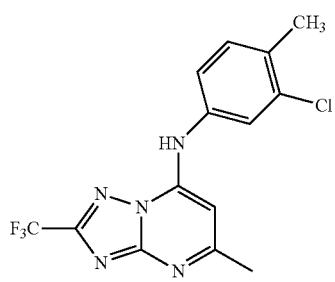 [SMILES: Cc1cc(Nc2ccc(C)c(Cl)c2)n2nc(C(F)(F)F)nc2n1]
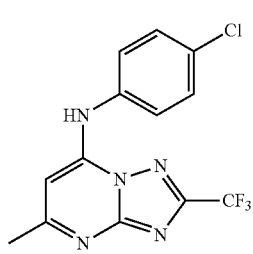
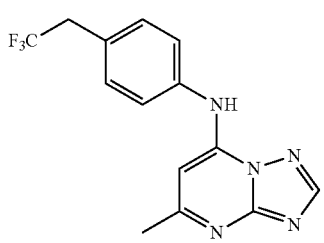 [SMILES: Cc1cc(Nc2ccc(CC(F)(F)F)cc2)n2ncnc2n1]
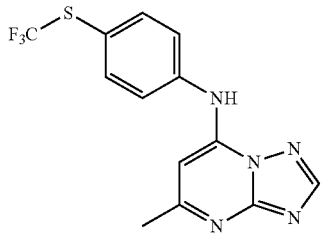 [SMILES: Cc1cc(Nc2ccc(SC(F)(F)F)cc2)n2ncnc2n1]
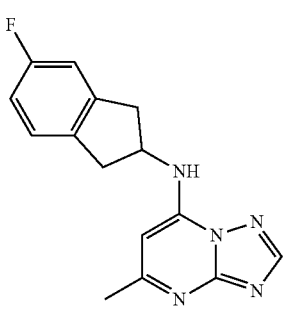 [SMILES: Cc1cc(NC2Cc3ccc(F)cc3C2)n2ncnc2n1]

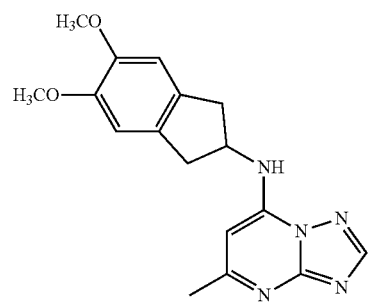 [SMILES: COc1cc2c(cc1OC)CC(Nc1cc(C)nc3ncnn13)C2]
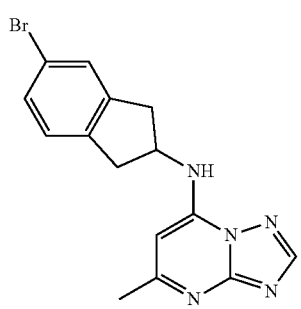 [SMILES: Cc1cc(NC2Cc3ccc(Br)cc3C2)n2ncnc2n1]
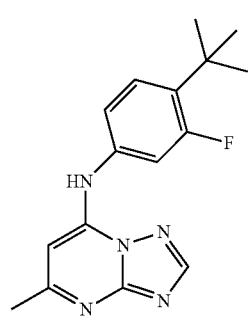 [SMILES: Cc1cc(Nc2ccc(C(C)(C)C)c(F)c2)n2ncnc2n1]
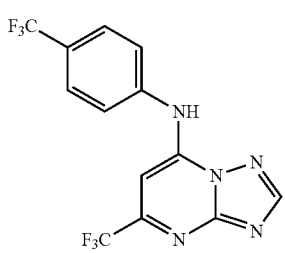
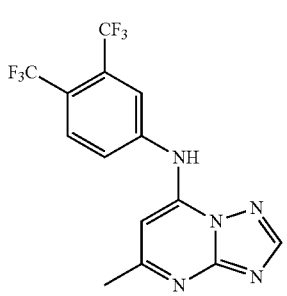 [SMILES: Cc1cc(Nc2ccc(C(F)(F)F)c(C(F)(F)F)c2)n2ncnc2n1]
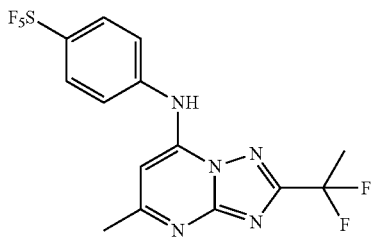
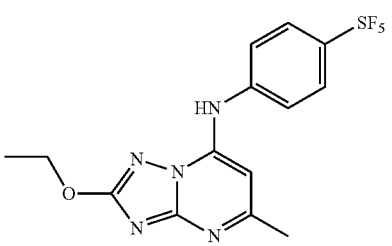
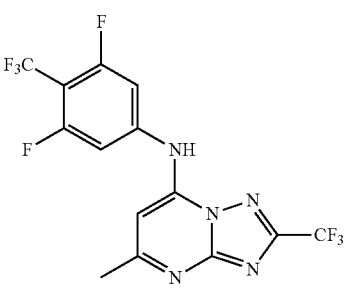 [SMILES: Cc1cc(Nc2cc(F)c(C(F)(F)F)c(F)c2)n2nc(C(F)(F)F)nc2n1]
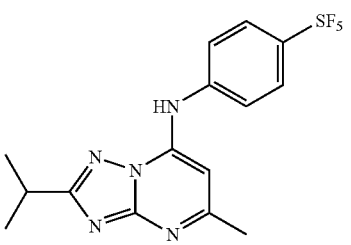
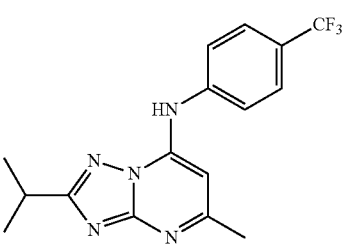

-continued
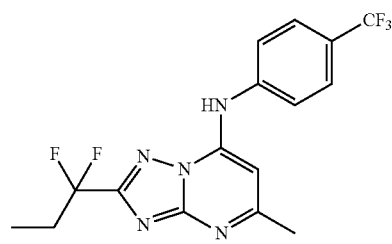
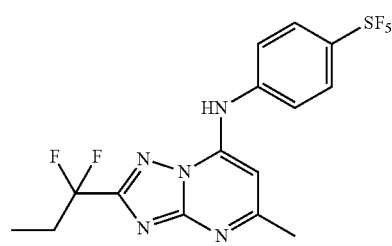 [SMILES: CCC(F)(F)c1nc2nc(C)cc(Nc3ccc(C(F)(F)F)cc3)n2n1]
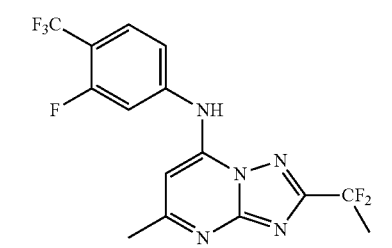 [SMILES: Cc1cc(Nc2ccc(C(F)(F)F)c(F)c2)n2nc(C(C)(F)F)nc2n1]
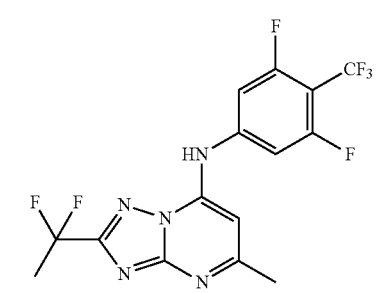 [SMILES: Cc1cc(Nc2cc(F)c(C(F)(F)F)c(F)c2)n2nc(C(C)(F)F)nc2n1]
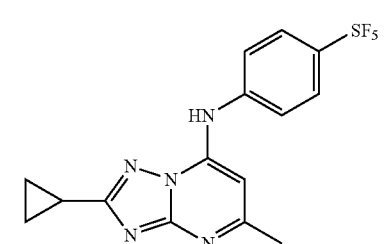
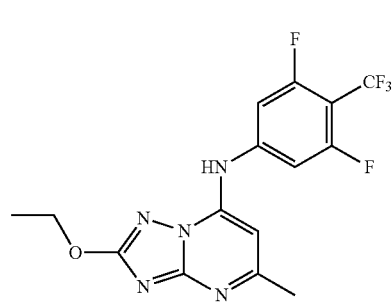 [SMILES: CCOc1nc2nc(C)cc(Nc3cc(F)c(C(F)(F)F)c(F)c3)n2n1]
-continued
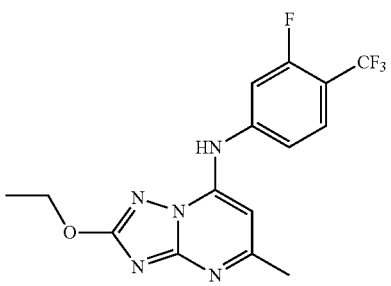 [SMILES: CCOc1nc2nc(C)cc(Nc3ccc(C(F)(F)F)c(F)c3)n2n1]
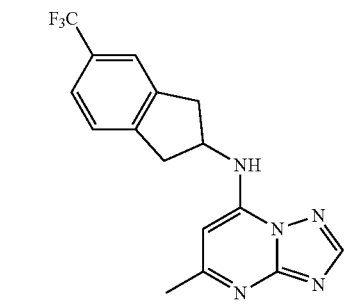 [SMILES: Cc1cc(NC2Cc3ccc(C(F)(F)F)cc3C2)n2ncnc2n1]
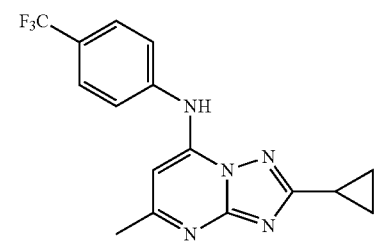
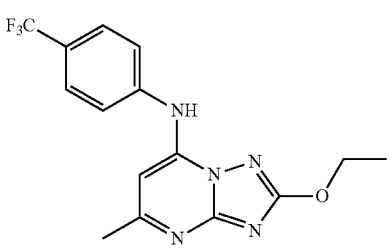
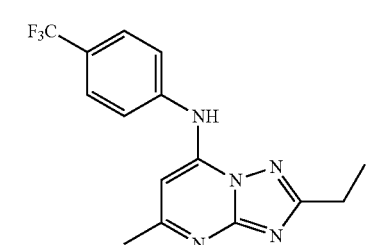
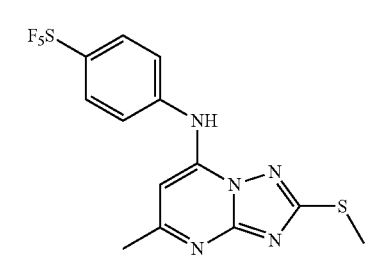

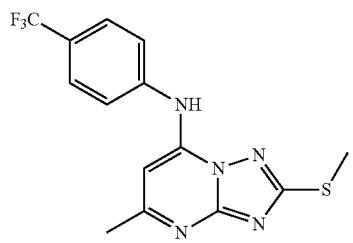
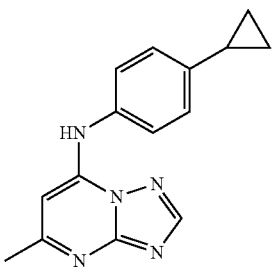 [SMILES: Cc1cc(Nc2ccc(C3CC3)cc2)n2ncnc2n1]
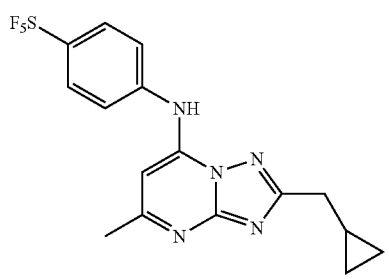
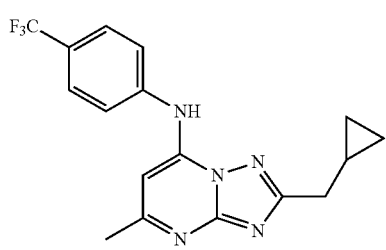 [SMILES: Cc1cc(Nc2ccc(C(F)(F)F)cc2)n2nc(CC3CC3)nc2n1]
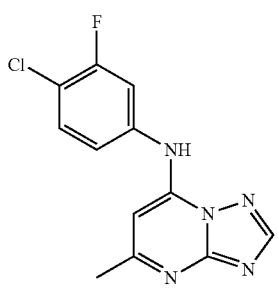 [SMILES: Cc1cc(Nc2ccc(Cl)c(F)c2)n2ncnc2n1]
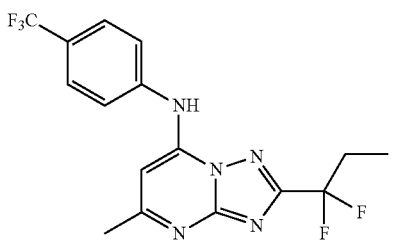 [SMILES: CCC(F)(F)c1nc2nc(C)cc(Nc3ccc(C(F)(F)F)cc3)n2n1]
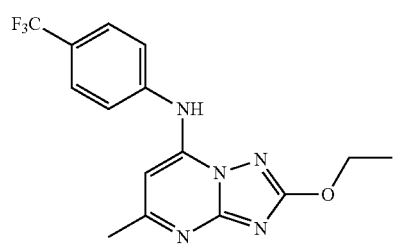 [SMILES: CCOc1nc2nc(C)cc(Nc3ccc(C(F)(F)F)cc3)n2n1]
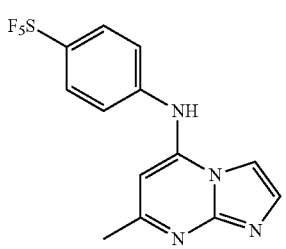
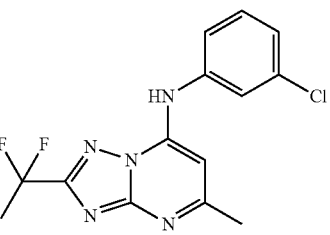
The invention also encompasses pharmaceutically acceptable salts, solvates, stereoisomers, tautomers, and prodrugs of such compounds.
In another embodiment invention provides a pharmaceutical composition that comprises a compound that is selected from the following table:
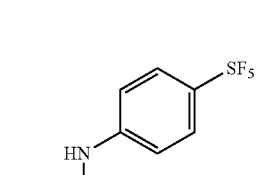
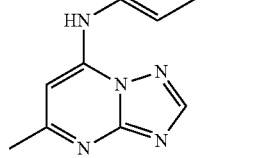

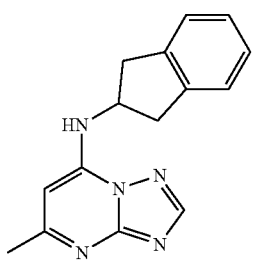 [SMILES: Cc1cc(NC2Cc3ccccc3C2)n2ncnc2n1]
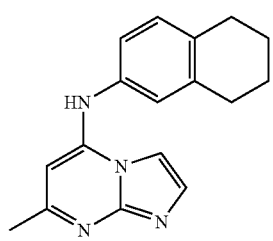 [SMILES: Cc1cc(Nc2ccc3c(c2)CCCC3)n2ccnc2n1]
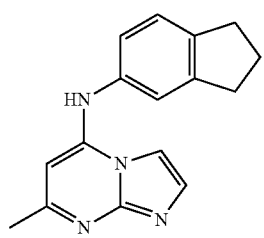 [SMILES: Cc1cc(Nc2ccc3c(c2)CCC3)n2ccnc2n1]
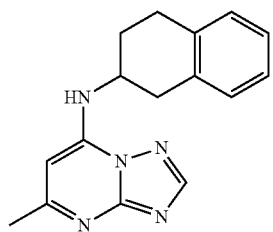 [SMILES: Cc1cc(NC2CCc3ccccc3C2)n2ncnc2n1]
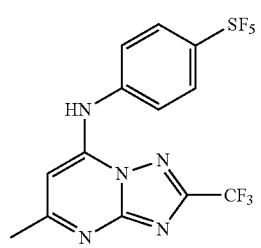
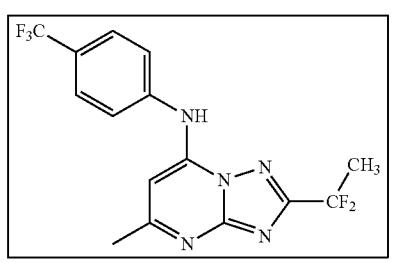 [SMILES: Cc1cc(Nc2ccc(C(F)(F)F)cc2)n2nc(C(C)(F)F)nc2n1]
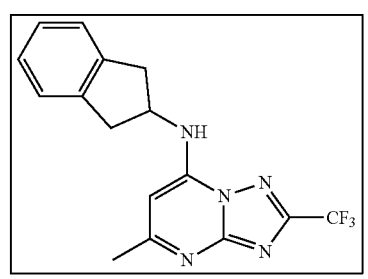 [SMILES: Cc1cc(NC2Cc3ccccc3C2)n2nc(C(F)(F)F)nc2n1]
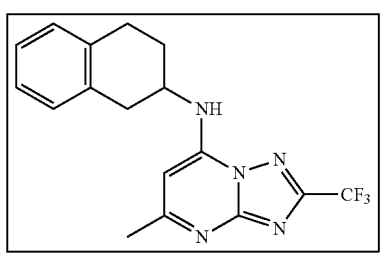 [SMILES: Cc1cc(NC2CCc3ccccc3C2)n2nc(C(F)(F)F)nc2n1]
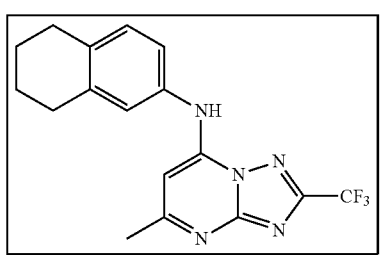 [SMILES: Cc1cc(Nc2ccc3c(c2)CCCC3)n2nc(C(F)(F)F)nc2n1]
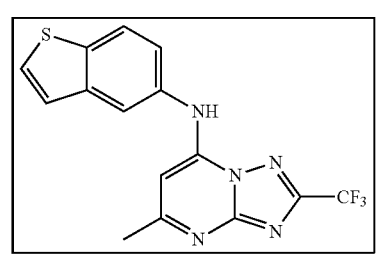 [SMILES: Cc1cc(Nc2ccc3sccc3c2)n2nc(C(F)(F)F)nc2n1]
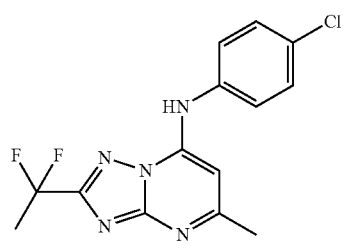 [SMILES: Cc1cc(Nc2ccc(Cl)cc2)n2nc(C(C)(F)F)nc2n1]
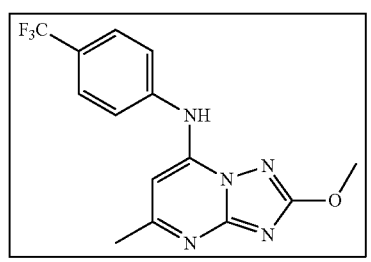 [SMILES: COc1nc2nc(C)cc(Nc3ccc(C(F)(F)F)cc3)n2n1]

-continued
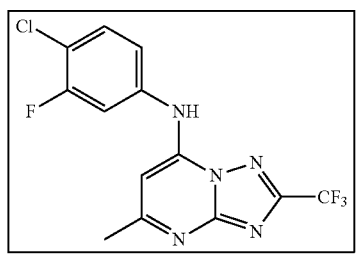 [SMILES: Cc1cc(Nc2ccc(Cl)c(F)c2)n2nc(C(F)(F)F)nc2n1]
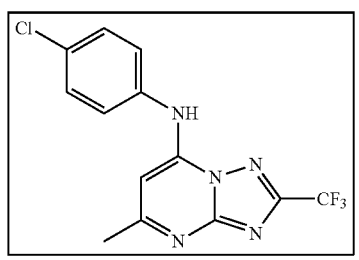 [SMILES: Cc1cc(Nc2ccc(Cl)cc2)n2nc(C(F)(F)F)nc2n1]
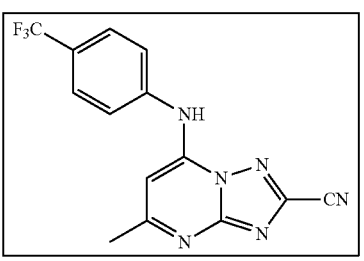 [SMILES: Cc1cc(Nc2ccc(C(F)(F)F)cc2)n2nc(C#N)nc2n1]
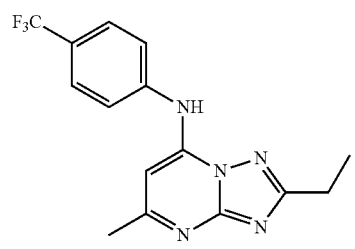
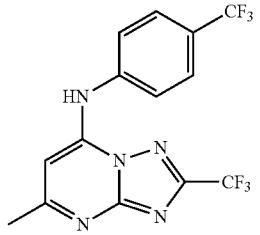 [SMILES: Cc1cc(Nc2ccc(C(F)(F)F)cc2)n2nc(C(F)(F)F)nc2n1]
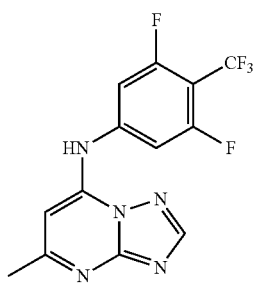 [SMILES: Cc1cc(Nc2cc(F)c(C(F)(F)F)c(F)c2)n2ncnc2n1]
-continued
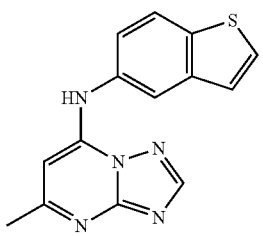 [SMILES: Cc1cc(Nc2ccc3sccc3c2)n2ncnc2n1]
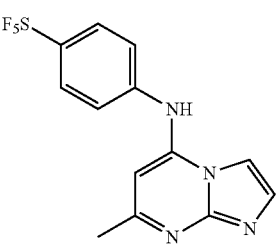
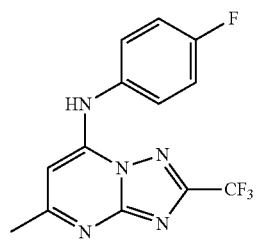 [SMILES: Cc1cc(Nc2ccc(F)cc2)n2nc(C(F)(F)F)nc2n1]
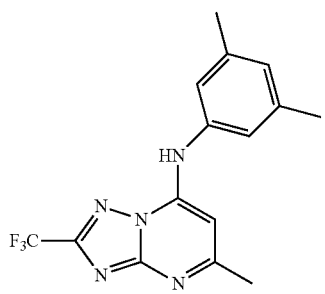 [SMILES: Cc1cc(C)cc(Nc2cc(C)nc3nc(C(F)(F)F)nn23)c1]
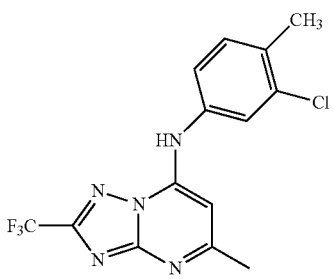 [SMILES: Cc1cc(Nc2ccc(C)c(Cl)c2)n2nc(C(F)(F)F)nc2n1]
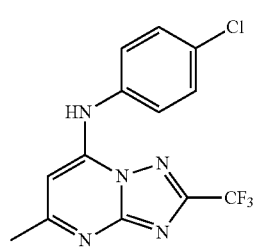

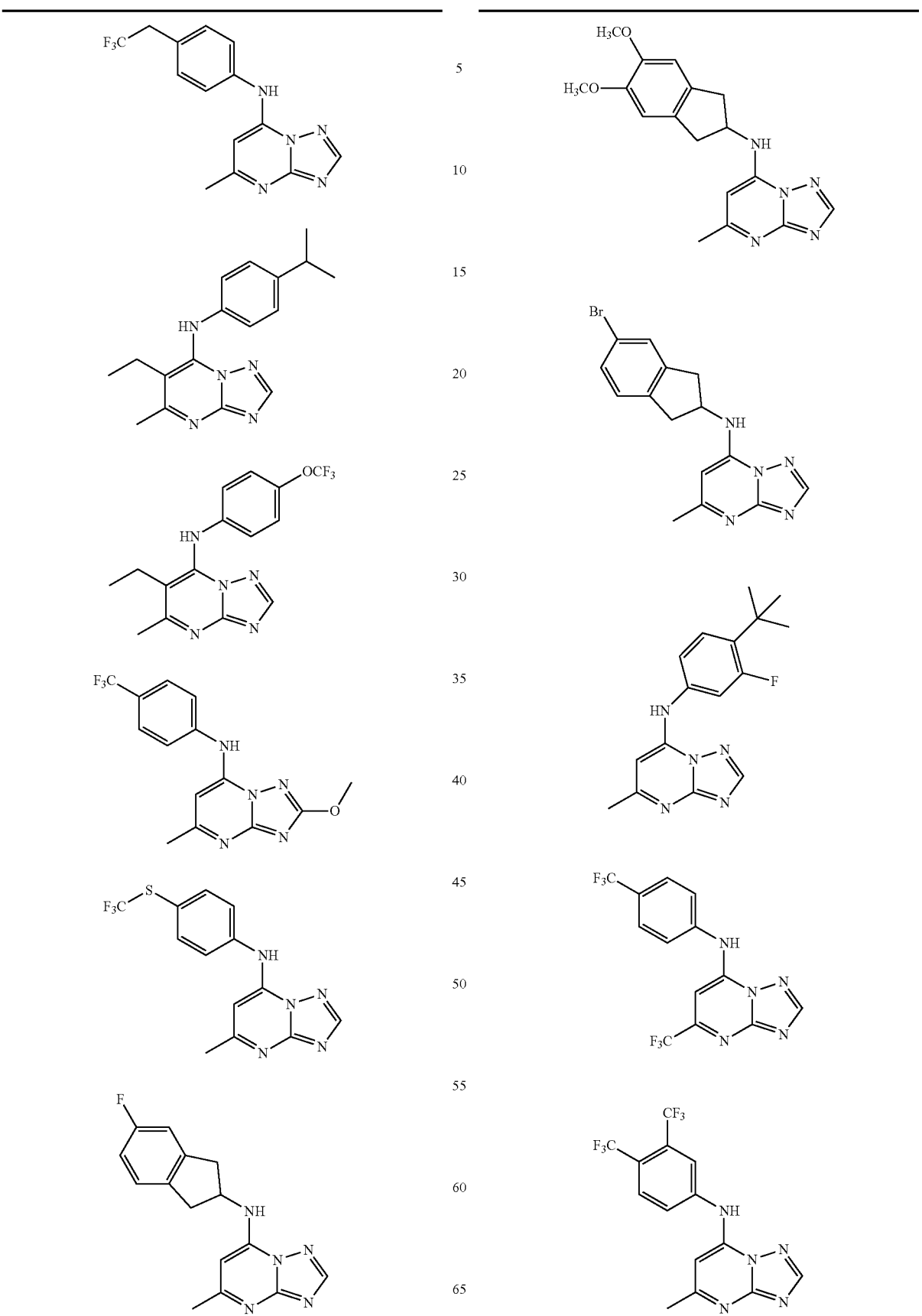

19
-continued
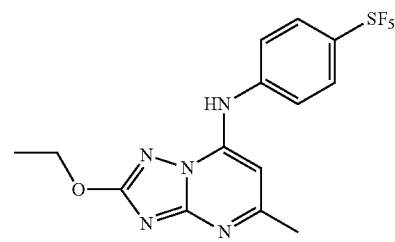
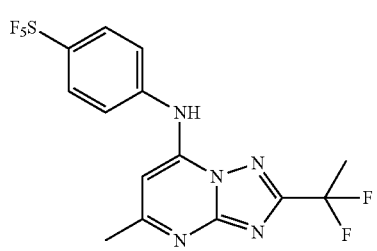
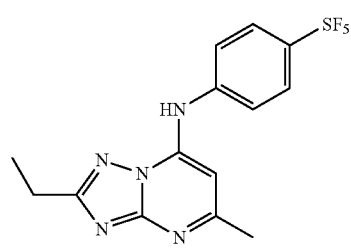
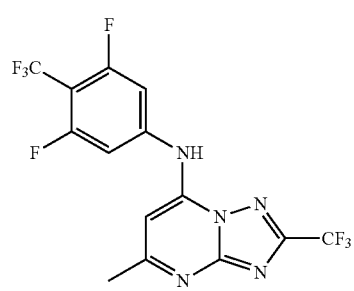 [SMILES: Cc1cc(Nc2cc(F)c(C(F)(F)F)c(F)c2)n2nc(C(F)(F)F)nc2n1]
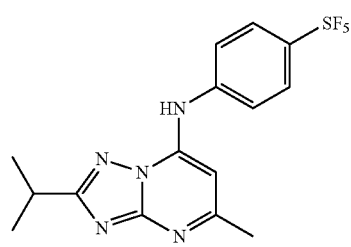
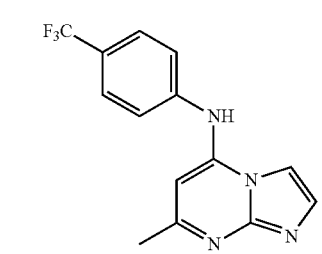
20
-continued
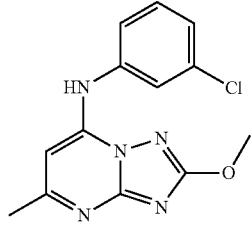
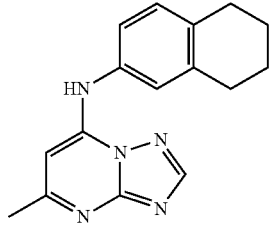 [SMILES: Cc1cc(Nc2ccc3c(c2)CCCC3)n2ncnc2n1]
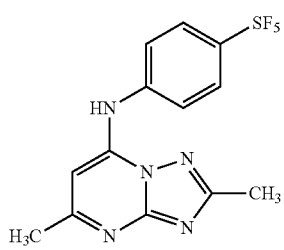
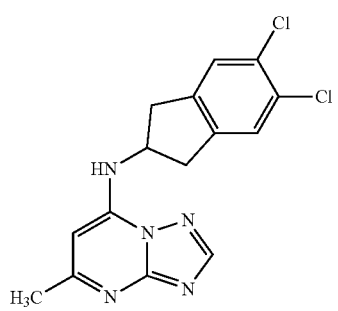 [SMILES: Cc1cc(NC2Cc3cc(Cl)c(Cl)cc3C2)n2ncnc2n1]
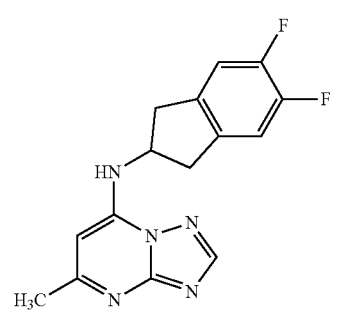 [SMILES: Cc1cc(NC2Cc3cc(F)c(F)cc3C2)n2ncnc2n1]
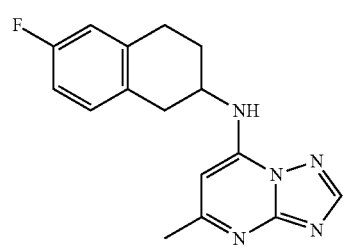 [SMILES: Cc1cc(NC2CCc3cc(F)ccc3C2)n2ncnc2n1]

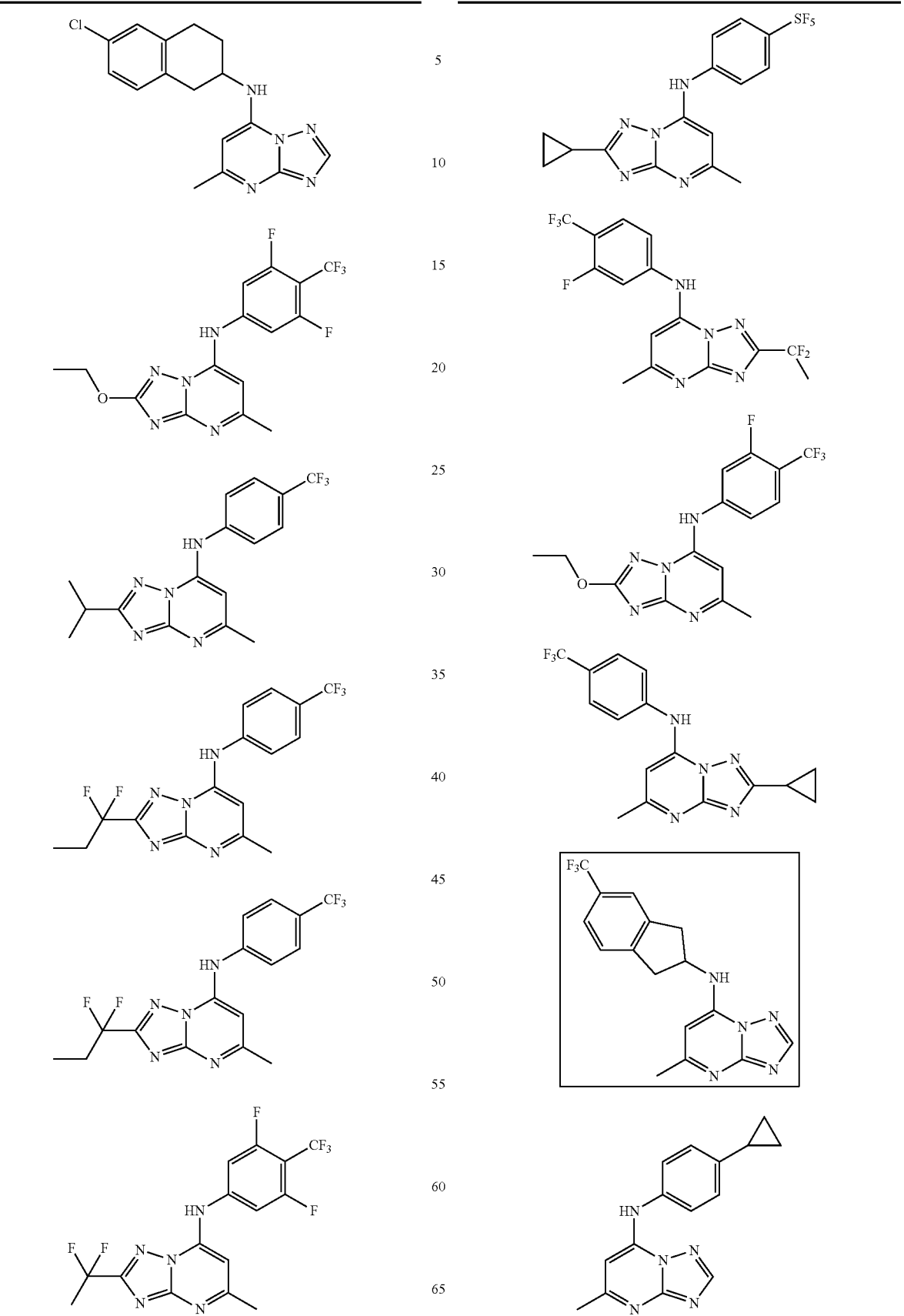

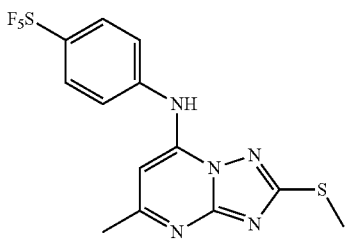

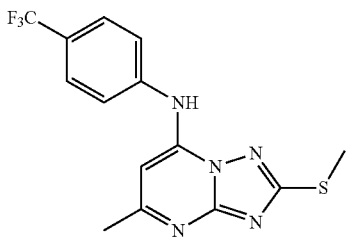

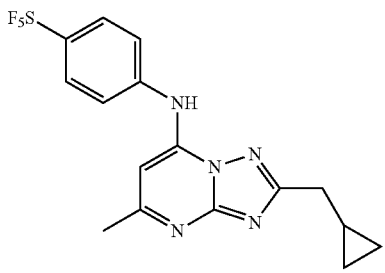

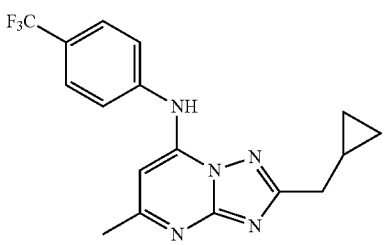 [SMILES: Cc1cc(Nc2ccc(C(F)(F)F)cc2)n2nc(CC3CC3)nc2n1]

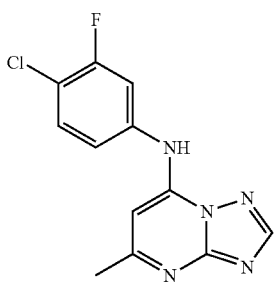 [SMILES: Cc1cc(Nc2ccc(Cl)c(F)c2)n2ncnc2n1]

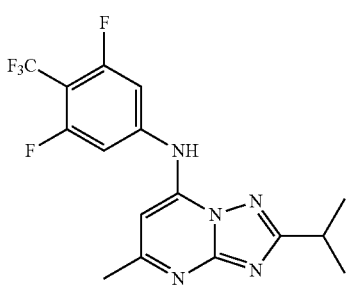 [SMILES: Cc1cc(Nc2cc(F)c(C(F)(F)F)c(F)c2)n2nc(C(C)C)nc2n1]

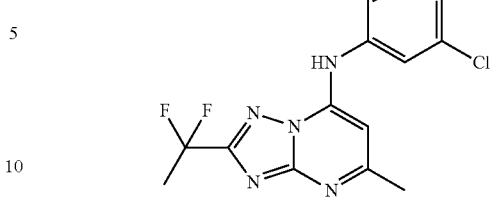

and stereoisomers, tautomers, solvates and pharmaceutically acceptable salts of these compounds and a pharmaceutically acceptable carrier.

In accordance with an embodiment of the invention, compounds are provided that conform to Formula IX:

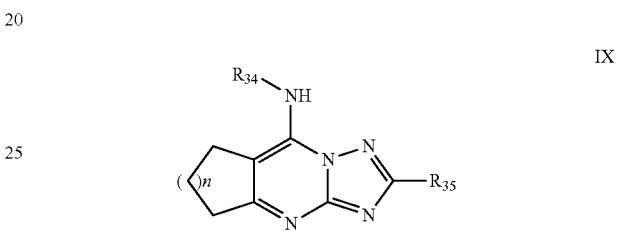

In formula IX, $R^{34}$ is selected from the group consisting of phenyl, aryl, 6- to 14-membered heterocycloalkyl, 6- to 14-membered arylcycloalkylene, 6- to 14-membered cycloalkylarylene, 3- to 8-membered cycloalkyl and 6- to 14-membered heteroaryl.

When $R^{34}$ is a phenyl, an aryl, a heterocycloalkyl, an arylcycloalkylene, a cycloalkylarylene, or a heteroaryl group, $R^{34}$ is optionally substituted with one or more members selected from the group consisting of F, I, Br, Cl, CN, $NO_2$, $-NR^aR^b$, $(C_1-C_8)$haloalkyl, $(C_1-C_8)$haloalkoxy, $(C_1-C_8)$alkoxy, oxaaryl, $(C_1-C_8)$alkyl, $(C_1-C_8)$-alkylarylene, $(C_2-C_8)$alkenyl, $(C_2-C_8)$alkynyl, $(C_3-C_8)$aryl$(C_1-C_8)$alkylene, and aryl.

Substituent $R^{35}$ is selected from the group consisting of hydrogen, halogen, $(C_1-C_8)$alkyl, $(C_2-C_8)$alkenyl, $(C_2-C_8)$alkynyl, $(C_1-C_8)$alkoxy, and $(C_1-C_8)$haloalkyl, phenyl, $(C_3-C_8)$cycloalkyl, $(C_3-C_8)$heteroaryl, $(C_3-C_8)$heterocycloalkyl, $(C_3-C_8)$aryl$(C_1-C_8)$alkylene, and $(C_3-C_8)$cycloalkyl$(C_1-C_8)$alkylene. Additionally, the cycloalkyl ring can be either 5- 6- or 7-membered, depending on the integer value of "n". In one embodiment n is an integer from 0 to 2.

Substituents $R^a$ and $R^b$ are independently selected from the group H, $(C_1-C_8)$alkyl, aryl, heteroaryl, heterocycloalkyl, $(C_1-C_8)$haloalkoxy, $(C_1-C_8)$haloalkyl, $(C_3-C_8)$cycloalkyl and $(C_1-C_6)$hydroxyalkyl.

For inventive compounds according to formula IX that have a $-CO_2H$ substituent, the $-CO_2H$ group can be replaced with bioisosteric replacements such as:

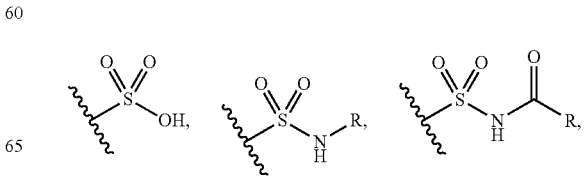

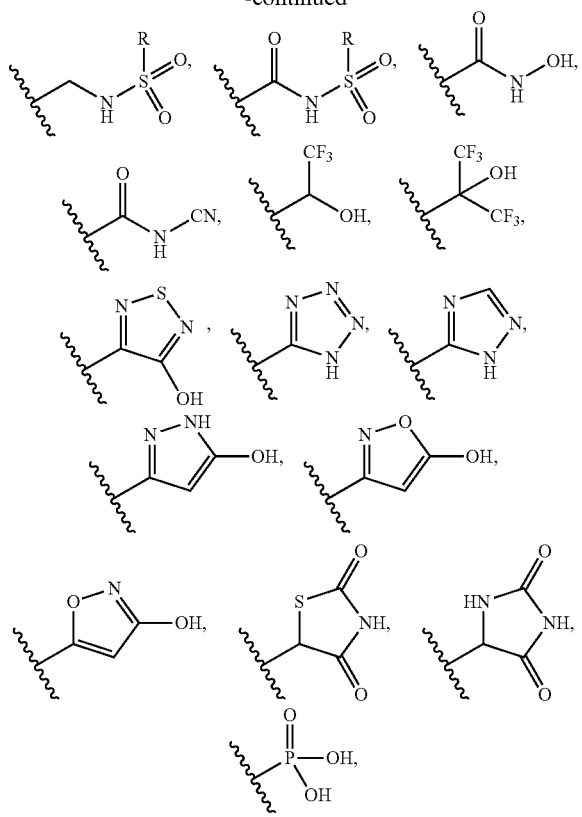

and the like. See, e.g., THE PRACTICE OF MEDICINAL CHEMISTRY (Academic Press: New York, 1996), at page 203.

In another embodiment, the invention provides a pharmaceutical composition of a compound as defined herein, or a pharmaceutically acceptable salt, solvate, stereoisomer, tautomer, or prodrug thereof in a pharmaceutically acceptable carrier.

Another embodiment of the invention is a method of inhibiting dihydroorotate dehydrogenase in a parasite. The method comprises contacting the parasite with a compound as defined herein or a pharmaceutically acceptable salt, solvate, stereoisomer, tautomer, or prodrug thereof.

DETAILED DESCRIPTION

Definitions

The term "alkyl" refers to a straight or branched chain, saturated hydrocarbon having the indicated number of carbon atoms. For example, ($C_1$-$C_8$)alkyl is meant to include but is not limited to methyl, ethyl, propyl, isopropyl, butyl, sec-butyl, tert-butyl, pentyl, isopentyl, neopentyl, hexyl, isohexyl, and neohexyl, etc. An alkyl group can be unsubstituted or optionally substituted with one or more substituents as described herein below.

The term "alkoxy" refers to an —O-alkyl group having the indicated number of carbon atoms. For example, a ($C_1$-$C_6$) alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aryl" refers to a 6- to 18-membered bicyclic, tricyclic, or polycyclic aromatic hydrocarbon ring system. Examples of an aryl group include phenyl, naphthyl, pyrenyl, and anthracyl. An aryl group can be unsubstituted or optionally substituted with one or more substituents as described herein below.

The term "halogen" and "halo" refers to —F, —Cl, —Br or —I.

The term "heteroatom" is meant to include oxygen (O), nitrogen (N), and sulfur (S).

The term "cycloalkyl" refer to monocyclic, bicyclic, tricyclic, or polycyclic, 3- to 14-membered ring systems, which are either saturated, unsaturated or aromatic moieties. A heterocycle may be attached to the cycloalkyl via any heteroatom or carbon atom. Cycloalkyl include aryls and hetroaryls. Representative examples of cycloalkyl include, but are not limited to cyclopropyl, cyclobutyl, cyclopentyl, cyclohexyl, cyclopentenyl, cyclohexenyl, phenyl, 2,3-dihydro-1H-indenyl, naphthyl, 1,2,3,4-tetrahydronaphthl, anthracyl, benzofuranyl, and benzothiophenyl. A cycloalkyl group can be unsubstituted or optionally substituted with one or more substituents as described herein below.

The term "nitrile or cyano" can be used interchangeably and refer to a —CN group which is bound to a carbon atom of an ($C_1$-$C_8$)alkyl group, a heteroaryl ring, aryl ring, cycloalkyl ring, and a heterocycloalkyl ring.

The term "haloalkoxy," refers to an —O—($C_1$-$C_8$)alkyl group wherein one or more hydrogen atoms in the $C_1$-$C_8$ alkyl group is replaced with a halogen atom, which can be the same or different. Examples of haloalkyl groups include, but are not limited to, difluoromethoxy, trifluoromethoxy, 2,2,2-trifluoroethoxy, 4-chlorobutoxy, 3-bromopropyloxy, pentachloroethoxy, and 1,1,1-trifluoro-2-bromo-2-chloroethoxy.

The term "alkylarylene" refers to $C_1$-$C_8$ alkyl group in which at least one hydrogen atom of the $C_1$-$C_8$ alkyl chain is replaced by an aryl atom, which may be optionally substituted with one or more substituents as described herein below. Examples of alkylarylene groups include, but are not limited to, methylphenylene, ethylnaphthylene, propylphenylene, and butylphenylene groups.

The term "nitro" refers to a —$NO_2$ group which is bound to a carbon atom of an ($C_1$-$C_8$)alkyl group, a heteroaryl ring, aryl ring, cycloalkyl ring, and a heterocycloalkyl ring.

The term "arylalkylene" refers to an aryl group having the indicated number of carbon atoms, in which one or more carbon atoms of the aryl group are bound to a carbon of a ($C_1$-$C_8$)alkyl group which can be linear or branched. Examples of arylalkylene groups include, but are not limited to, phenylmethylene or benzyl, phenylethylene, naphthylpropylene and naphthylisopropylene groups.

The term "arylalkoxylene" refers to an aryl group having the indicated number of carbon atoms, in which one or more carbon atoms of the aryl group are bound to a carbon of a —O—($C_1$-$C_8$)alkyl group.

The term "arylcycloalkylene" refers to an aryl group having the indicated number of carbon atoms, in which one or more carbon atoms of the aryl group are bound to a carbon of a ($C_3$-$C_{14}$)cycloalkyl group. Alternatively, two of the substituents on adjacent atoms of the aryl ring may optionally be replaced with a substituent of the formula -A-($CH_2$)$_r$—B—, where each of A and B are independently —$CH_2$—, or a single bond, and r is an integer of from 1 to 5. One of the single bonds of the new ring so formed may optionally be replaced with a double bond. Examples of arylcycloalkylene groups include, but are not limited to, phenylcycloproylene, naphthylcyclopropylene, dihydroindene and tetrahydronaphthylene groups.

The term "cycloalkylalkylene" refers to an cycloalkyl group having the indicated number of carbon atoms, in which one or more carbon atoms of the cycloalkyl group are bound to a carbon of a ($C_1$-$C_8$)alkyl group. Examples of cycloalkylarylene groups include, but are not limited to, cycloproylethylene, cyclopropylmethylene and cyclobutylpropylene groups.

The term "cycloalkylarylene" refers to an cycloalkyl group having the indicated number of carbon atoms, in which one or more carbon atoms of the cycloalkyl group are bound to a carbon of a ($C_3$-$C_{14}$)aryl group. Alternatively, two of the substituents on adjacent atoms of the cycloalkyl ring may optionally be replaced with a substituent of the formula -A=CH—CH=B-, where each of A and B are independently —CH groups. Examples of cycloalkylarylene groups include, but are not limited to, cyclopropylphenylene, cyclopropylnaphthylene, dihydroindene and tetrahydronaphthylene groups.

The term "haloalkyl," refers to a $C_1$-$C_8$ alkyl group wherein one or more hydrogen atoms in the $C_1$-$C_8$ alkyl group is replaced with a halogen atom, which can be the same or different. Examples of haloalkyl groups include, but are not limited to, —$CH_2Cl$, —$CH_2F$, —$CH_2CH_2Cl$, trifluoromethyl, 2,2,2-trifluoroethyl, 4-chlorobutyl, 3-bromopropyl, pentachloroethyl, 1,1,1-trifluoro-2-bromo-2-chloroethyl, trifluoromethyl (—$CF_3$) and -1,1,1-trifluoroethyl ($CH_2CF_3$).

The term "heteroaryl" denotes a monocyclic or polycyclic aromatic heterocyclic ring system ring of 5 to 14 members, having at least one heteroatom selected from nitrogen, oxygen and sulfur, and containing at least 1 carbon atom, including bicyclic, and tricyclic ring systems. Examples of heteroaryls include, but are not limited to, benzofuranyl, benzothiophenyl, quinolinyl, indolyl, benzoxazolyl, benzimidazolyl, benzothiazolyl, indole, oxazole, imidazole, thiazole, pyrimidinyl, cinnolinyl, phthalazinyl, quinazolinyl, pyrimidyl, chromenonyl, quinoxalinyl. A heteroaryl group can be unsubstituted or optionally substituted with one or more substituents as described herein below.

The term "heteroarylalkylene" denotes a monocyclic or polycyclic aromatic heterocyclic ring system ring of 5 to 14 members, having at least one heteroatom selected from nitrogen, oxygen and sulfur, and containing at least 1 carbon atom, including bicyclic, and tricyclic ring systems. The heteroaryl group may be attached via any heteroatom or carbon atom to a $C_1$-$C_8$ alkyl group. Examples of heteroarylalkylene include, but are not limited to, methylenethiazole, ethylenethiazole, methyleneimidazole and methylenethiophene groups.

For Formula IX compounds, substituents for the groups referred to as alkyl, heteroaryl, aryl, cycloalkyl, alkenyl, and alkynyl can be optionally selected from: —OR', =O, =NR', =N—OR', —NR'R", —SR', -halo, —SiR'R"R"', —OC(O)R', —C(O)R', —$CO_2$R', —CONR'R", —OC(O)NR'R", —NR"C(O)R', —NR"'C(O)NR'R", —NR"'$SO_2$NR'R", —NR"$CO_2$R', —NHC($NH_2$)=NH, —NR'C($NH_2$)=NH, —NHC($NH_2$)=NR', —S(O)R', —$SO_2$R', —$SO_2$NR'R", —NR"$SO_2$R', —CN and —$NO_2$, in a number ranging from zero to three, with those groups having zero, one or two substituents being exemplary. R', R" and R"' each independently refer to hydrogen, unsubstituted ($C_1$-$C_8$)alkyl, unsubstituted hetero($C_1$-$C_8$)alkyl, unsubstituted aryl and aryl substituted with one to three substituents selected from -halo, unsubstituted alkyl, unsubstituted alkoxy, unsubstituted thioalkoxy and unsubstituted aryl($C_1$-$C_4$)alkyl. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. An alkyl, aryl or heteroaryl group will have from zero to three substituents. In some embodiments, an alkyl or heteroalkyl radical is unsubstituted or monosubstituted. An alkyl or heteroalkyl radical can be unsubstituted.

Because compounds of the present invention can have asymmetric centers they can occur, except when specifically noted, as mixtures of enantiomers, diastereoisomers or as individual diastereomers and enantiomers, with all isomeric forms being contemplated by the present invention. The present invention also encompasses racemic mixtures. Compounds of the present invention embrace all conformational isomers, including, for example, cis- and trans-conformations. The separation of diasteroisomers or enantiomers can be achieved by known analytical methods, such as chiral chromatography, crystallization, or through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given that structure, then the depicted structure controls. Additionally, if the stereochemistry of a structure or a portion of a structure is not indicated with, for example, bold or dashed lines, the structure or portion of the structure is to be interpreted as encompassing all stereoisomers of it.

As used herein, the term "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The term "prodrug" denotes a derivative of a compound that can hydrolyze, oxidize, or otherwise react under biological conditions, in vitro or in vivo, to provide an active compound, particularly a compound of the invention. Examples of prodrugs include, but are not limited to, derivatives and metabolites of a compound of the invention that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate). For instance, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by BURGER'S MEDICINAL CHEMISTRY AND DRUG DISCOVERY 6$^{th}$ ed. (Wiley, 2001) and DESIGN AND APPLICATION OF PRODRUGS (Harwood Academic Publishers Gmbh, 1985).

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The terms "prevent," "preventing," and "prevention" refer to the prevention of the onset, recurrence, or spread of the disease in a patient resulting from the administration of a prophylactic or therapeutic agent.

The term "effective amount" refers to an amount of a compound of the invention or other active ingredient sufficient to provide a therapeutic or prophylactic benefit in the treatment or prevention of a disease or to delay or minimize symptoms associated with a disease. Further, a therapeutically effective amount with respect to a compound of the invention means that amount of therapeutic agent alone, or in combination with other therapies, that provides a therapeutic benefit in the treatment or prevention of a disease. Used in connection with a compound of the invention, the term can encompass an amount that improves overall therapy, reduces or avoids symptoms or causes of disease, or enhances the therapeutic efficacy of or synergies with another therapeutic agent.

The terms "modulate", "modulation" and the like refer to the ability of a compound to increase or decrease the function, or activity of, for example, DHODH. "Modulation", in its various forms, is intended to encompass inhibition, antagonism, partial antagonism, activation, agonism and/or partial agonism of the activity associated with DHODH. DHODH inhibitors are compounds that, e.g., bind to, partially or totally block stimulation, decrease, prevent, delay activation, inactivate, desensitize, or down regulate signal transduction. DHODH activators are compounds that, e.g., bind to, stimulate, increase, open, activate, facilitate, enhance activation, sensitize or up regulate signal transduction. The ability of a compound to modulate DHODH can be demonstrated in an enzymatic assay or a cell-based assay.

A "patient" includes an animal (e.g., cow, horse, sheep, pig, chicken, turkey, quail, cat, dog, mouse, rat, rabbit or guinea pig), in one embodiment a mammal such as a non-primate and a primate (e.g., monkey and human), and in another embodiment a human. In one embodiment, a patient is a human. In specific embodiments, the patient is a human infant, child, adolescent or adult.

Compounds

The present invention provides small molecule therapeutics that are potent inhibitors of the pyrimidine salvage enzyme DHOD. Compounds in accordance with this invention are shown in Table 1 below.

TABLE 1

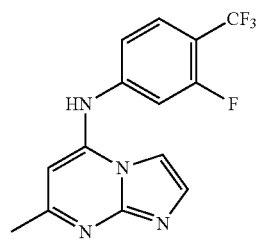 [SMILES: Cc1cc(Nc2ccc(C(F)(F)F)c(F)c2)n2ccnc2n1]

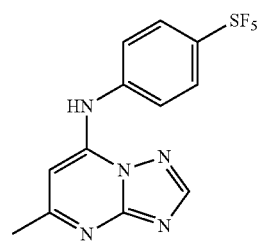

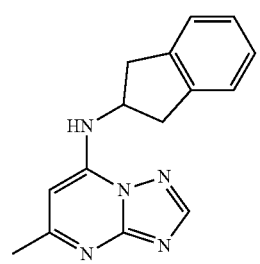 [SMILES: Cc1cc(NC2Cc3ccccc3C2)n2ncnc2n1]

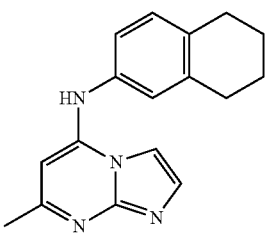 [SMILES: Cc1cc(Nc2ccc3c(c2)CCCC3)n2ccnc2n1]

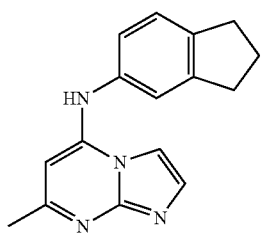 [SMILES: Cc1cc(Nc2ccc3c(c2)CCC3)n2ccnc2n1]

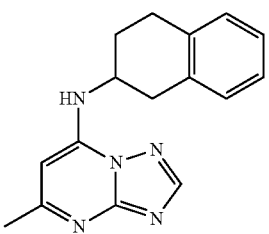 [SMILES: Cc1cc(NC2CCc3ccccc3C2)n2ncnc2n1]

TABLE 1-continued
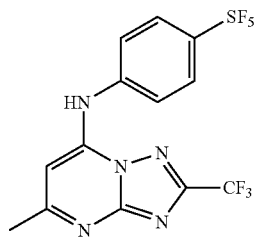
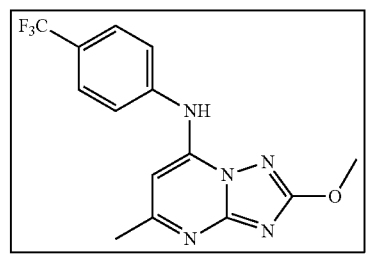
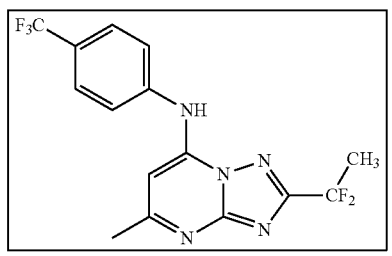 [SMILES: Cc1cc(Nc2ccc(C(F)(F)F)cc2)n2nc(C(C)(F)F)nc2n1]
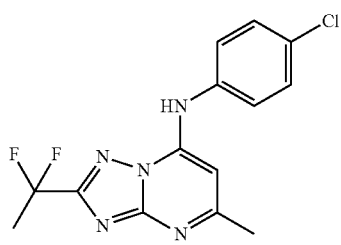
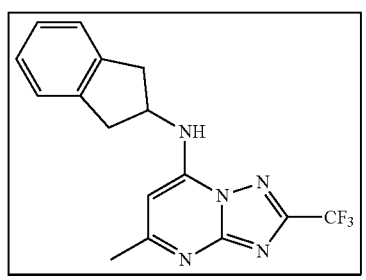 [SMILES: Cc1cc(NC2Cc3ccccc3C2)n2nc(C(F)(F)F)nc2n1]
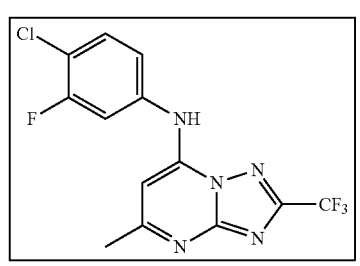
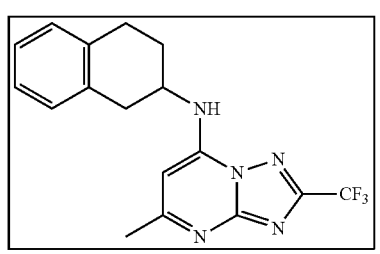 [SMILES: Cc1cc(NC2CCc3ccccc3C2)n2nc(C(F)(F)F)nc2n1]
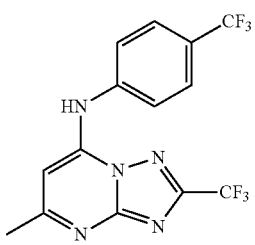
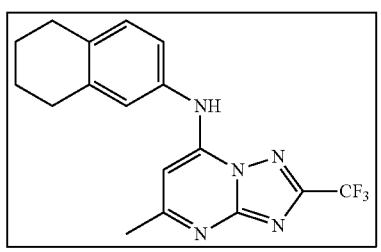 [SMILES: Cc1cc(Nc2ccc3c(c2)CCCC3)n2nc(C(F)(F)F)nc2n1]
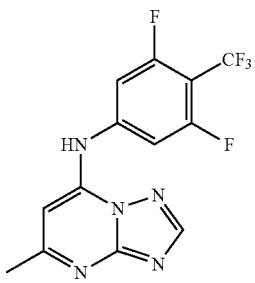
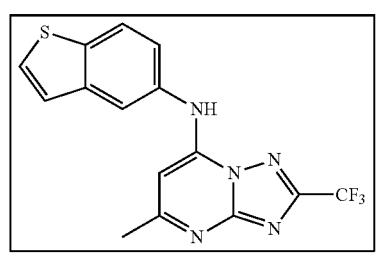 [SMILES: Cc1cc(Nc2ccc3sccc3c2)n2nc(C(F)(F)F)nc2n1]
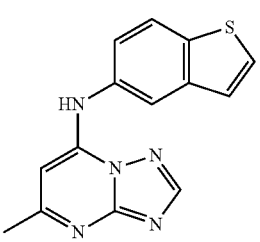 [SMILES: Cc1cc(Nc2ccc3sccc3c2)n2ncnc2n1]

TABLE 1-continued
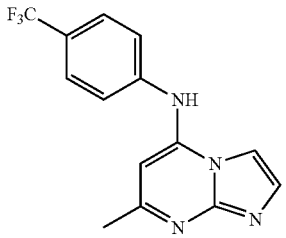
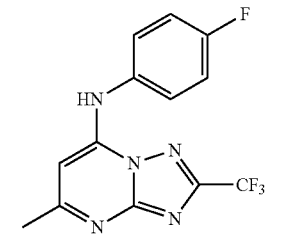
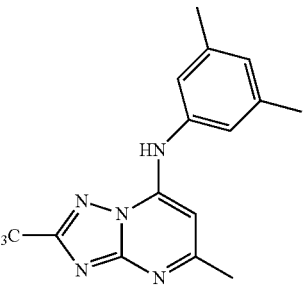
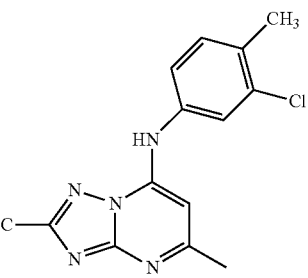
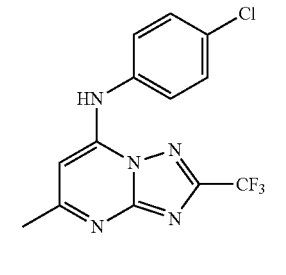
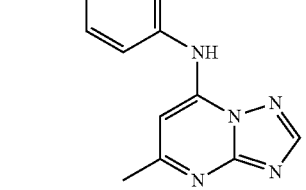
TABLE 1-continued
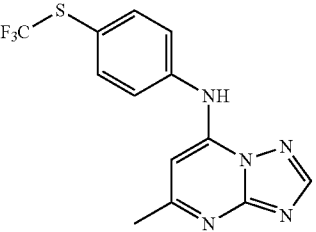 [SMILES: Cc1cc(Nc2ccc(SC(F)(F)F)cc2)n2ncnc2n1]
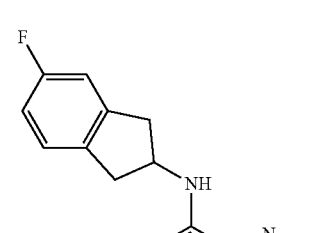
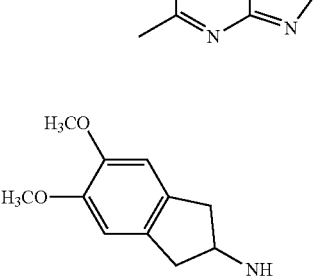
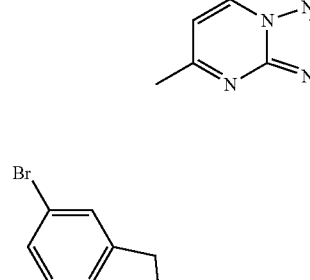
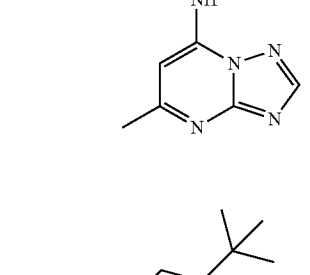
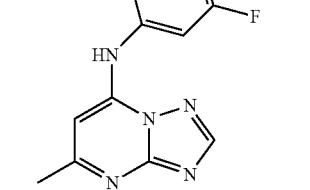

TABLE 1-continued
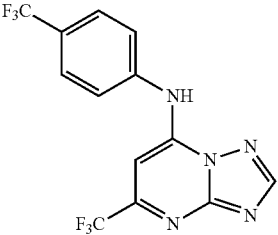 [SMILES: FC(F)(F)c1ccc(Nc2cc(C(F)(F)F)nc3ncnn23)cc1]
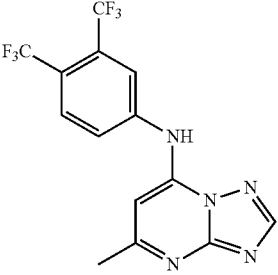 [SMILES: Cc1cc(Nc2ccc(C(F)(F)F)c(C(F)(F)F)c2)n2ncnc2n1]
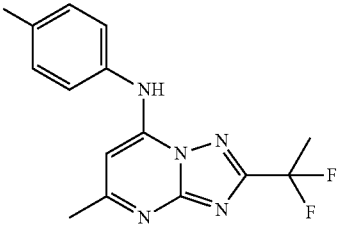
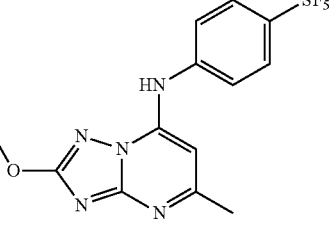
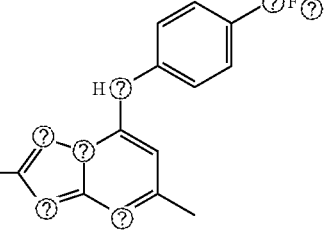
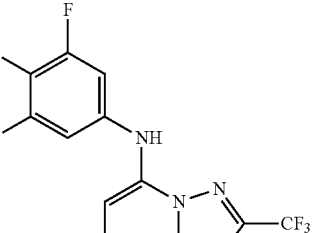
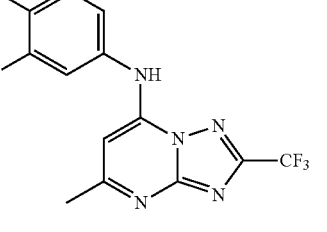
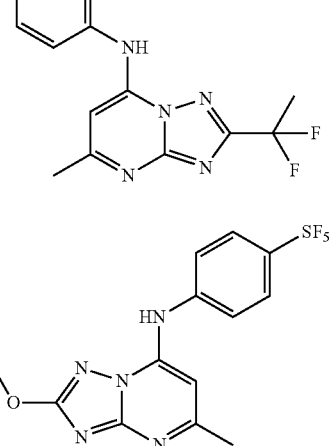
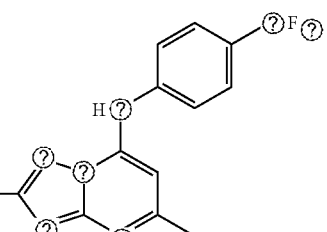
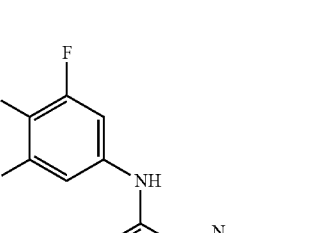
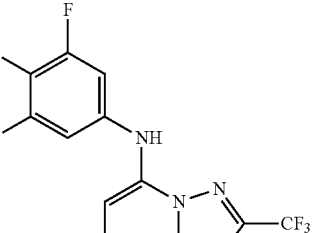
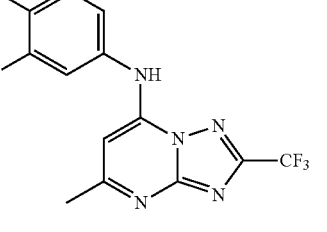
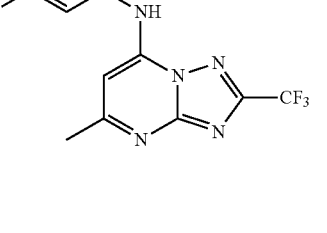

TABLE 1-continued

TABLE 1-continued

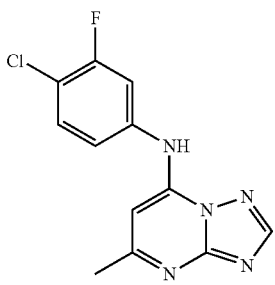 [SMILES: Cc1cc(Nc2ccc(Cl)c(F)c2)n2ncnc2n1]

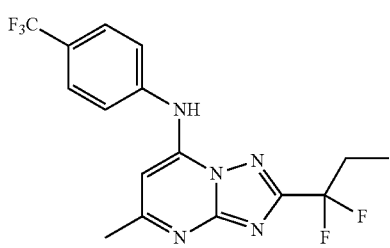 [SMILES: CCC(F)(F)c1nc2nc(C)cc(Nc3ccc(C(F)(F)F)cc3)n2n1]

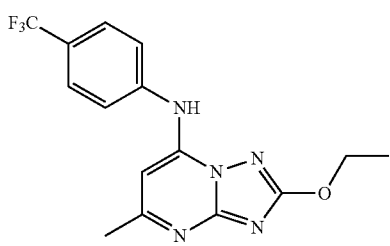 [SMILES: CCOc1nc2nc(C)cc(Nc3ccc(C(F)(F)F)cc3)n2n1]

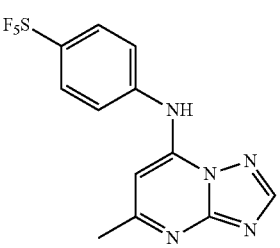

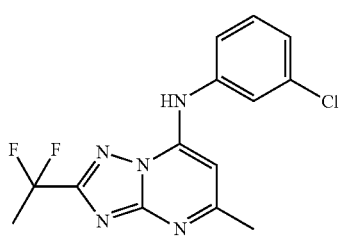 [SMILES: Cc1cc(Nc2cccc(Cl)c2)n2nc(C(C)(F)F)nc2n1]

In another embodiment, the DHOD inhibitors are based upon an imidazo[1,2a]pyrimidin-5-yl scaffold. Illustrative compounds of this embodiment are shown in Table 2 below.

TABLE 2

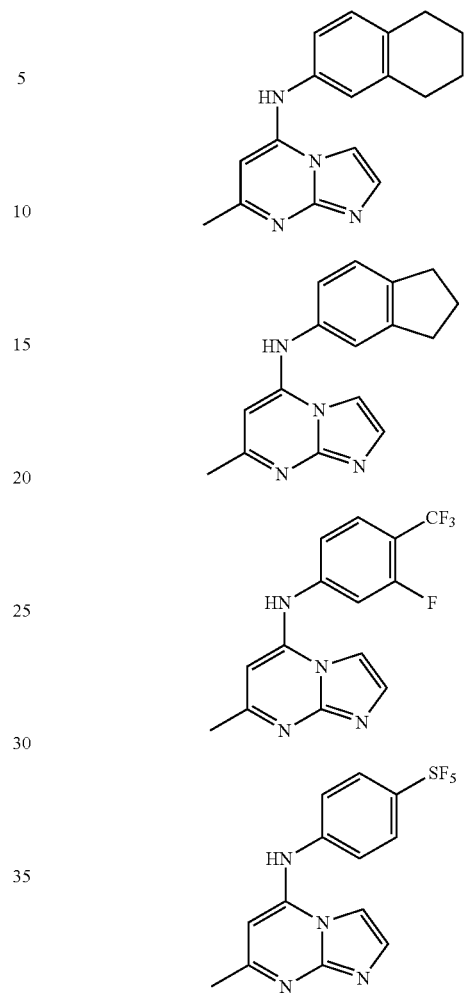

In other embodiments, the compounds of the inventions are triazolopyrimidine compounds that conform to Formula IX.

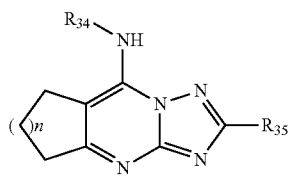

IX

In one embodiment, $R^{34}$ in Formula IX is selected from the group consisting of phenyl, aryl, 6- to 14-membered heterocycloalkyl, 6- to 14-membered arylcycloalkylene, 6- to 14-membered cycloalkylarylene, 3- to 8-membered cycloalkyl and 6- to 14-membered heteroaryl. Furthermore, each of these ring systems can be optionally substituted. For example, when $R^{34}$ is a phenyl, an aryl, a heterocycloalkyl, an arylcycloalkylene, a cycloalkylarylene, or a heteroaryl group, $R^{34}$ is optionally substituted with one or more members selected from the group consisting of F, I, Br, Cl, CN, $NO_2$, —$NR^aR^b$, ($C_1$-$C_8$)haloalkyl, ($C_1$-$C_8$)haloalkoxy, ($C_1$-$C_8$) alkoxy, oxaaryl, ($C_1$-$C_8$)alkyl, ($C_1$-$C_8$)-alkylarylene, ($C_2$-$C_8$) alkenyl, ($C_2$-$C_8$)alkynyl, ($C_3$-$C_8$)aryl($C_1$-$C_8$)alkylene, and aryl. For compounds that have an —$NR^aR^b$ group, each of $R^a$ and $R^b$ is independently selected from the group H, $(C_1-C_8)$ alkyl, aryl, heteroaryl, heterocycloalkyl, $(C_1-C_8)$haloalkoxy, $(C_1-C_8)$haloalkyl, $(C_3-C_8)$cycloalkyl and $(C_1-C_6)$hydroxyalkyl.

In some embodiments, $R^{34}$ is a phenyl and cycloalkylarylene ring substituted with halo- or alkyl. For instance, $R^{34}$ is a phenyl having $(C_1-C_8)$alkyl groups, such as methyl, ethyl propyl, isopropyl or is a phenyl group substituted with one or more halogens which may be the same or different.

Substituent $R^{35}$ is selected from the group consisting of hydrogen, halogen, $(C_1-C_8)$alkyl, $(C_2-C_8)$alkenyl, $(C_2-C_8)$alkynyl, $(C_1-C_8)$alkoxy, and $(C_1-C_8)$haloalkyl, phenyl, $(C_3-C_8)$cycloalkyl, $(C_3-C_8)$heteroaryl, $(C_3-C_8)$heterocycloalkyl, $(C_3-C_8)$aryl$(C_1-C_8)$alkylene, and $(C_3-C_8)$cycloalkyl$(C_1-C_8)$alkylene.

Illustrative compounds according to Formula IX are shown in table 3 below.

TABLE 3

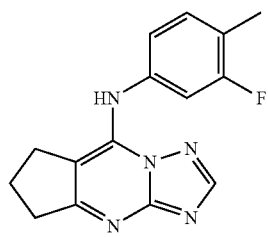 [SMILES: Cc1ccc(Nc2c3c(nc4ncnn24)CCC3)cc1F]

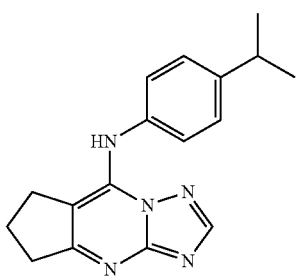 [SMILES: CC(C)c1ccc(Nc2c3c(nc4ncnn24)CCC3)cc1]

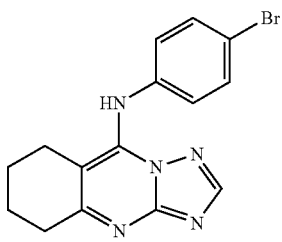 [SMILES: Brc1ccc(Nc2c3c(nc4ncnn24)CCCC3)cc1]

Pharmaceutical Formulations

Compounds in accordance with the invention are potent inhibitors of the enzyme DHOD implicated to play an important role in the de novo synthesis of pyrimidines in malarial parasites. Thus, the compounds and compositions of the same are effective as therapeutics for treating malaria. Accordingly, in one embodiment the invention provides a pharmaceutical composition comprising a compound selected from Table 4 or a salt, solvate, stereoisomer, tautomer or prodrug thereof, and a pharmaceutically acceptable carrier.

TABLE 4

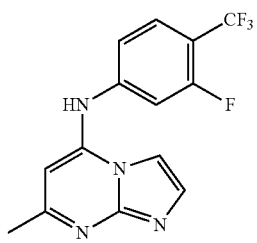 [SMILES: Cc1cc(Nc2ccc(C(F)(F)F)c(F)c2)n2ccnc2n1]

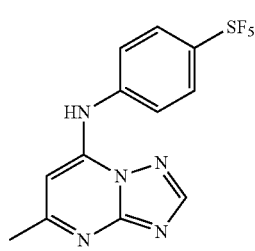

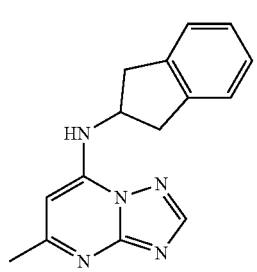 [SMILES: Cc1cc(NC2Cc3ccccc3C2)n2ncnc2n1]

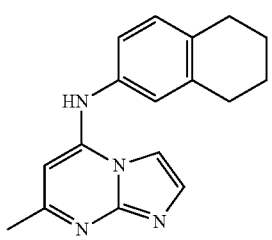

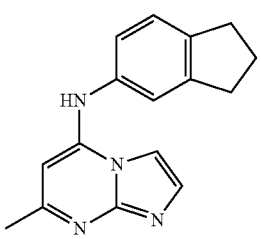 [SMILES: Cc1cc(Nc2ccc3c(c2)CCC3)n2ccnc2n1]

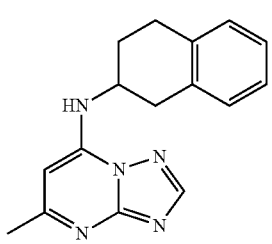 [SMILES: Cc1cc(NC2CCc3ccccc3C2)n2ncnc2n1]

TABLE 4-continued
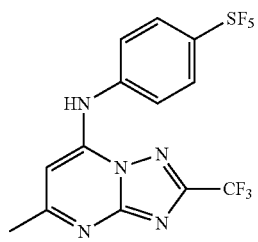
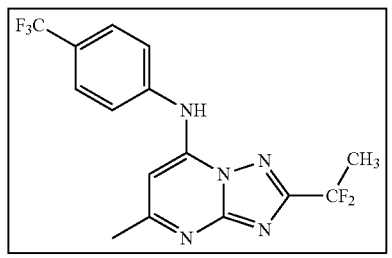 [SMILES: Cc1cc(Nc2ccc(C(F)(F)F)cc2)n2nc(C(C)(F)F)nc2n1]
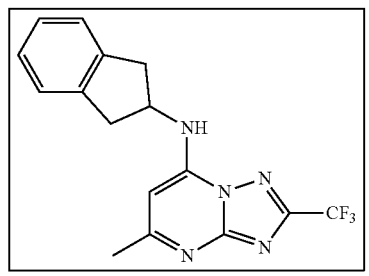 [SMILES: Cc1cc(NC2Cc3ccccc3C2)n2nc(C(F)(F)F)nc2n1]
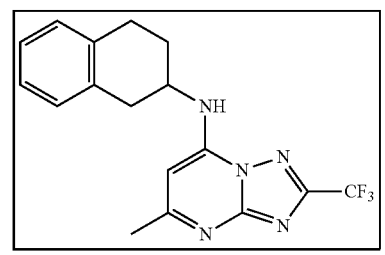 [SMILES: Cc1cc(NC2CCc3ccccc3C2)n2nc(C(F)(F)F)nc2n1]
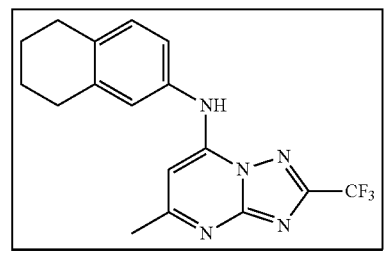 [SMILES: Cc1cc(Nc2ccc3c(c2)CCCC3)n2nc(C(F)(F)F)nc2n1]
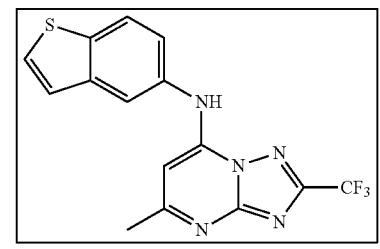 [SMILES: Cc1cc(Nc2ccc3sccc3c2)n2nc(C(F)(F)F)nc2n1]
TABLE 4-continued
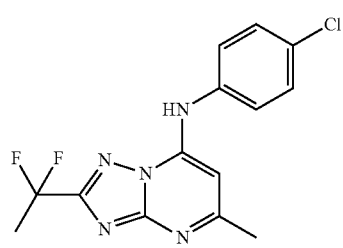 [SMILES: Cc1cc(Nc2ccc(Cl)cc2)n2nc(C(C)(F)F)nc2n1]
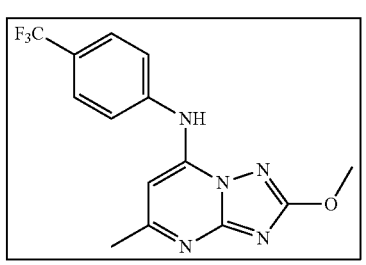 [SMILES: COc1nc2nc(C)cc(Nc3ccc(C(F)(F)F)cc3)n2n1]
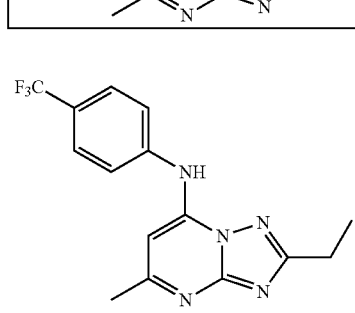
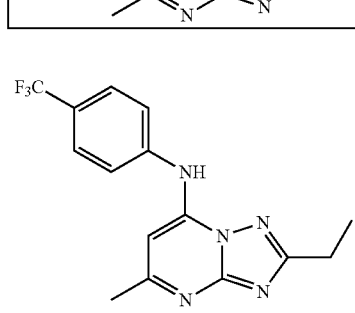
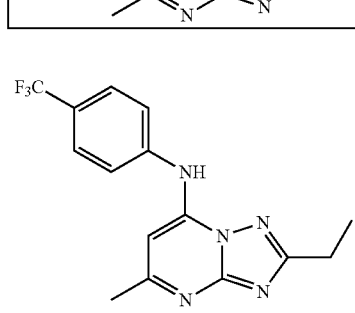
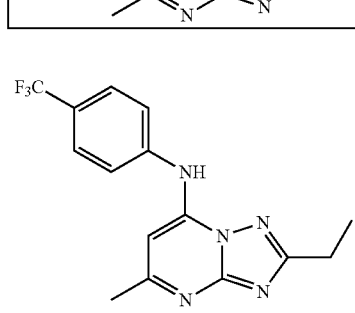

TABLE 4-continued
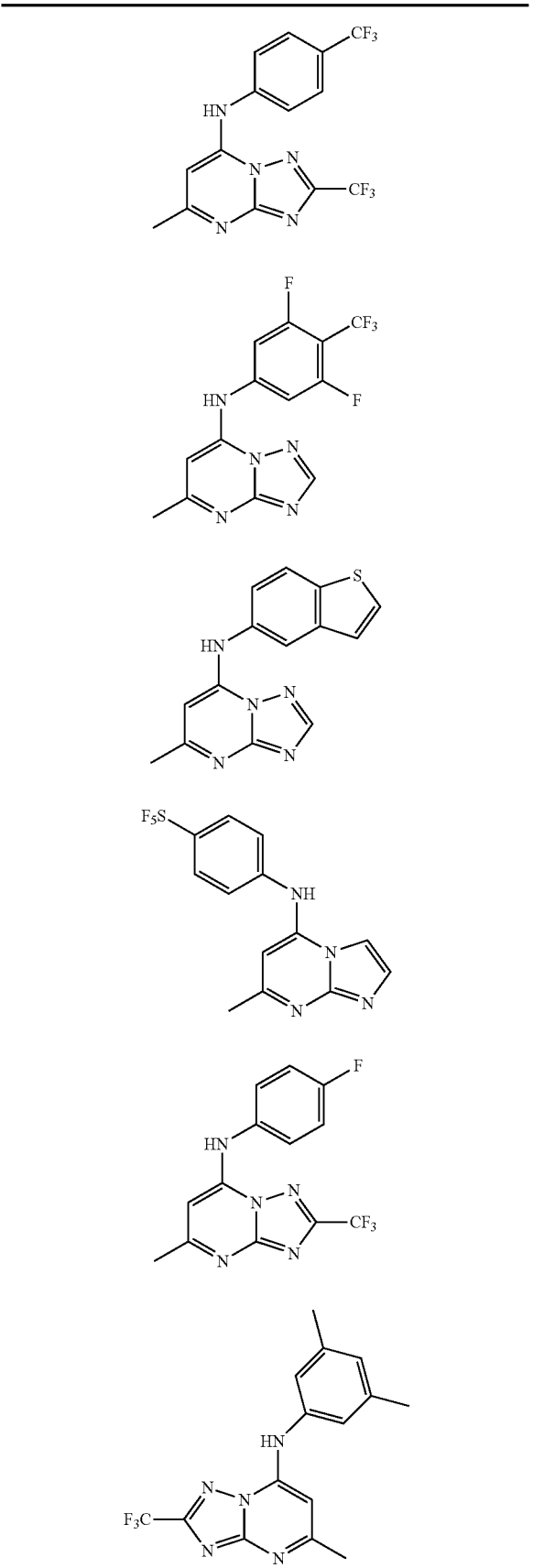
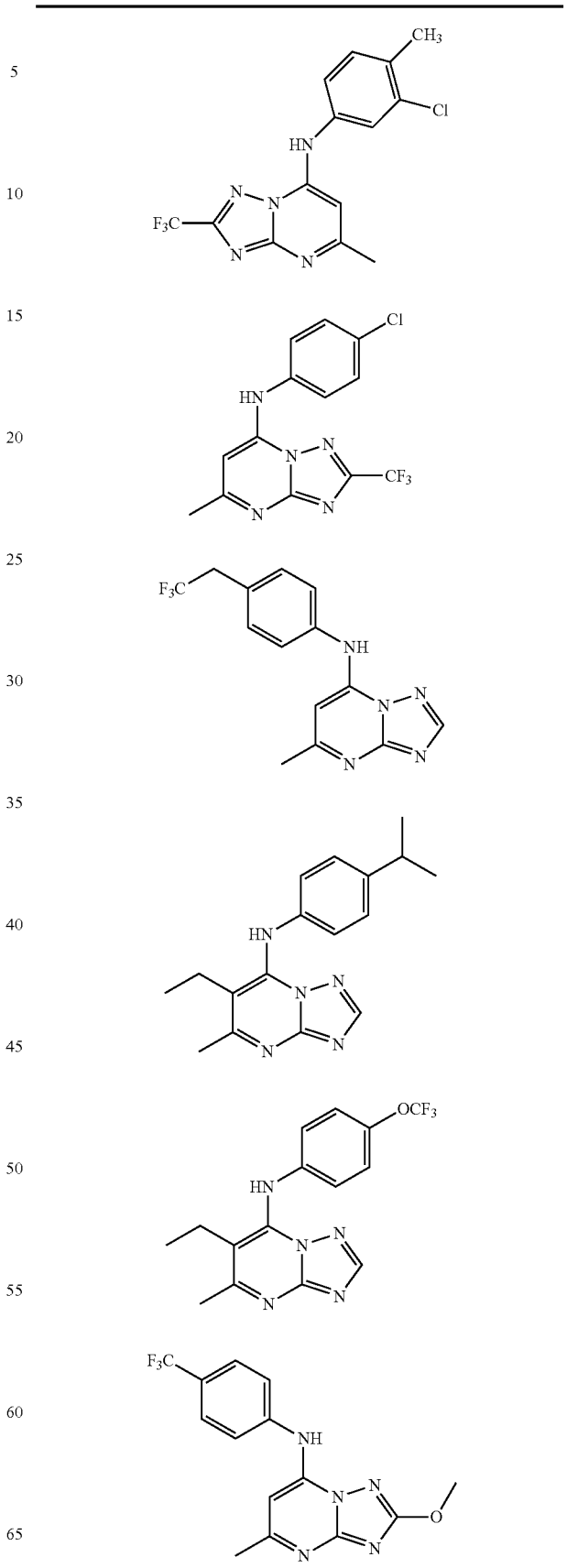

TABLE 4-continued
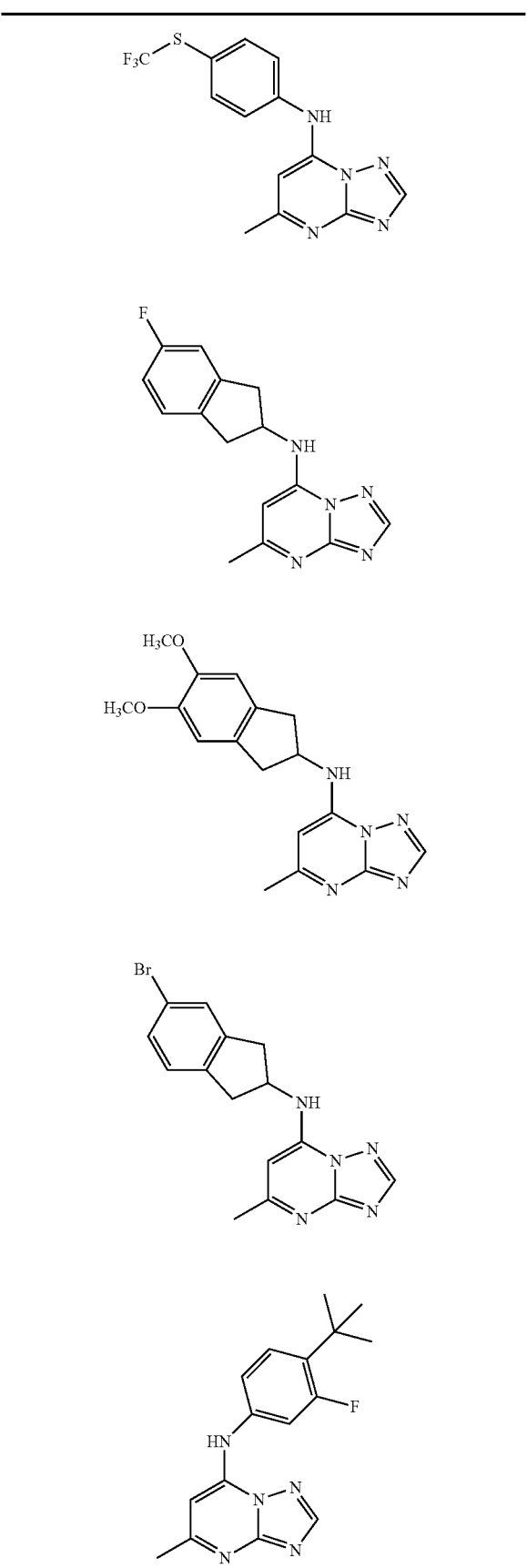
TABLE 4-continued
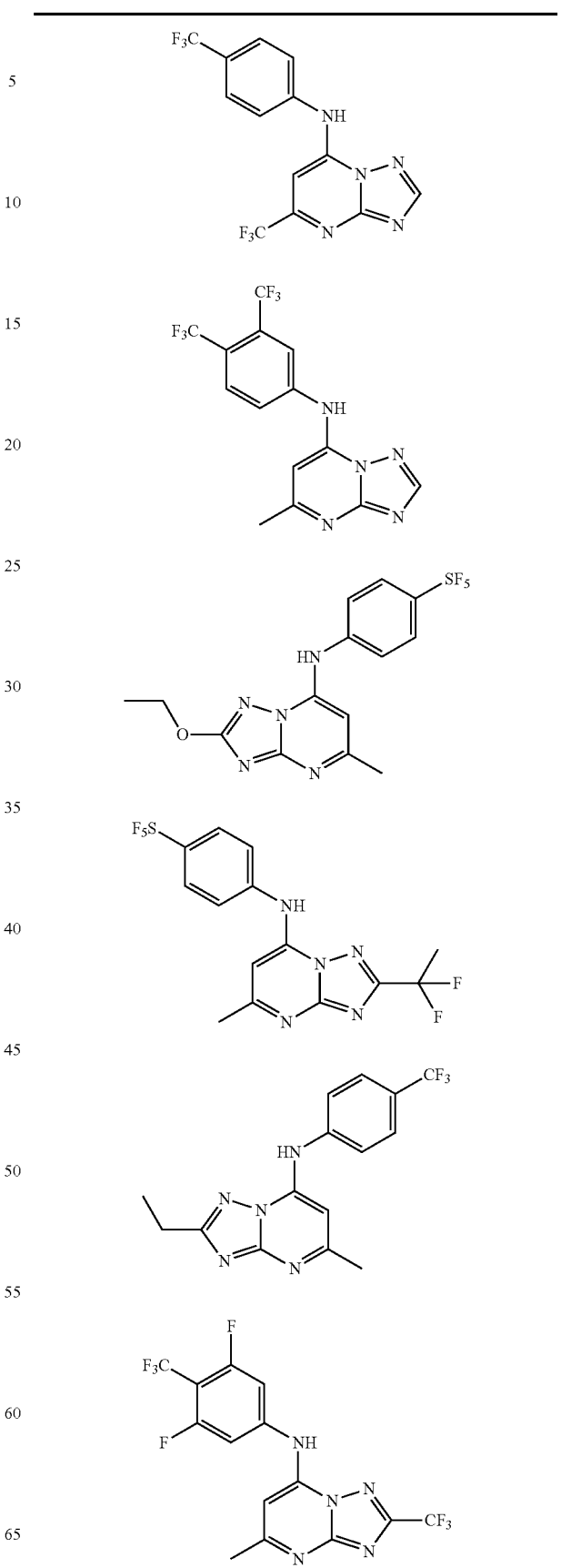

TABLE 4-continued
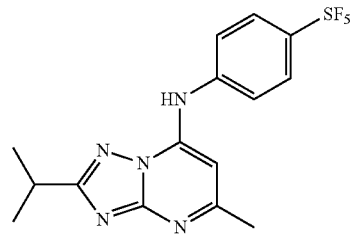
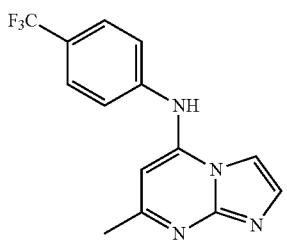
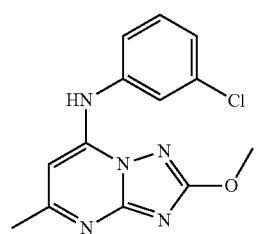
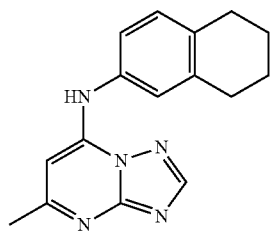 [SMILES: Cc1cc(Nc2ccc3c(c2)CCCC3)n2ncnc2n1]
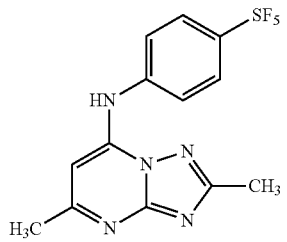
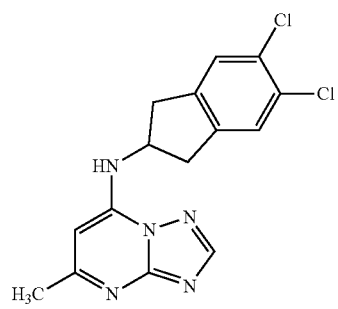 [SMILES: Cc1cc(NC2Cc3cc(Cl)c(Cl)cc3C2)n2ncnc2n1]
TABLE 4-continued
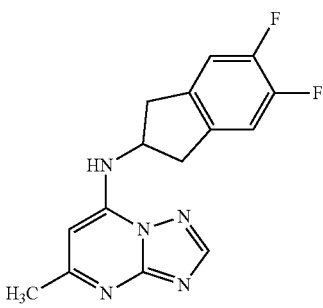 [SMILES: Cc1cc(NC2Cc3cc(F)c(F)cc3C2)n2ncnc2n1]
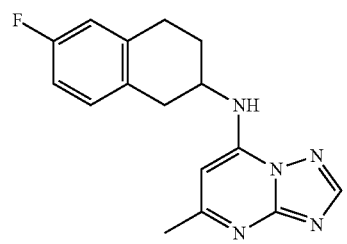 [SMILES: Cc1cc(NC2CCc3cc(F)ccc3C2)n2ncnc2n1]
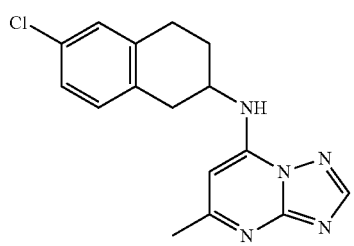 [SMILES: Cc1cc(NC2CCc3cc(Cl)ccc3C2)n2ncnc2n1]
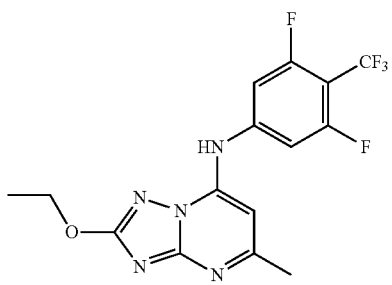 [SMILES: CCOc1nc2nc(C)cc(Nc3cc(F)c(C(F)(F)F)c(F)c3)n2n1]
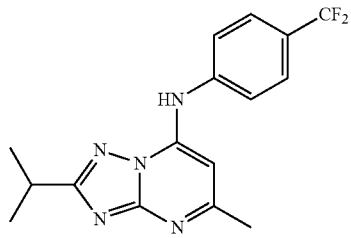
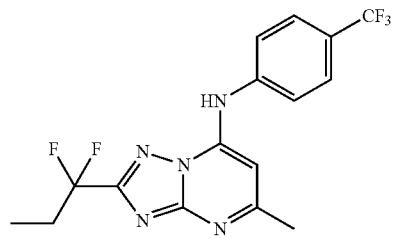 [SMILES: CCC(F)(F)c1nc2nc(C)cc(Nc3ccc(C(F)(F)F)cc3)n2n1]

TABLE 4-continued
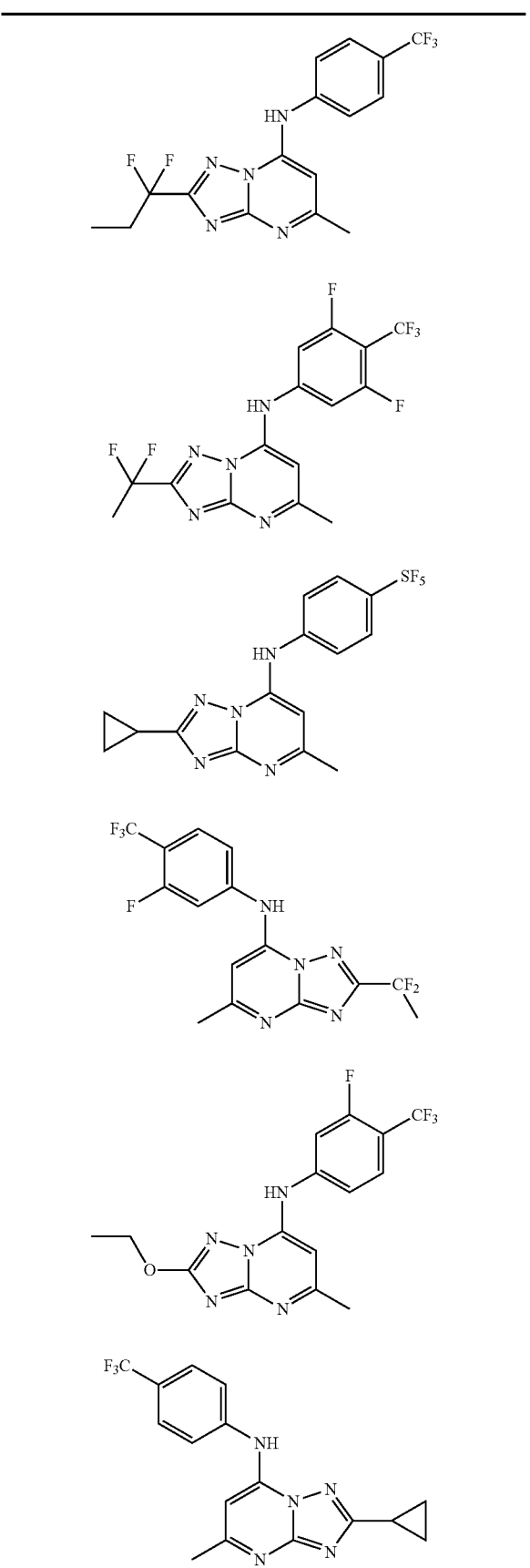
TABLE 4-continued
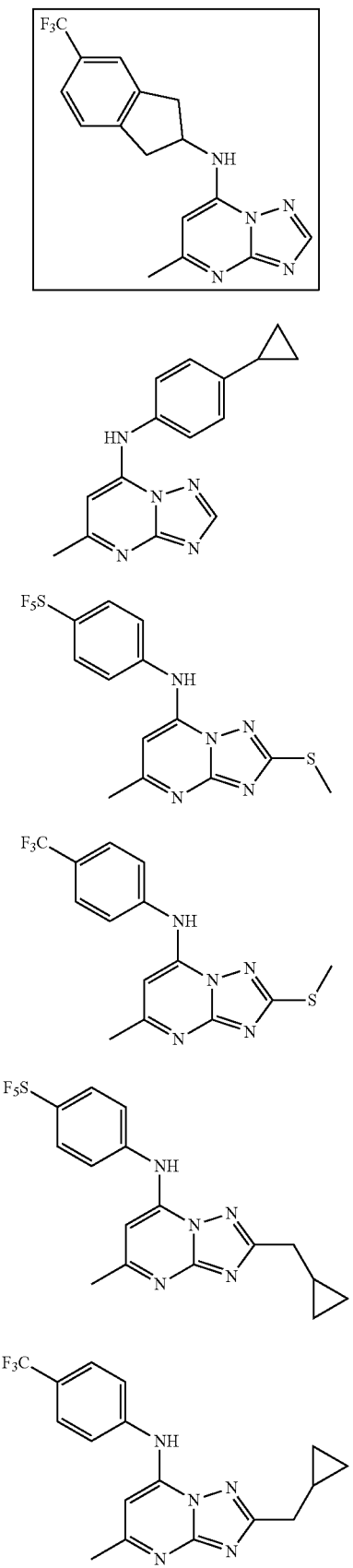

TABLE 4-continued

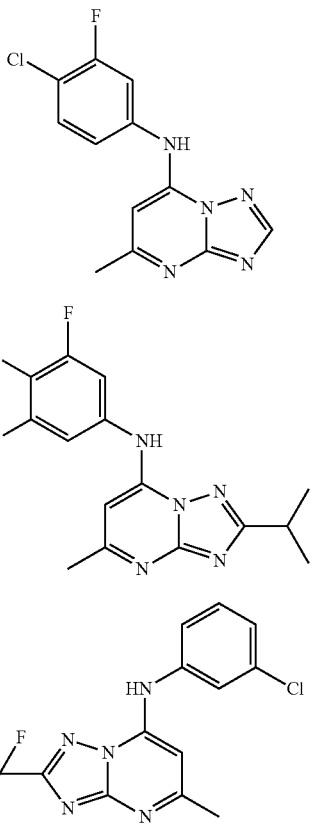

In accordance with this invention, pharmaceutically acceptable compositions of the compounds or their pharmaceutically acceptable salts further comprise a pharmaceutically acceptable carrier material. Any conventional carrier material can be utilized. For example, the carrier material can be an organic or inorganic inert carrier material, for example, one that is suitable for oral administration. Suitable carriers include water, gelatin, gum arabic, lactose, starch, magnesium stearate, talc, vegetable oils, polyalkylene-glycols, petroleum jelly and the like. Furthermore, the pharmaceutical preparations may also contain other pharmaceutically active agents. Additional additives such as flavoring agents, preservatives, stabilizers, emulsifying agents, buffers and the like may be added in accordance with accepted practices of pharmaceutical compounding.

The pharmaceutical preparations can be made up in any conventional form including a solid form for oral administration such as tablets, capsules, pills, powders, granules, and the like. The pharmaceutical preparations may be sterilized and/or may contain adjuvants such as preservatives, stabilizers, wetting agents, emulsifiers, salts for varying the osmotic pressure and/or buffers.

The compounds of the invention can also be administered to a patient in accordance with the invention by topical (including transdermal, buccal or sublingual), or parenteral (including intraperitoneal, subcutaneous, intravenous, intradermal or intramuscular injection) routes. In one embodiment, the compounds are administered orally. An oral dosage form comprises tablets, capsules of hard or soft gelatin methylcellulose or of another suitable material easily dissolved in the digestive tract. The oral dosages contemplated in accordance with the present invention will vary in accordance with the needs of the individual patient as determined by the prescribing physician. For instance, a daily dosage of from about 1 mg to about 50 mg per kg of body weight, such as from about 5 mg to about 25 mg per kg of body weight of the patient may be utilized.

It is within the purview of the present invention to incorporate the therapeutically active substance enumerated herein in any desired amount for enteral administration within an oral unit dosage form. Particularly suitable for enteral or oral administration are tablets, dragees or capsules having talc and/or carbohydrate carrier binder or the like, the carrier could be lactose and/or corn starch and/or potato starch. A syrup, elixir or the like can be used where a sweetened vehicle is employed. Sustained release compositions can also be formulated including those where the active component is protected with differentially degradable coatings, e.g., by microencapsulation, multiple coatings, etc.

For parenteral application, particularly suitable are solutions, typically oily or aqueous solutions as well as suspensions, emulsions, or implants, including suppositories. Therapeutic compounds will be formulated in sterile form in multiple or single dose formats such as being dispersed in a fluid carrier such as sterile physiological saline or 5% saline dextrose solutions commonly used with injectables.

For topical applications, the compound(s) of the invention can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

Given the ability of the compounds described herein to inhibit DHOD, these compounds are effective for use as therapeutics. In one embodiment, therefore, the invention provides a method for treating or preventing a condition or disorder associated with inhibition of *Plasmodium* dihydroorotate dehydrogenase in a subject by administering to the subject a therapeutically effective amount of a compound of the invention. Accordingly, the inventive compounds and pharmaceutically acceptable compositions of the same are candidate therapeutics for treating parasite infections in humans, such as a *P. falciparum* infection that causes the disease malaria.

In one embodiment, the invention provides a method of inhibiting dihydroorotate dehydrogenase in a parasite, comprising contacting said parasite with a compound of the invention. In some embodiments, the parasite is a member of the *Plasmodium* genus. In another embodiment, the parasite is *Plasmodium falciparum*.

The present invention is not to be limited in scope by the specific embodiments disclosed herein, which are intended as illustrations of a few embodiments of the invention. Rather, any embodiment that is functionally equivalent is within the scope of this invention. Indeed, various modifications of the invention in addition to those shown and described herein will become apparent to those skilled in the art and are intended to fall within the scope of the appended claims. To this end, it should be noted that one or more hydrogen atoms or methyl groups may be omitted from the drawn structures consistent with accepted shorthand notation of such organic compounds, and that one skilled in the art of organic chemistry would readily appreciate their presence.

EXAMPLES

Synthesis and Characterization of Compounds

1. The Synthesis of Intermediates

Example 1

Synthesis of 2,3-diamino-6-methyl-4(3H)-pyrimidinone (Intermediate 1)

To a stirring solution of NaOEt prepared from sodium (FLUKA, 9.19 g, 400 mmol) and ethanol (350 mL) was added aminoguanidine hydrochloride (ALDRICH, 44.2 g, 400 mmol). The reaction mixture was heated at 50° C. for 30 min. Then, the mixture was filtered to remove NaCl, and ethyl 3-oxobutanoate (ALDRICH, 25.3 mL, 200 mmol) was added to the filtrate. The reaction mixture was heated under reflux for 5 h and, then, stirred at room temperature overnight. The precipitate obtained was filtered and dried under vacuum to afford Intermediate 1 as a pale pink solid.

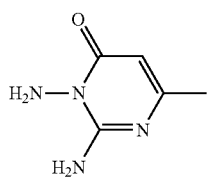

Intermediate 1

$^1$H NMR (400 MHz, DMSO-$d_6$) δ ppm: 7.02 (bs, 2H), 5.51 (s, 1H), 5.29 (s, 2H), 1.98 (s, 3H); [ES+MS] m/z 141 (MH)$^+$.

Example 2

Synthesis of 2-(1,1-difluoroethyl)-5-methyl[1,2,4]triazolo[1,5-a]pyrimidin-7-ol (Intermediate 2)

Intermediate 1 was added to a stirring solution of NaOEt prepared from sodium (FLUKA, 3.28 g, 143 mmol) and ethanol (150 ml) and the mixture was heated at 80° C. for 30 minutes. The reaction mixture was cooled down to room temperature and ethyl 2,2-difluoropropanoate (FLUOROCHEM, 11.83 g, 86 mmol) was added. The mixture was stirred at room temperature for 30 min before being heated to 80° C. for 1.5 h. The reaction mixture was concentrated to dryness and water (200 mL) was added. The reaction mixture pH was adjusted to 4 by addition of 2N HCl solution while a white solid precipitated. The solid was filtered, washed with water and dried under vacuum to afford Intermediate 2. The mother liquors were extracted with DCM (5×35 mL) and the combined organic layers were dried over Na$_2$SO$_4$, filtered, and concentrated under vacuum to give more Intermediate 2 as a white solid.

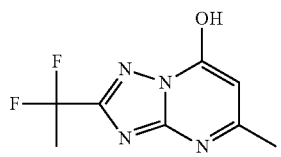

Intermediate 2

$^1$H NMR (400 MHz, DMSO-$d_6$) δ ppm: 13.39 (bs, 1H), 5.91 (s, 1H), 2.33 (s, 3H), 2.06 (t, 3H); [ES+MS] m/z 215 (MH)$^+$.

Example 3

Synthesis of 7-chloro-2-(1,1-difluoroethyl)-5-methyl[1,2,4]triazolo[1,5-a]pyrimidine (Intermediate 3)

This intermediate was synthesized by suspending Intermediate 2 in phosphorus oxychloride (ALDRICH, 21.98 ml, 236 mmol) was heating the mixture under reflux for 2 h, the starting material dissolved meanwhile. An aliquot of the reaction was partitioned between NaCO$_3$ 10% aq. (1 mL) and DCM (1 mL) and the organic phase was checked by TLC (Hexane/AcOEt 6/4) showing the reaction was complete. The reaction mixture was slowly added to a mixture of water and ice. The solution was neutralized with 10% aq. Na$_2$CO$_3$ (800 mL approx.) and product was extracted with DCM (250 mL). The aqueous layer was further extracted with DCM (2×150 mL) and the combined organic layers were washed with water (200 mL), then with brine (200 mL) and dried over MgSO$_4$. Solvent was removed under reduced pressure. The crude product was purified (silica gel column, eluting with Hexane/AcOEt mixtures from 100:0 to 50:50%) and Intermediate 3 was obtained as a white solid.

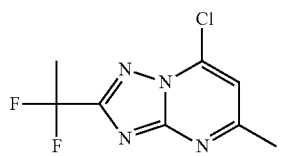

Intermediate 3

$^1$H NMR (400 MHz, CDCl$_3$) δ ppm: 7.17 (s, 1H), 2.75 (s, 3H), 2.18 (t, 3H); [ES+MS] m/z 233 (MH)$^+$.

Example 4

Synthesis of 2-ethyl-5-methyl[1,2,4]triazolo[1,5-a]pyrimidine-7-ol (Intermediate 4)

Intermediate 1 (0.4 g, 2.85 mmol) was allowed to react with propionyl chloride (ALDRICH, 0.372 mL, 4.28 mmol) in a mixture of 1,4-dioxane (8 mL) and N,N-dimethylformamide (2 mL) overnight under refluxing conditions. The reaction was concentrated under vacuum and the residue was purified (silica gel column, eluting with DCM:MeOH mixtures from 100:0 to 90:10%) to obtain 7-hydroxy-2-ethyl-5-methyl[1,2,4]triazolo[1,5-a]pyrimidine (Intermediate 4) as a white solid.

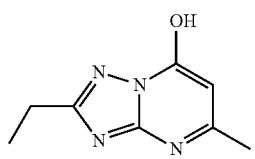

Intermediate 4

¹H NMR (400 MHz, CDCl₃) δ ppm: 5.89 (s, 1H), 2.87 (q, 2H), 2.50 (s, 3H), 1.41 (t, 3H); [ES+MS] m/z 179 (MH)⁺.

Example 5

Synthesis of 7-chloro-2-ethyl-5-methyl[1,2,4]triazolo[1,5-a]pyrimidine (Intermediate 5)

The titled compound (Intermediate 5), was obtained by refluxing a suspension of Intermediate 4 (0.3 g, 1.684 mmol) in phosphorus oxychloride (ALDRICH, 1.88 mL, 20.2 mmol) for 2 h and then, adding the reaction mixture slowly to a mixture of water and ice. The solution was neutralized with solid Na₂CO₃ and extracted with DCM (25 mL). The aqueous layer was further extracted with DCM (2×5 mL) and the combined organic layers were washed with water (20 mL), then with brine (20 mL), and then dried over MgSO₄. Solvent was removed under reduced pressure and the crude product was purified (silica gel column, eluting with Hexane/EtOAc mixtures from 100:0 to 40:60%) to obtain Intermediate 5 as a white solid.

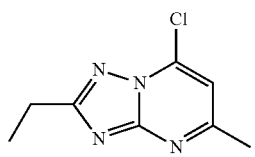

Intermediate 5

¹H NMR (400 MHz, CDCl₃) δ ppm: 7.01 (s, 1H), 2.98 (q, 2H), 2.68 (s, 3H), 1.43 (t, 3H); [ES+MS] m/z 197 (MH)⁺.

Example 6

Synthesis of 2-(1,1-difluoropropyl)-5-methyl[1,2,4]triazolo[1,5-a]pyrimidin-7-ol. (Intermediate 6)

To a solution of NaEtO prepared from sodium (FLUKA, 0.152 g, 6.62 mmol) and ethanol (25 mL), Intermediate 1 (0.773 g, 5.52 mmol) was added, and the mixture was heated at 80° C. for 30 min. Then, the reaction was cooled down to room temperature and ethyl 2,2-difluorobutanoate (FLUOROCHEM, 1007 mg, 6.62 mmol) was added and the reaction mixture was stirred at 80° C. for 3 h. A solution of HCl (1.655 mL, 6.62 mmol) in dioxane was added and a white solid was formed. The residue was purified (silica gel column, eluting with DCM:MeOH mixtures from 100:0 to 90:10%) to obtain Intermediate 6 as a white solid.

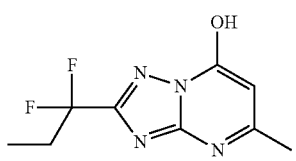

Intermediate 6

¹H NMR (400 MHz, DMSO-d₆) δ ppm: 13.36 (bs, 1H), 5.90 (s, 1H), 2.40-2.32 (m, 2H), 2.32 (s, 3H), 0.99 (t, 3H); [ES+MS] m/z 229 (MH)⁺.

Example 7

Synthesis of 7-chloro-2-(1,1-difluoropropyl)-5-methyl[1,2,4]triazolo[1,5-a]pyrimidine (Intermediate 7)

A suspension of Intermediate 6 (0.660 g, 2.89 mmol) in phosphorus oxychloride (ALDRICH, 0.404 mL, 43.4 mmol) was heated under reflux for 2 h, the starting material dissolving during the process. The mixture was slowly added to a mixture of water and ice. The resulting solution was neutralized with solid Na₂CO₃ and extracted with DCM (25 mL). The aqueous layer was further extracted with DCM (2×5 mL) and the combined organic layers were washed with water (20 mL); then with brine (20 mL), and dried over MgSO₄. Solvent was removed under reduced pressure and the crude product was purified (silica gel column, eluting with Hexane/EtOAc mixtures from 100:0 to 40:60%) to afford Intermediate 7 as a pale yellow solid.

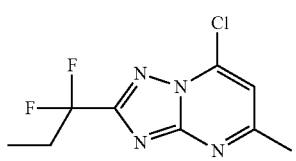

Intermediate 7

¹H NMR (400 MHz, CDCl₃) δ ppm: 7.17 (s, 1H), 2.75 (s, 3H), 2.53-2.41 (m, 2H), 1.13 (t, 3H); [ES+MS] m/z 247 (MH)⁺.

Example 8

Synthesis 7-chloro-5-methyl-2-(methylthio)[1,2,4]triazolo[1,5-a]pyrimidine (Intermediate 8)

Thus, refluxing a suspension of 7-hydroxy-5-methyl-2-methylthio-5-triazolo[1,5-a]pyrimidine (TCI, 2 g, 10.19 mmol) in phosphorus oxychloride (ALDRICH, 5 ml, 53.6 mmol) for 10 h, resulted in solubilization of the starting material and a change in color of the reaction mixture to bright orange. TLC analysis (Hexane/EtOAC 1:1) showed a very messy reaction that had not reached completion but it was decided to stop it to prevent further product degradation. Hence, the reaction mixture was added dropwise to iced water. The solution was neutralized with aq. 1N Na₂CO₃ and product was extracted with DCM. The aqueous layer was further extracted with DCM and the combined organic layers were washed with brine and dried over anhydrous. Na₂SO₄. Solvent was removed under reduced pressure yielding a reddish solid which was purified by flash chromatography (Si, eluting with Hexane/EtOAc mixtures from 95:5 to 40:60%). Upon collection of the appropriate fractions, the title compound was obtained as a white solid.

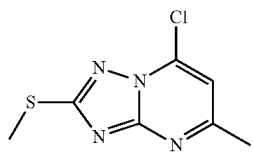

Intermediate 8

$^1$H NMR (300 MHz, CDCl$_3$) δ ppm: 6.99 (s, 1H), 2.74 (s, 3H), 2.68 (s, 3H); [ES+MS] m/z 215 (MH)$^+$.

Example 9

Synthesis of 5-methyl-2-(methylthio)-N-[4-(pentafluoro-λ$^6$-sulfanyl)phenyl][1,2,4]triazolo[1,5-a]pyrimidin-7-amine (Intermediate 9)

To a suspension of 7-chloro-5-methyl-2-(methylthio)[1,2,4]triazolo[1,5-a]pyrimidine (Intermediate 8, (0.2 g, 0.932 mmol)), in ethanol (10 mL), 4-aminophenylsulfur pentafluoride (MANCHESTER, 0.204 g, 0.932 mmol) was added and the mixture was stirred at room temperature until reaching completion. Anhydrous ammonia (0.133 mL, 0.932 mmol) was then added to the mixture and solvent was removed in vacuo. The crude mixture was purified by flash chromatography (Si, eluting with Hexane/EtOAc mixtures form 95:5 to 40:60%). Upon collection of the appropriate fractions, the title compound was obtained as a light yellow solid.

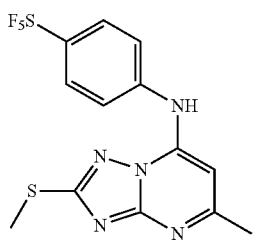

Intermediate 9

$^1$H NMR (300 MHz, DMSO-d$_6$) δ ppm: 10.39 (s, 1H), 7.98-7.96 (m, 2H), 7.67-7.65 (m, 2H), 6.70 (s, 1H), 2.68 (s, 3H), 2.44 (s, 3H); [ES+MS] m/z 398 (MH)$^+$.

Example 10

Synthesis of 5-methyl-2-(methylsulfonyl)-N-[4-(pentafluoro-λ$^6$-sulfanyl)phenyl][1,2,4]triazolo[1,5-a]pyrimidin-7-amine (Intermediate 10)

To a mixture of 5-methyl-2-(methylthio)-N-[4-(pentafluoro-λ$^6$-sulfanyl)phenyl][1,2,4]triazolo[1,5-a]pyrimidin-7-amine (0.279 g, 0.702 mmol) and acetic acid (5 mL), sodium tungstate dihydrate (ALDRICH, 7.87 mg, 0.024 mmol) was added at room temperature. The reaction mixture was vigorously stirred and hydrogen peroxide (0.13 mL, 1.40 mmol) was added slowly at 40° C. The resulting mixture was then heated at 50° C. until reaching completion. The excess hydrogen peroxide was destroyed by the addition of an aqueous solution of sodium sulfite, product being extracted with DCM several times. The combined organic layers were washed with brine and dried over anhydrous Na₂SO₄. A white solid was obtained upon solvent removal in vacuo which was purified by flash chromatography (Si, eluting with Hexane/EtOAc mixtures from 95:5% to 0:100%). Upon collection of the appropriate fractions, the title compound was obtained as a white solid.

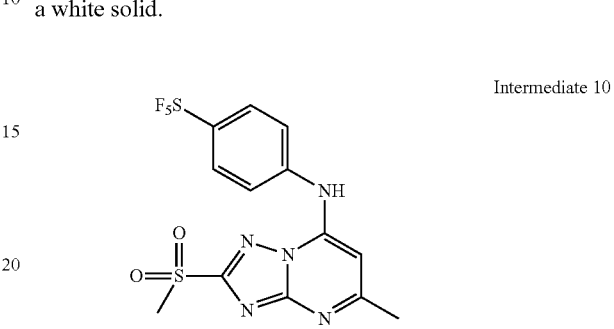

Intermediate 10

$^1$H NMR (300 MHz, CDCl$_3$) δ ppm: 8.23-8.10 (br s, 1H), 7.93-7.91 (m, 2H), 7.50-7.48 (m, 2H), 6.66 (s, 1H), 3.43 (s, 3H), 2.65 (s, 3H); [ES+MS] m/z 430 (MH)$^+$.

Example 11

Synthesis of N-[3,5-difluoro-4-(trifluoromethyl)phenyl]-5-methyl-2-(methylthio)[1,2,4]triazolo[1,5-a]pyrimidin-7-amine (Intermediate 11)

To a suspension of 7-chloro-5-methyl-2-(methylthio)[1,2,4]triazolo[1,5-a]pyrimidine (Intermediate 8 (0.286 g, 1.332 mmol)) in ethanol (5 mL), 4-amino-2,6-difluorobenzotrifluoride (FLUOROCHEM, 0.263 g, 1.332 mmol) was added and the mixture was stirred at room temperature until reaching completion. Anhydrous ammonia (0.190 mL, 1.332 mmol) was added and solvent was removed in vacuo. The residue was purified by flash chromatography (Si, eluting with Hexane/EtOAc mixtures from 95:5 to 40:60%). Upon collection of the appropriate fractions, the title compound was obtained as a white solid.

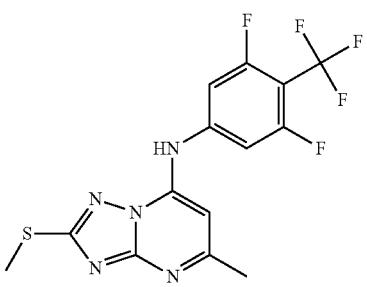

Intermediate 11

$^1$H NMR (300 MHz, CDCl$_3$) δ ppm: 8.01-7.85 (br, 1H), 7.04-7.02 (m, 2H), 6.59 (s, 1H), 2.73 (s, 3H), 2.63 (s, 3H); [ES+MS] m/z 376 (MH)$^+$.

Example 12

Synthesis of N-[3,5-difluoro-4-(trifluoromethyl)phenyl]-5-methyl-2-(methylsulfonyl)[1,2,4]triazolo[1,5-a]pyrimidin-7-amine (Intermediate 12)

To a suspension of N-[3,5-difluoro-4-(trifluoromethyl)phenyl]-5-methyl-2-(methylthio)[1,2,4]triazolo[1,5-a]pyrimidin-7-amine (0.4 g, 1.066 mmol)) in acetic acid (5 mL), sodium tungstate dihydrate (ALDRICH, 0.012 g, 0.036 mmol) was added at room temperature The reaction mixture was vigorously stirred and hydrogen peroxide (0.198 mL, 2.132 mmol) was added slowly at 40° C. The resulting mixture was then heated at 50° C. for 5 h, and then at room temperature overnight. The excess hydrogen peroxide was destroyed by the addition of an aqueous solution of sodium sulfite, product being extracted with DCM several times. The combined organic layers were washed with brine, dried over anhydrous $Na_2SO_4$ and solvent was evaporated under reduced pressure. The crude mixture was purified by flash chromatography (Si, eluting with Hexane/EtOAC mixtures from 95:5 to 0:100%). The title compound was obtained a white solid.

Intermediate 12

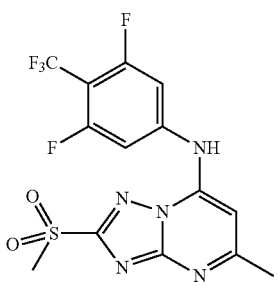

$^1$H NMR (300 MHz, $CDCl_3$) δ ppm: 8.66-8.40 (br s, 1H), 7.15-7.13 (m, 2H), 6.78 (s, 1H), 3.42 (s, 3H), 2.69 (s, 3H); [ES+MS] m/z 408 (MH)$^+$.

Example 13

Synthesis of N-[3-fluoro-4-(trifluoromethyl)phenyl]-5-methyl-2-(methylthio)[1,2,4]triazolo[1,5-a]pyrimidin-7-amine (Intermediate 13)

To a suspension of 7-chloro-5-methyl-2-(methylthio)[1,2,4]triazolo[1,5-a]pyrimidine (Intermediate 8 (0.3 g, 1.397 mmol)) in ethanol (5 mL), 4-amino-2-fluorobenzotrifluoride (ALFAAESAR, 0.25 g, 1.397 mmol) was added and the mixture was stirred at room temperature for 2 h. Anhydrous ammonia (0.2 mL, 1.397 mmol) was added and solvent was removed in vacuo. The residue was purified by flash chromatography (Si, eluting with Hexane/EtOAc mixtures form 95:5 to 40:60%) to yield the title compound as a white solid.

Intermediate 13

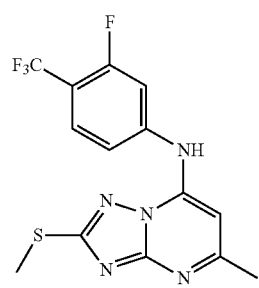

$^1$H NMR (300 MHz, $CDCl_3$) δ ppm: 8.05-7.83 (br, 1H), 7.75-7.71 (m, 1H), 7.27-7.21 (m, 2H), 6.53 (s, 1H), 2.73 (s, 3H), 2.60 (s, 3H); [ES+MS] m/z 358 (MH)$^+$.

Example 14

Synthesis of N-[3-fluoro-4-(trifluoromethyl)phenyl]-5-methyl-2-(methylsulfonyl)[1,2,4]triazolo[1,5-a]pyrimidin-7-amine (Intermediate 14)

To a suspension of N-[3-fluoro-4-(trifluoromethyl)phenyl]-5-methyl-2-(methylthio) [1,2,4]triazolo[1,5-a]pyrimidin-7-amine (0.35 g, 0.979 mmol) in acetic acid (5 mL), sodium tungstate dihydrate (10.99 mg, 0.033 mmol) was added at room temperature The reaction mixture was vigorously stirred and hydrogen peroxide (0.182 mL, 1.959 mmol) was added slowly at 40° C. The resulting mixture was then heated at 50° C. for 5 h, and then at room temperature overnight. The excess hydrogen peroxide was destroyed by the addition of an aqueous solution of sodium sulfite, product being extracted with DCM several times. The combined organic layers were washed with brine, dried over anhydrous $Na_2SO_4$ and solvent was evaporated under reduced pressure. The crude mixture was purified by flash chromatography (Si, eluting with Hexane/EtOAc mixtures from 95:5 to 0:100%) to yield the title compound as a white solid.

Intermediate 14

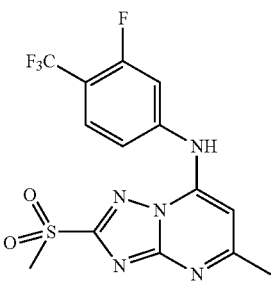

$^1$H NMR (300 MHz, $CDCl_3$) δ ppm: 8.37-8.18 (br s, 1H), 7.80-7.75 (m, 1H), 7.32-7.27 (m, 2H), 6.72 (s, 1H), 3.44 (s, 3H), 2.67 (s, 3H); [ES+MS] m/z 390 (MH)$^+$.

Example 15

Synthesis of 5-methyl-2-(methylthio)-N-[4-(trifluoromethyl)phenyl][1,2,4]triazolo[1,5-a]pyrimidin-7-amine (Intermediate 15)

To a suspension of 7-chloro-5-methyl-2-(methylthio)[1,2,4]triazolo[1,5-a]pyrimidine (Intermediate 8 (0.2 g, 0.932 mmol) in ethanol (5 mL), 4-(trifluoromethyl)aniline (ALDRICH, 0.117 mL, 0.932 mmol) was added and the mixture was stirred at room temperature for 3 h. Anhydrous ammonia (0.133 mL, 0.932 mmol) was added and solvent was removed in vacuo. The residue was purified by flash chromatography (Si, eluting with Hexane/EtOAc mixtures form 95:5 to 40:60%) to yield the title compound as a white solid.

Intermediate 15

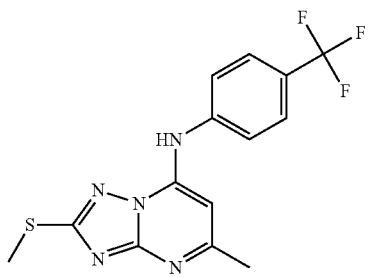

¹H NMR (300 MHz, DMSO-d₆) δ ppm: 10.33 (s, 1H), 7.81 (d, 2H), 7.67 (d, 2H), 6.62 (s, 1H), 2.68 (s, 3H), 2.42 (s, 3H); [ES+MS] m/z 340 (MH)⁺.

Example 16

Synthesis of 5-methyl-2-(methylsulfonyl)-N-[4-(trifluoromethyl)phenyl][1,2,4]triazolo[1,5-a]pyrimidin-7-amine (Intermediate 16)

To a suspension of 5-methyl-2-(methylthio)-N-[4-(trifluoromethyl)phenyl][1,2,4]triazolo[1,5-a]pyrimidin-7-amine (0.226 g, 0.666 mmol) in acetic acid (5 mL), sodium tungstate dihydrate (ALDRICH, 7.47 mg, 0.023 mmol) was added at room temperature. The reaction mixture was vigorously stirred and hydrogen peroxide (0.124 mL, 1.332 mmol) was added slowly at 40° C. The resulting mixture was then heated at 50° C. for 2 h. The excess hydrogen peroxide was destroyed by the addition of an aqueous solution of sodium sulfite, product being extracted with DCM several times. The combined organic layers were washed with brine, dried over anhydrous Na₂SO₄ and solvent was evaporated under reduced pressure. The crude mixture was purified by flash chromatography (Si, eluting with Hexane/EtOAC mixtures from 95:5 to 0:100%) to yield the title compound as a white solid.

Intermediate 16

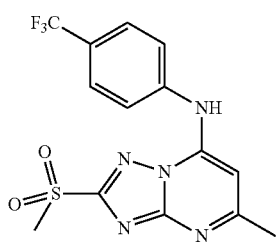

¹H NMR (300 MHz, CDCl₃) δ ppm: 8.18 (br s, 1H), 7.81-7.79 (m, 2H), 7.54-7.52 (m, 2H), 6.63 (s, 1H), 3.44 (s, 3H), 2.64 (s, 3H); [ES+MS] m/z 372 (MH)⁺.

Example 17

Synthesis of 5-methyl-2-(1-methylethyl)[1,2,4]triazolo[1,5-a]pyrimidin-7-ol (Intermediate 17)

A solution of Intermediate 1 (0.35 g, 2.497 mmol) and iso-butyryl chloride (FLUKA, 0.262 mL, 2.497 mmol) in a mixture of 1,4-dioxane (4 mL) and N,N-dimethylformamide (1 mL) was heated under reflux overnight. The reaction was then concentrated under vacuum and the residue was purified by flash chromatography (Si, eluting with DCM:MeOH mixtures, gradient from 100:0% to 90:10%) to yield the title compound as a white solid.

Intermediate 17

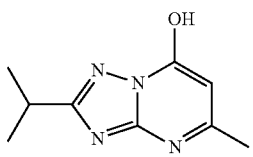

¹H NMR (300 MHz, DMSO-d₆) δ ppm: 13.21-12.82 (br, 1H), 5.76 (s, 1H), 3.01 (hept, 1H), 2.28 (s, 3H), 1.28 (d, 6H); [ES+MS] m/z 193 (MH)⁺.

Example 18

Synthesis of 7-chloro-5-methyl-2-(1-methylethyl)[1,2,4]triazolo[1,5-a]pyrimidine. (Intermediate 18)

A suspension of Intermediate 17 (0.225 g, 1.171 mmol) in phosphorous oxychloride (ALDRICH, 0.327 ml, 3.51 mmol) was heated under reflux for 1 h. The reaction mixture was added dropwise into iced water, neutralized with solid Na₂CO₃ and product was extracted with DCM. The combined organic layers were washed with brine and dried over anhydrous Na₂SO₄. A brown oil was obtained upon solvent removal in vacuo which was purified by flash chromatography (Si, eluting with Hexane:EtOAc mixtures from 100:0 to 40:60%) to yield the title compound as a white solid.

Intermediate 18

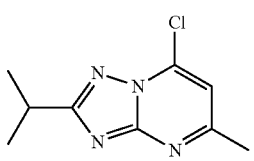

¹H NMR (300 MHz, CDCl₃) δ ppm: 7.01 (s, 1H), 3.35-3.25 (m, 1H), 2.68 (s, 3H), 1.45 (d, 6H); [ES+MS] m/z 211 (MH)⁺.

Example 19

Synthesis of 2-cyclopropyl-5-methyl[1,2,4]triazolo[1,5-a]pyrimidin-7-ol. (Intermediate 19)

To a solution of Intermediate 1 (0.5 g, 3.57 mmol) in a mixture of 1,4-dioxane (4 mL) and N,N-dimethylformamide (1 mL), cyclopropanecarbonyl chloride (ALDRICH, 0.49 mL, 5.35 mmol) was added and the resulting mixture was heated under reflux overnight. The reaction was then concentrated under vacuum yielding a pale yellow solid which was purified by flash chromatography (Si, eluting with DCM:MeOH mixtures, gradient from 100:0% to 90:10%) to yield a beige solid which was re-purified by flash chromatography (Si, eluting with DCM:MeOH mixtures from 100:0 to 85:15%). The title compound was obtained as a white solid.

Intermediate 19

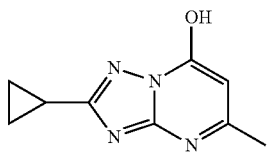

$^1$H NMR (300 MHz, DMSO-d$_6$) δ ppm: 13.17-12.81 (br, 1H), 5.75 (s, 1H), 2.27 (s, 3H), 2.07-2.00 (m, 1H), 1.02-0.97 (m, 2H), 0.90-0.86 (m, 2H); [ES+MS] m/z 191 (MH)$^+$.

Example 20

Synthesis of 7-chloro-2-cyclopropyl-5-methyl[1,2,4]triazolo[1,5-a]pyrimidine (Intermediate 20)

A suspension of Intermediate 19 (0.15 g, 0.789 mmol) in phosphorous oxychloride (ALDRICH, 1 ml, 10.73 mmol) was heated under reflux for 1 h. The reaction mixture was added dropwise into iced water, neutralized with solid Na$_2$CO$_3$ and product was extracted with DCM. The combined organic layers were washed with brine and dried over anhydrous Na$_2$SO$_4$. The crude mixture was purified by flash chromatography (Si, eluting with Hexane:EtOAc mixtures from 100:0 to 40:60%) to yield the title compound as a white solid.

Intermediate 20

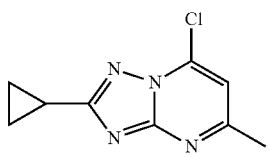

$^1$H NMR (300 MHz, CDCl$_3$) δ ppm: 6.97 (s, 1H), 2.66 (s, 3H), 2.28-2.22 (m, 1H), 1.26-1.22 (m, 2H), 1.15-1.10 (m, 2H); [ES+MS] m/z 209 (MH)$^+$.

2. Triazolopyrimidine Analogs

Scheme I shows a representative method for synthesizing compounds that belong to the triazolopyrimidine class, particularly, the synthesis of 5-Methyl-[1,2,4]triazolo[1,5-a]pyrimidin-7-yl)-(4-trifluoromethyl-phenyl)-amine.

Scheme I

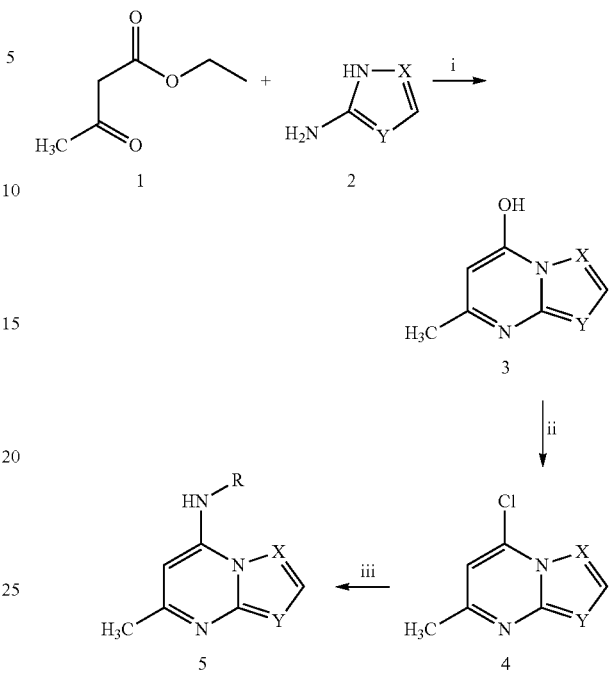

5 X = Y = N, R = appropriately substituted amine, e.g., p-trifluoromethylphenylamine Reagents and conditions: (i) AcOH, 3.5-20 h, reflux, 58-80%; (ii) POCl3, 30-90 min., reflux, 42-70%; (iii) RNH2, EtOH, 3-15 h, rt, 76-82%.

Compounds of the invention having a triazolopyrimidine scaffold were synthesized generally in accordance with Scheme I above. Thus, for instance, a mixture of 3-amino-1,2,4-triazole (2) (20 mmol) and ethyl acetoacetate (1) (20 mmol) was refluxed in acetic acid (10 ml) for 3.5-20 hours. Conversion of the 7-hydroxy group to a chloro group followed by the addition of an amine, such as 4-trifluoromethylphenylamine, gave the desired product. The resultant crude product was cooled to room temperature, filtered, washed with ethanol/water, and dried under vacuum to give a white solid. Yield 58-80%.

The synthesis of compounds with a trifluoromethyl substituent at C-3 position of the triazole ring proceeds in a similar manner. Scheme 2 graphically depicts the synthesis of these compounds.

Scheme 2

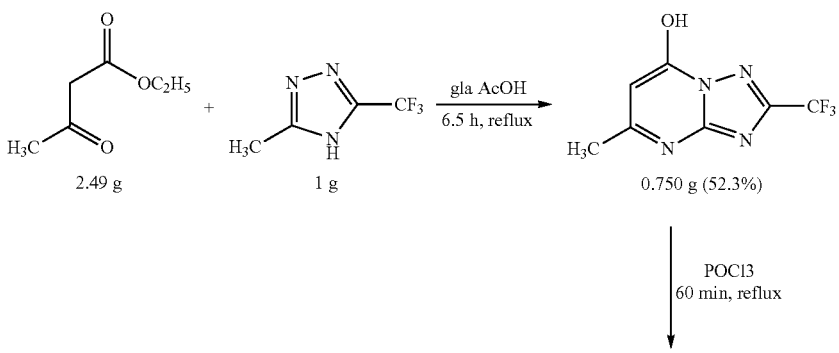

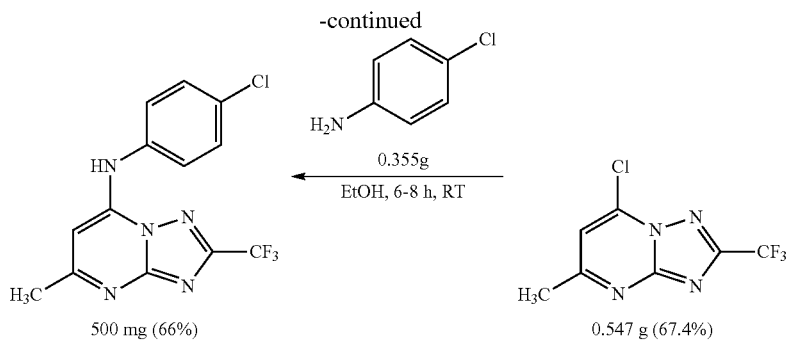

Example 21

Synthesis of 5-Methyl-2-(trifluoromethyl)-[1,2,4]triazolo[1,5-a]pyrimidin-7-ol

Step (A)

To a well-stirred solution of 5-(trifluoromethyl)-4H-1,2,4-triazol-3-amine (1 g, 6.58 mmol) in 15-20 mL glacial acetic acid, was added ethyl acetoacetate (2.57 g or 2.5 mL, 19.77 mmol) and the reaction mixture was refluxed for 6-6.5 h. Reaction progress was monitored by TLC. After completion, the reaction mixture was brought to room temperature and the excess glacial acetic acid was evaporated in vacuo. The light pinkish white solid, thus obtained, was filtered off, washed with dichloromethane and dried to yield 0.750 g (52.3%) of the titled compound.

Step (B) Synthesis of 7-chloro-5-methyl-2-(trifluoromethyl)-[1,2,4]triazolo[1,5-a]pyrimidine A mixture of 0.750 g (3.44 mmol) 5-methyl-2-(trifluoromethyl)-[1,2,4]triazolo[1,5-a]pyrimidin-7-ol and 1.35 mL (14.46 mmol) of phosphorus oxychloride was heated under reflux for 60 minutes, during which time the pinkish solid dissolved gradually with the evolution of hydrogen chloride gas. The resultant dark red solution was distilled under reduced pressure to remove excess phosphorus oxychloride and the residue triturated with ice-water. The resultant aqueous solution was extracted with methylene chloride, the organic layer thus obtained was dried and the solvent was removed to give the desired product. Further washes of the crude residue with methylene chloride gave 0.547 g of 7-chloro-5-methyl-2-(trifluoromethyl)-[1,2,4]triazolo[1,5-a]pyrimidine. Yield 67.4%. The washed crude was used without purification in the next step.

Step (C) Synthesis of N-(4-chlorophenyl)-5-methyl-2-(trifluoromethyl)-[1,2,4]triazolo[1,5-a]pyrimidin-7-amine 4-chloroaniline (0.355 g, 2.78 mmol) was added to a well-stirred absolute ethanol solution of 7-chloro-5-methyl-2-(trifluoromethyl)-[1,2,4]triazolo[1,5-a]pyrimidine (0.547 g, 2.32 mmol, 15-20 mL). After stirring for 6-8 hours at room temperature, the desired product crystallized and was then filtered. Subsequent purification using column chromatography gave the final product in 66% yield.

The synthetic procedures above were adapted to synthesize the following triazolopyrimidine compounds of the invention:

Example 22

Synthesis of 5-Methyl-2-(trifluoromethyl)-N-(4-(pentafluorosulfur)phenyl)-[1,2,4]triazolo[1,5-a]pyrimidin-7-amine

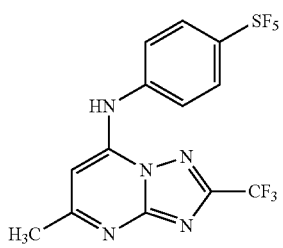

$^1$H NMR (300 MHz, MeOD-d$_4$): δ 7.70 (m, 5H), 2.70 (s, 3H). MS m/z 420.0.

Example 23

Synthesis of N-(2,3-Dihydro-1H-inden-2-yl)-5-methyl-[1,2,4]triazolo[1,5-a]pyrimidin-7-amine

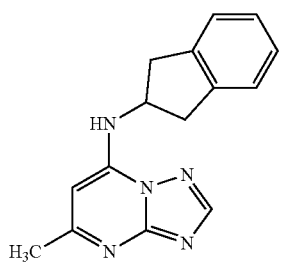 [SMILES: Cc1cc(NC2Cc3ccccc3C2)n2ncnc2n1]

Mp 192° C. $^1$H NMR (300 MHz, CDCl$_3$): δ 8.25 (s, 1H), 7.30-7.24 (m, 4H), 6.14 (brs, NH, exchangeable), 6.13 (s, 1H), 4.38 (m, 1H), 3.56-3.47 (m, 2H), 3.14-3.07 (m, 2H), 2.62 (s, 3H). MS m/z 266.1 [M+H]$^+$.

Example 24

Synthesis of 5-Methyl-N-(1,2,3,4-tetrahydronaphthalen-2-yl)-[1,2,4]triazolo[1,5-a]pyrimidin-7-amine

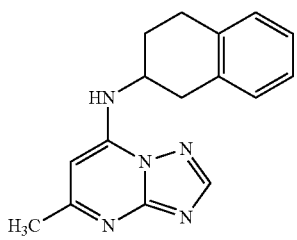 [SMILES: Cc1cc(NC2CCc3ccccc3C2)n2ncnc2n1]

Mp 57° C. $^1$H NMR (300 MHz, CDCl$_3$): δ 8.28 (s, 1H), 7.24-7.08 (m, 4H), 6.17 (brs, NH, exchangeable), 6.12 (s, 1H), 4.04 (m, 1H), 3.39-3.25 (m, 1H), 3.08-2.87 (m, 3H), 2.62 (s, 3H), 2.38-2.24 (m, 1H), 2.10-1.92 (m, 1H). MS m/z 280.2 [M+H]$^+$.

Example 25

Synthesis of 5-Methyl-N-(4-(2,2,2-trifluoroethyl)phenyl)-[1,2,4]triazolo[1,5-a]pyrimidin-7-amine

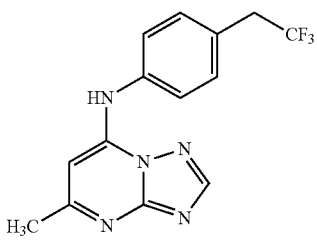 [SMILES: Cc1cc(Nc2ccc(CC(F)(F)F)cc2)n2ncnc2n1]

Mp 204° C. $^1$H NMR (300 MHz, DMSO-d$_6$): δ 10.24 (brs, NH, exchangeable), 8.51 (s, 1H), 7.50-7.43 (m, 4H), 6.44 (s, 1H), 3.76-3.64 (m, 1H), 2.43 (s, 3H). MS m/z 308.2 [M+H]$^+$.

Example 26

Synthesis of N-(4-Chloro-3-fluorophenyl)-5-methyl-[1,2,4]triazolo[1,5-a]pyrimidin-7-amine

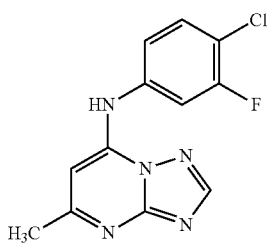 [SMILES: Cc1cc(Nc2ccc(Cl)c(F)c2)n2ncnc2n1]

Mp 285° C. $^1$H NMR (300 MHz, DMSO-d$_6$): δ 10.38 (brs, NH, exchangeable), 8.52 (s, 1H), 7.70-7.65 (m, 1H), 7.58-7.55 (m, 1H), 7.38-7.35 (m, 1H), 6.62 (s, 1H), 2.45 (s, 3H). MS m/z 278.2 [M+H]$^+$.

Example 27

Synthesis of 5-Methyl-N-(4-(trifluoromethylthio)phenyl)-[1,2,4]triazolo[1,5-a]pyrimidin-7-amine

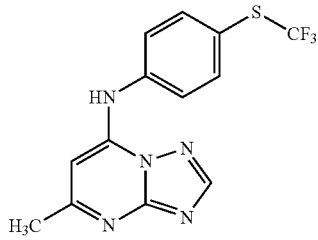 [SMILES: Cc1cc(Nc2ccc(SC(F)(F)F)cc2)n2ncnc2n1]

Mp 236° C. $^1$H NMR (300 MHz, DMSO-d$_6$): δ 10.45 (brs, NH, exchangeable), 8.52 (s, 1H), 7.85-7.79 (m, 2H), 7.65-7.57 (m, 2H), 6.64 (s, 1H), 2.48 (s, 3H). MS m/z 326.2 [M+H]$^+$.

Example 28

Synthesis of N-(5-Fluoro-2,3-dihydro-1H-inden-2-yl)-5-methyl-[1,2,4]triazolo[1,5-a]pyrimidin-7-amine

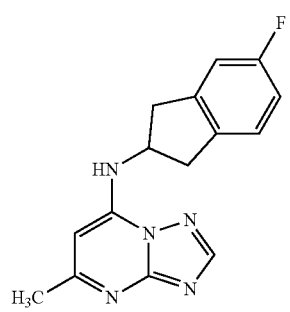 [SMILES: Cc1cc(NC2Cc3ccc(F)cc3C2)n2ncnc2n1]

Mp 216° C. $^1$H NMR (300 MHz, DMSO-d$_6$): δ 8.40 (brs, NH, exchangeable), 8.38 (s, 1H), 7.25-7.20 (m, 1H), 7.12-7.05 (m, 1H), 7.04-6.97 (m, 1H), 6.52 (s, 1H), 4.62-4.55 (m, 1H), 3.34-3.32 (m, 2H), 3.12-3.05 (m, 2H), 2.46 (s, 3H). MS m/z 284.2 [M+H]$^+$.

Example 29

Synthesis of N-(5,6-Dimethoxy-2,3-dihydro-1H-inden-2-yl)-5-methyl-[1,2,4]triazolo[1,5-a]pyrimidin-7-amine

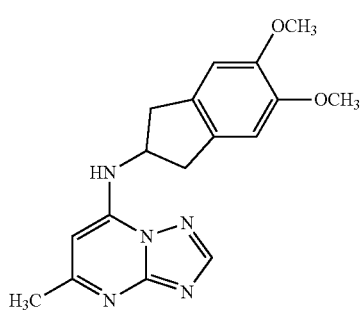 [SMILES: COc1cc2c(cc1OC)CC(Nc1cc(C)nc3ncnn13)C2]

Mp 191° C. ¹H NMR (300 MHz, DMSO-d₆): δ 8.38 (s, 1H), 8.36 (brs, NH, exchangeable), 6.88-6.85 (m, 2H), 6.52 (s, 1H), 4.62-4.52 (m, 1H), 3.72 (s, 6H), 3.30-3.20 (m, 2H), 3.12-3.02 (m, 2H), 2.45 (s, 3H). MS m/z 326.3 [M+H]⁺.

Example 30

Synthesis of N-(5-Bromo-2,3-dihydro-1H-inden-2-yl)-5-methyl-[1,2,4]triazolo[1,5-a]pyrimidin-7-amine

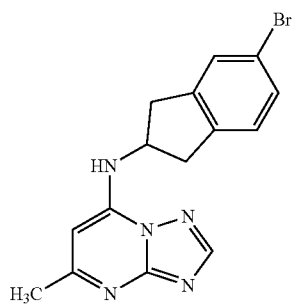 [SMILES: Cc1cc(NC2Cc3ccc(Br)cc3C2)n2ncnc2n1]

Mp 164° C. ¹H NMR (300 MHz, CDCl₃): δ 8.25 (s, 1H), 7.43 (m, 1H), 7.39-7.36 (m, 1H), 7.17-7.14 (m, 1H), 6.28 (brs, NH, exchangeable), 6.12 (s, 1H), 4.59-4.49 (m, 1H), 3.54-3.42 (m, 2H), 3.22-3.01 (m, 2H), 2.62 (s, 3H). MS m/z 346 [M+2]⁺.

Example 31

Synthesis of 2-ethyl-5-methyl-N-[4-(pentafluoro-λ⁶-sulfanyl)phenyl][1,2,4]triazolo[1,5-a]pyrimidin-7-amine A suspension of Intermediate 5 (80 mg, 0.407 mmol) and 4-aminophenylsulfur pentafluoride (MANCHESTER, 89 mg, 0.407 mmol) in ethanol (5 mL) was heated at 50° C. for 1 h, starting material dissolving during the process. The reaction mixture was concentrated under vacuum, redissolved in DCM (20 mL) and washed with aq. Na₂CO₃ (2×15 mL). The organic layer was dried over anhydrous Na₂SO₄, filtered and concentrated under vacuum to afford the title compound as a white solid.

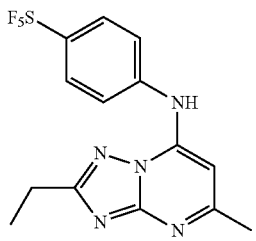

¹H NMR (400 MHz, DMSO-d₆) δ ppm: 10.44 (bs, 1H), 7.95 (d, 2H), 7.66 (d, 2H), 6.68 (s, 1H), 2.83 (q, 2H), 2.43 (s, 3H), 1.32 (t, 3H); [ES+MS] m/z 380 (MH)⁺.

Example 32

Synthesis of 2-(ethyloxy)-5-methyl-N-[4-(pentafluoro-λ⁶-sulfanyl)phenyl][1,2,4]triazolo[1,5-a]pyrimidin-7-amine Intermediate 10 (0.15 g, 0.349 mmol) was added to sodium ethoxide (ALDRICH, 0.071 g, 1.048 mmol) in ethanol (3 mL). The mixture was heated under microwave irradiation at 120° C. for 30 minutes. Solvent was removed under vacuum and the crude mixture was purified by flash chromatography (Si, eluting with DCM: MeOH mixtures from 100:0 to 90:10%). The title compound was obtained as a white solid.

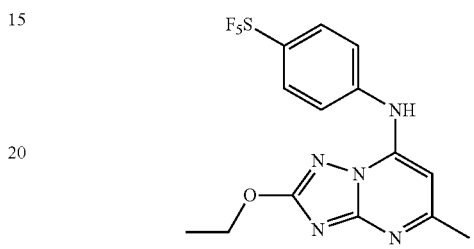

¹H NMR (300 MHz, CDCl₃) δ ppm: 7.91-7.85 (m, 2H), 7.82-7.76 (br, 1H), 7.43 (d, 2H), 6.51 (s, 1H), 4.56 (q, 2H), 2.56 (s, 3H), 1.49 (t, 3H); [ES+MS] m/z 396 (MH)⁺.

Example 33

Synthesis of N-[3,5-difluoro-4-(trifluoromethyl)phenyl]-2-(ethyloxy)-5-methyl[1,2,4]triazolo[1,5-a]pyrimidin-7-amine Intermediate 12 (0.29 g, 0.712 mmol) was added to sodium ethoxide (ALDRICH, 0.145 g, 2.136 mmol) in ethanol (5 mL). The mixture was heated under microwave irradiation at 120° C. for 30 minutes. Solvent was removed under vacuum and the crude mixture was purified by flash chromatography (Si, eluting Hexane/EtOAc mixtures from 90:10 to 0:100%) to yield the title compound as a white solid.

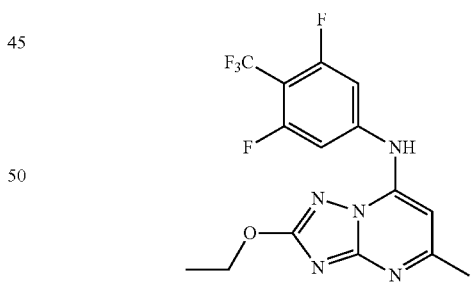

¹H NMR (300 MHz, CDCl₃) δ ppm: 8.08-7.76 (br, 1H), 7.02-7.00 (m, 2H), 6.60 (s, 1H), 4.55 (q, 2H), 2.61 (s, 3H), 1.49 (t, 3H); [ES+MS] m/z 374 (MH)⁺.

Example 34

Synthesis of 2-(ethyloxy)-N-[3-fluoro-4-(trifluoromethyl)phenyl]-5-methyl[1,2,4]triazolo[1,5-a]pyrimidin-7-amine Intermediate 14 (0.19 g, 0.488 mmol) was added to sodium ethoxide (ALDRICH, 0.1 g, 1.464 mmol) in ethanol (4 mL).

The mixture was heated under microwave irradiation at 120° C. for 30 minutes and solvent was removed under vacuum to yield a yellowish residue. The crude mixture was purified by flash chromatography (Si, eluting with Hexane/EtOAc mixtures from 90:10 to 0:100%) to yield the title compound as a white solid.

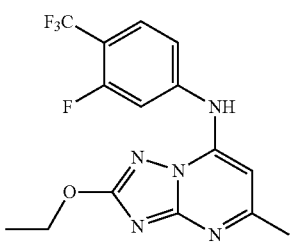 [SMILES: CCOc1nc2nc(C)cc(Nc3ccc(C(F)(F)F)c(F)c3)n2n1]

¹H NMR (300 MHz, CDCl₃) δ ppm: 8.01-7.75 (br, 1H), 7.75-7.69 (m, 1H), 7.25-7.18 (m, 2H), 6.54 (s, 1H), 4.55 (q, 2H), 2.58 (s, 3H), 1.48 (t, 3H); [ES+MS] m/z 356 (MH)⁺.

Example 35

Synthesis of 2-(ethyloxy)-5-methyl-N-[4-(trifluoromethyl)phenyl][1,2,4]triazolo[1,5-a]pyrimidin-7-amine Intermediate 16 (0.14 g, 0.377 mmol) was added to sodium ethoxide (ALDRICH, 0.077 g, 1.131 mmol) in ethanol (3 mL). The mixture was heated under microwave irradiation at 120° C. for 30 minutes. Solvent was removed under vacuum to yield a yellowish residue which was purified by flash chromatography (Si, eluting with a 90:10% DCM: MeOH mixture) to yield the title compound as a beige solid.

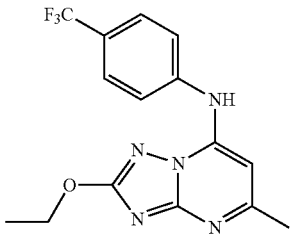 [SMILES: CCOc1nc2nc(C)cc(Nc3ccc(C(F)(F)F)cc3)n2n1]

¹H NMR (300 MHz, CDCl₃) δ ppm: 7.79-7.71 (br, 3H), 7.46 (d, 2H), 6.47 (s, 1H), 4.56 (q, 2H), 2.55 (s, 3H), 1.49 (t, 3H); [ES+MS] m/z 338 (MH)⁺.

Example 36

Synthesis of 5-methyl-2-(1-methylethyl)-N-[4-(trifluoromethyl)phenyl][1,2,4]triazolo[1,5-a]pyrimidin-7-amine To a suspension of Intermediate 18 (0.042 g, 0.199 mmol) in ethanol (5 mL), 4-(trifluoromethyl)aniline (ALDRICH, 0.025 mL, 0.199 mmol) was added and the mixture was stirred at room temperature overnight. Solvent was removed in vacuo and the crude mixture was purified by flash chromatography (Si, eluting with Hexane/EtOAc mixtures from 75:25 to 25:75%) to yield the title compound as a white solid.

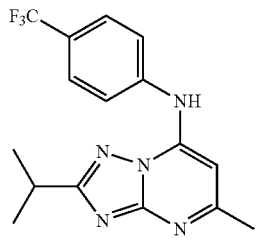

¹H NMR (300 MHz, CDCl₃) δ ppm: 8.00-7.86 (br, 1H), 7.77 (d, 2H), 7.50 (d, 2H), 6.47 (s, 1H), 3.32-3.22 (m, 1H), 2.58 (s, 3H), 1.46 (d, 6H); [ES+MS] m/z 336 (MH)⁺.

Example 37

Synthesis of 5-methyl-2-(1-methylethyl)-N-[4-(pentafluoro-λ⁶-sulfanyl)phenyl][1,2,4]triazolo[1,5-a]pyrimidin-7-amine To a suspension of Intermediate 18 (0.042 g, 0.199 mmol) in ethanol (5 mL), 4-aminophenylsulfur pentafluoride (MANCHESTER, 0.044 g, 0.199 mmol) was added and the mixture was stirred at room temperature overnight. Solvent was removed in vacuo and the crude mixture was purified by flash chromatography (Si, eluting with Hexane/EtOAc mixtures from 75:25 to 25:75%) to yield the title compound as a white solid.

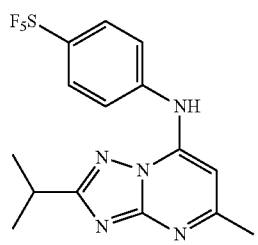

¹H NMR (300 MHz, CDCl₃) δ ppm: 7.96-7.83 (br, 3H), 7.47 (d, 2H), 6.50 (s, 1H), 3.25 (hept, 1H), 2.58 (s, 3H), 1.45 (d, 6H); [ES+MS] m/z 394 (MH)⁺.

Example 38

Synthesis of 2-cyclopropyl-5-methyl-N-[4-(trifluoromethyl)phenyl][1,2,4]triazolo[1,5-a]pyrimidin-7-amine To a suspension of Intermediate 20 (0.04 g, 0.192 mmol) in ethanol (2.5 mL), 4-(trifluoromethyl)aniline (ALDRICH, 0.031 g, 0.192 mmol) was added and the mixture was stirred under reflux for 2 h. Solvent was removed in vacuo and the crude mixture was purified by preparative HPLC (SunFire 19×150 mm, H₂O 0.1% TFA-ACN 0.1% TFA gradient from 10 to 100%) to yield a beige solid which was further purified by preparative HPLC (SunFire 19×150 mm, H₂O 0.1% TFA-ACN 0.1% TFA gradient from 30 to 100%) to yield the title compound as a white solid.

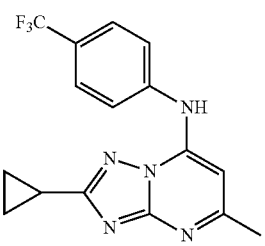 [SMILES: Cc1cc(Nc2ccc(C(F)(F)F)cc2)n2nc(C3CC3)nc2n1]

¹H NMR (300 MHz, DMSO-d₆) δ ppm: 10.79-10.36 (br, 1H), 7.82 (d, 2H), 7.67 (d, 2H), 6.62 (s, 1H), 2.42 (s, 3H), 2.21-2.14 (m, 1H), 1.11-1.01 (m, 4H); [ES+MS] m/z 334 (MH)⁺.

Example 39

Example 15: Synthesis of 2-cyclopropyl-5-methyl-N-[4-(pentafluoro-λ⁶-sulfanyl)phenyl][1,2,4]triazolo[1,5-a]pyrimidin-7-amine To a suspension of Intermediate 20 (0.04 g, 0.192 mmol) in ethanol (2.5 mL), 4-aminophenylsulfur pentafluoride (MANCHESTER, 0.042 g, 0.192 mmol) was added and the mixture was stirred under reflux overnight. Solvent was removed in vacuo and the crude mixture was purified by preparative HPLC (SunFire 19×150 mm, H₂O 0.1% TFA-ACN 0.1% TFA gradient from 10 to 100%) to yield the title compound as a beige solid.

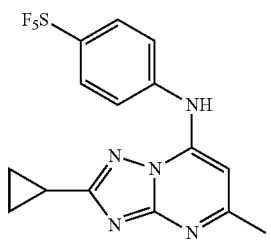

¹H NMR (300 MHz, DMSO-d₆) δ ppm: 10.89-10.35 (br, 1H), 8.01-7.95 (m, 2H), 7.69-7.63 (m, 2H), 6.69 (s, 1H), 2.43 (s, 3H), 2.20-2.14 (m, 1H), 1.10-1.01 (m, 4H); [ES+MS] m/z 392 (MH)⁺.

Example 40

Synthesis of 2-(trifluoromethyl)-N-(4-(trifluoromethyl)phenyl)-5-methyl-[1,2,4]triazolo[1,5-a]pyrimidin-7-amine

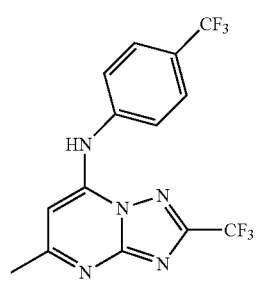 [SMILES: Cc1cc(Nc2ccc(C(F)(F)F)cc2)n2nc(C(F)(F)F)nc2n1]

Mp: 124-126° C.; ¹H NMR (300 MHz, CDCl₃): δ 7.93 (brs, NH, exchangeable), 7.82 (d, J=8.1 Hz, 2H), 7.54 (d, J=8.7 Hz, 2H), 6.61 (s, 1H), 2.65 (s, 3H). MS m/z 362.3 [M+H]⁺.

Example 41

Synthesis of 2-(trifluoromethyl)-N-(4-(sulfurpentafluoro)phenyl)-5-methyl-[1,2,4]triazolo[1,5-a]pyrimidin-7-amine

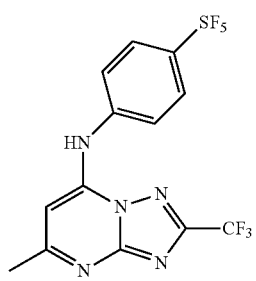

Mp: 178-180° C. ¹H NMR (300 MHz, CDCl₃): δ 10.79 (brs, NH, exchangeable), 8.01 (d, J=8.9 Hz, 2H), 7.70 (d, J=9.2 Hz, 2H), 6.90 (s, 1H), 2.51 (s, 3H). MS m/z 420.3 [M+H]⁺.

Example 42

Synthesis of N-(3,5-difluoro-4-(trifluoromethyl)phenyl)-2-(trifluoromethyl)-5-methyl-[1,2,4]triazolo[1,5-a]pyrimidin-7-amine

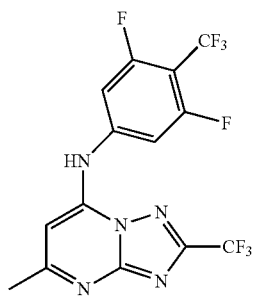 [SMILES: Cc1cc(Nc2cc(F)c(C(F)(F)F)c(F)c2)n2nc(C(F)(F)F)nc2n1]

Mp: 86-88° C.; ¹H NMR (300 MHz, CDCl₃): δ 8.29 (brs, NH, exchangeable), 7.14 (d, J=9.7 Hz, 2H), 6.77 (s, 1H), 2.70 (s, 3H). MS m/z 398.2 [M+H]⁺.

Example 43

Synthesis of 7-Amino substituted 2-(difluoroethyl)-5-methyl-[1,2,4]triazolo[1,5-a]pyrimidine compounds were prepared as illustrated in Scheme 3

Scheme 3

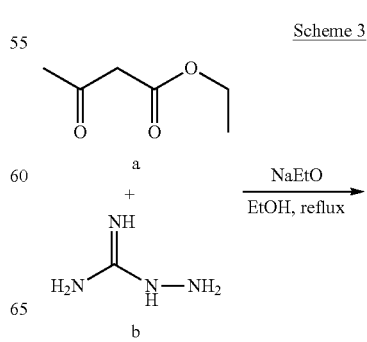

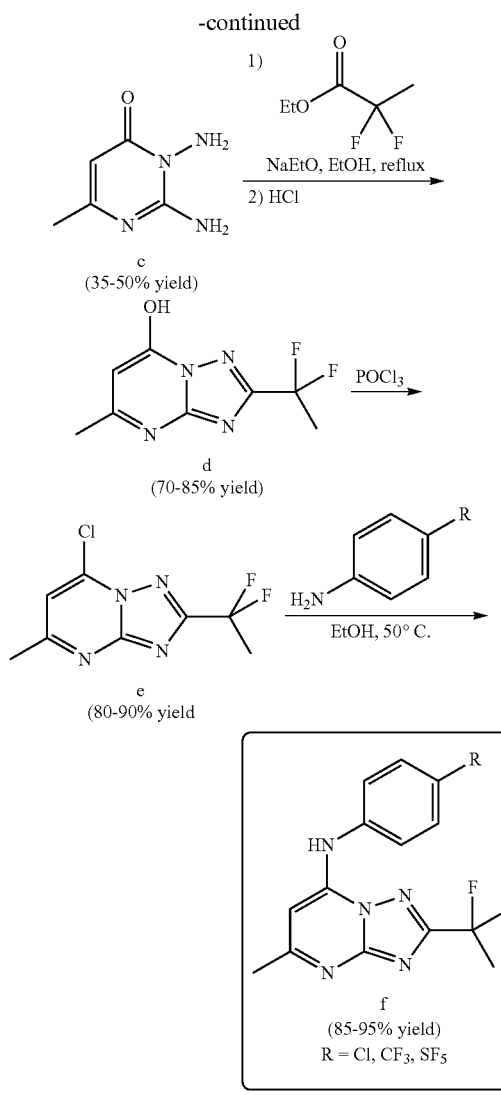

This methodology was used to synthesize inventive compounds having a difluoroethyl group at position C-3.

Example 44

Synthesis of 2-(1,1-difluoroethyl)-5-methyl-N-[4-(pentafluoro-λ⁶-sulfanyl)phenyl][1,2,4]triazolo[1,5-a]pyrimidin-7-amine A suspension of Intermediate 3 (5.84 g, 25.09 mmol) and 4-aminophenylsulfur pentafluoride (MANCHESTER, 5.5 g, 25.09 mmol) in ethanol (150 mL) was heated at 50° C. for 1 h. Heating resulted in the precipitation of a solid. The reaction mixture was concentrated under vacuum, redissolved in DCM (300 mL) and washed with aq. Na₂CO₃ (2×350 mL). The organic layer was dried over Na₂SO₄ and filtered. Then 8 g of silica gel were added and the mixture was concentrated under vacuum to dryness. The residue was purified (silica gel column, eluting with Hexane/EtOAc mixtures from 100:0 to 50:50%) to afford the title compound as a white solid.

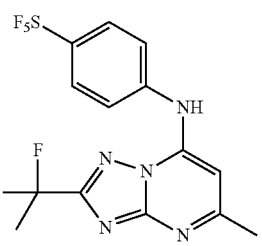

$^1$H NMR (400 MHz, DMSO-d$_6$) δ ppm: 10.60 (bs, 1H), 7.97 (d, 2H), 7.67 (d, 2H), 6.79 (s, 1H), 2.47 (s, 3H), 2.13 (t, 3H); [ES+MS] m/z 416 (MH)$^+$.

Example 45

Synthesis of 2-(1,1-difluoroethyl)-5-methyl-N-[4-(trifluoromethyl)phenyl][1,2,4]triazolo[1,5-a]pyrimidin-7-amine To a suspension of Intermediate 3 (10 g, 43 mmol) in ethanol (150 mL), 4-(trifluoromethyl)aniline (ALDRICH, 6.93 g, 43 mmol) was added and the mixture was stirred at room temperature for 1 h. 7M Ammonia in MeOH (6.14 mL, 43 mmol) was added to neutralize the hydrochloride salt and solvent was removed in vacuo. The crude mixture was purified by flash chromatography (Si, eluting with Hexane/EtOAc mixtures from 95:5 to 40:60%) to yield the title compound as a yellow solid.

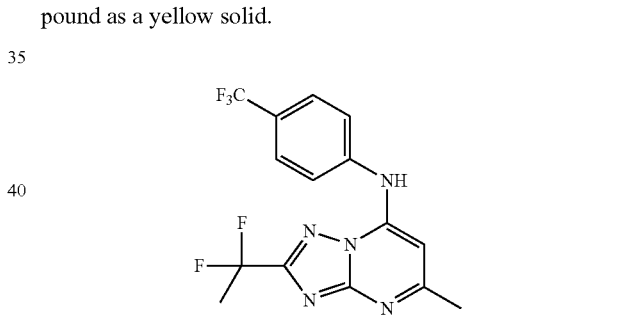

$^1$H NMR (300 MHz, DMSO-d$_6$) δ ppm: 10.58 (s, 1H), 7.83 (d, 2H), 7.70 (d, 2H), 6.73 (s, 1H), 2.47 (s, 3H), 2.14 (t, 3H); [ES+MS] m/z 358 (MH)$^+$.

Example 46

Synthesis of 2-(1,1-difluoroethyl)-N-[3-fluoro-4-(trifluoromethyl)phenyl]-5-methyl[1,2,4]triazolo[1,5-a]pyrimidin-7-amine A suspension of Intermediate 3 (0.1 g, 0.43 mmol) and 3-fluoro-4-(trifluoromethyl)aniline (ALFAAESAR, 0.077 g, 0.43 mmol) in ethanol (5 mL) was heated at 50° C. for 1 h. The reaction mixture was concentrated under vacuum, redissolved in DCM (20 mL) and washed with aq. Na₂CO₃ (2×15 mL). The organic layer was dried over anhydrous Na₂SO₄ filtered and concentrated under vacuum to afford a white solid.

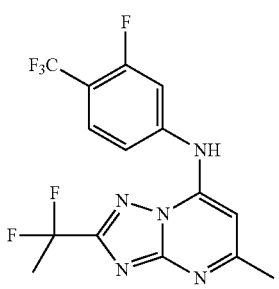 [SMILES: Cc1cc(Nc2ccc(C(F)(F)F)c(F)c2)n2nc(C(C)(F)F)nc2n1]

¹H NMR (400 MHz, DMSO-d₆) δ ppm: 10.69 (bs, 1H), 7.84 (m, 1H), 7.63-7.45 (m, 2H), 6.91 (s, 1H), 2.50-2.48 (pr, 3H), 2.13 (t, J=19.2 Hz, 3H); [ES+MS] m/z 376 (MH)⁺.

Example 47

Synthesis of 2-(1,1-difluoroethyl)-N-[3,5-difluoro-4-(trifluoromethyl)phenyl]-5-methyl[1,2,4]triazolo[1,5-a]pyrimidin-7-amine A solution of Intermediate 3 (0.1 g, 0.43 mmol) and 4-amino-2,6-difluorobenzotrifluoride (FLUOROCHEM, 0.085 g, 0.43 mmol) in ethanol (7 mL) was stirred at room temperature overnight. Solvent was removed in vacuo and the residue was taken up in DCM. The resulting solution was washed with 1N Na₂CO₃, then with brine and dried over anhydrous Na₂SO₄ to yield a yellow oil which was purified by flash chromatography (Si, eluting with Hexane/EtOAc mixtures from 100:0 to 50:50%) to afford the title compound as a pale yellow solid.

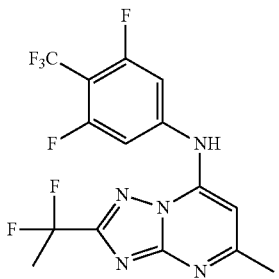 [SMILES: Cc1cc(Nc2cc(F)c(C(F)(F)F)c(F)c2)n2nc(C(C)(F)F)nc2n1]

¹H NMR (300 MHz, DMSO-d₆) δ ppm: 10.91-10.74 (br, 1H), 7.54-7.38 (br, 2H), 7.16-7.00 (br, 1H), 2.55-2.49 (br, 3H), 2.13 (t, 3H); ¹H NMR (300 MHz, CDCl₃) δ ppm: 8.33-8.04 (br, 1H), 7.08 (d, 2H), 6.71 (s, 1H), 2.68 (s, 3H), 2.17 (t, 3H); [ES+MS] m/z 394 (MH)⁺.

Example 48

Synthesis of 2-(1,1-difluoropropyl)-5-methyl-N-[4-(trifluoromethyl)phenyl][1,2,4]triazolo[1,5-a]pyrimidin-7-amine A suspension of Intermediate 7 (0.1 g, 0.405 mmol) and 4-(trifluoromethyl)aniline (ALDRICH, 0.051 mL, 0.405 mmol) in ethanol (5 mL) was heated at 50° C. for 1 h. The reaction mixture was concentrated under vacuum, redissolved in DCM (20 mL) and washed with aq. Na₂CO₃ (2×15 mL). The organic layer was dried over anhydrous Na₂SO₄, filtered and concentrated under vacuum to afford a white solid.

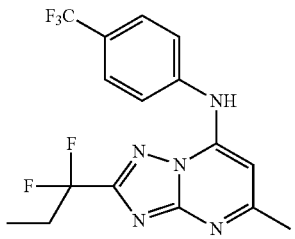 [SMILES: CCC(F)(F)c1nc2nc(C)cc(Nc3ccc(C(F)(F)F)cc3)n2n1]

¹H NMR (400 MHz, DMSO-d₆) δ ppm: 10.58 (br s, 1H), 7.82 (d, 2H), 7.67 (d, 2H), 6.69 (s, 1H), 2.45 (s, 3H), 2.43-2.37 (m, 2H), 1.02 (t, 3H); [ES+MS] m/z 372 (MH)⁺.

Example 49

Synthesis of 2-(1,1-difluoropropyl)-5-methyl-N-[4-(pentafluoro-λ⁶-sulfanyl)phenyl][1,2,4]triazolo[1,5-a]pyrimidin-7-amine A suspension of Intermediate 7 (0.1 g, 0.405 mmol) and 4-aminophenylsulfur pentafluoride (MANCHESTER, 0.089 g, 0.405 mmol) in ethanol (5 mL) was heated at 50° C. for 1 h. The reaction mixture was concentrated under vacuum, redissolved in DCM (20 mL) and washed with aq. Na₂CO₃ (2×15 mL). The organic layer was dried over anhydrous Na₂SO₄, filtered and concentrated under vacuum to afford a white solid.

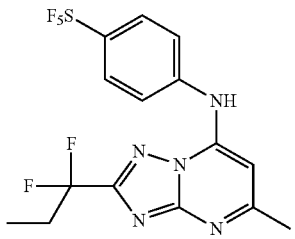

¹H NMR (400 MHz, DMSO-d₆) δ ppm: 10.63 (br s, 1H), 7.97 (d, 2H), 7.67 (d, 2H), 6.78 (s, 1H), 2.47 (s, 3H), 2.45-2.37 (m, 2H), 1.02 (t, 3H); [ES+MS] m/z 430 (MH)⁺.

3. Imidazo[1,2-a]pyrimidin-5-yl Compounds

Scheme 4 below illustrates a protocol for synthesizing imidazo[1,2-a]pyrimidin-5- compounds of the invention.

Scheme 4:

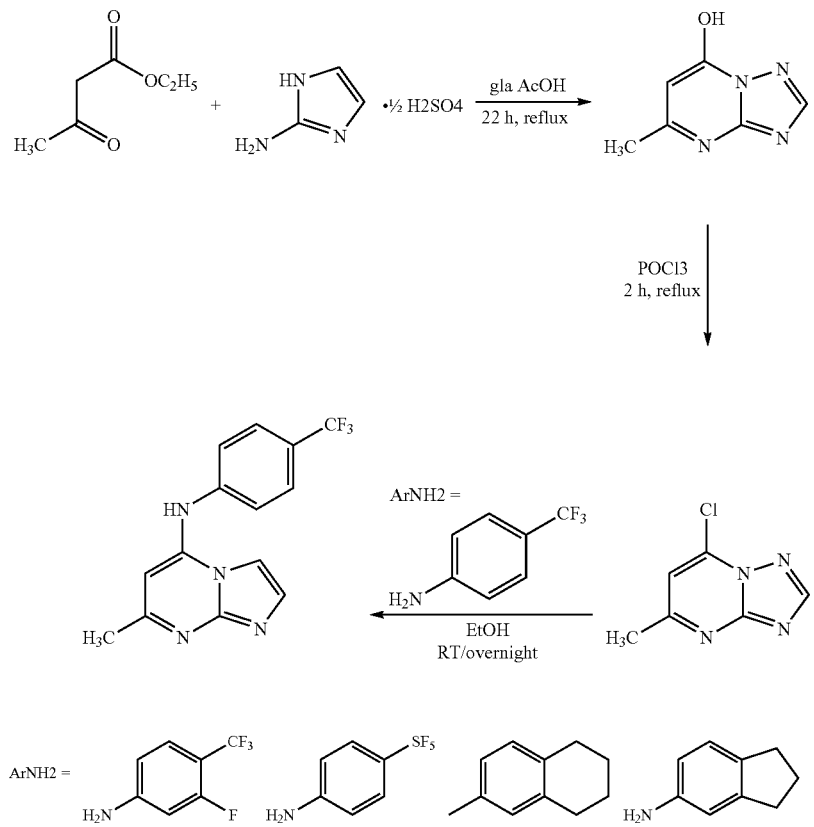

The synthesis of imidazopyrimidine compounds was achieved by reacting an appropriately substituted 2-aminoimidazole with ethyl acetoacetate, followed by chlorination and reaction of the resultant 5-chloro compound with an appropriate amine. An exemplary synthesis is given below for 7-methyl-N-(4-(trifluoromethyl)phenyl)imidazo[1,2-a]pyrimidin-5-amine.

Example 50

Synthesis of 7-methyl-N-(4-(trifluoromethyl)phenyl)imidazo[1,2-a]pyrimidin-5-amine Step (A) Synthesis of 7-Methylimidazo[1,2-a]pyrimidin-5-ol A solution of 1 g (7.58 mmol) 2-aminoimidazole hemisulfate, 1.19 g (9.15 mmol) of ethyl acetoacetate and 15 mL of glacial acetic acid was refluxed for 20-22 hours. Upon completion of the reaction, the mixture is cooled and the solvent is removed in vacuo to give a brownish solid. The brown residue was filtered, washed with methylene chloride and dried under vacuum to give the titled product. Yield 79% (0.893 g).

Step (B) Synthesis of 5-chloro-7-methylimidazo[1,2-a]pyrimidine

A mixture of 0.893 g (5.99 mmol) 7-Methylimidazo[1,2-a]pyrimidin-5-ol and 17 mL (182.1 mmol) of phosphorus oxychloride were refluxed for two hours. At the end of the reflux, a clear red solution is obtained, which is rotovaped to remove excess phosphorus oxychloride. The residue thus obtained was titurated with methylene chloride followed by filtration of the slurry to isolate the desired compound as a solid. Further washes with methylene chloride followed by drying of the solid under reduced pressure resulted in the chlorinated product. Yield 522 mg (52% yield).

Step (C) Synthesis of 7-methyl-N-(4-(trifluoromethyl)phenyl)imidazo[1,2-a]pyrimidin-5-amine 4-(trifluoromethyl)aniline (602 mg, 3.74 mmol) was added to the stirred solution of 5-chloro-7-methylimidazo[1,2-a]pyrimidine (522 mg, 3.12 mmol) in excess of absolute ethanol. The reaction mixture was heated intermittently to maintain homogeneity (clear) of the reaction mixture. After stirring overnight at room temperature, the excess ethanol was removed in vacuo and the resultant crude was purified using column chromatography. Yield 0.593 mg (65% yield).

The following compounds were synthesized according to a procedure analogous to that shown above in Scheme 4.

Example 51

Synthesis of N-(3-fluoro-4-(trifluoromethyl)phenyl)-7-methylimidazo[1,2-a]pyrimidin-5-amine Mp: 302-304° C. $^1$H NMR (300 MHz, MeOD-$d_4$): δ 7.84 (s, 1H), 7.73 (m, 1H), 7.51 (s, 1H), 7.22 (m, 2H), 6.28 (s, 1H), 2.43 (s, 3H). MS m/z 311.2 (M+H$^+$).

Example 52

7-Methyl-N-(4-(pentafluorosulfur)phenyl)imidazo[1,2-a]pyrimidin-5-amine

Mp 260-261° C. $^1$H NMR (300 MHz, dmso-$d_6$): δ 7.85 (m, 2H), 7.75 (s, 1H), 7.39 (s, 1H), 7.25 (m, 2H), 2.09 (s, 3H). MS m/z 351.0 (M+H$^+$).

Example 53

Synthesis of 7-Methyl-N-(5,6,7,8-tetrahydronaphthalen-2-yl)imidazo[1,2-a]pyrimidin-5-amine Mp 264-266° C. $^1$H NMR (300 MHz, MeOD-$d_4$): δ 7.85 (s, 1H), 7.55 (s, 1H), 7.14 (m, 3H), 6.96 (s, 1H), 2.82 (s, 4H), 2.41 (s, 3H), 1.86 (s, 4H). MS m/z 279.0.

Example 54

Synthesis of N-(2,3-dihydro-1H-inden-5-yl)-7-methylimidazo[1,2-a]pyrimidin-5-amine Mp 255-257° C. $^1$H NMR (300 MHz, dmso-$d_6$): δ 9.32 (brs, NH), 7.97 (s, 1H), 7.53 (s, 1H), 7.24 (m, 3H), 6.00 (s, 1H), 2.90 (m, 4H), 2.31 (s, 3H), 2.01 (m, 2H). MS m/z 265.0.

Biological Evaluation

As stated above, DHOD plays an important role in malaria. Described here are assays useful for testing the inhibition of DHOD by compounds of the present invention.

I. Measurement of Enzyme Inhibition.

For studying inhibition of *Plasmodium* or human DHODH enzyme, two assays that are in routine use are described, for example, in Baldwin, et al. (2002) *J Biol. Chem.*, 277, 41827-41834, and Baldwin, et al. (2005) *J. Biol. Chem.*, 280. 21847-21853.

Briefly, this colorimetric assay monitors the reduction of 2,6-dichloroindophenol (DCIP) at 600 nm (e=18.8 mM$^{-1}$ cm$^{-1}$) for measuring DHOD inhibition. The assay was carried out using a solution containing 100 mM HEPES, pH 8.0, 150 mM NaCl, 10% glycerol, 0.1% Triton X-100, 20 micro molar CoQ$_D$ (coenzyme Q$_D$), 200 micro molar L-dihydroorotate, and 120 micro molar DCIP. Reactions are initiated by addition of enzyme to a final concentration in the range of about 5 nM to about 50 nM while maintaining the temperature of a circulating water bath at 25° C.

Alternatively, for potent compounds, activity was determined by directly measuring the production of orotic acid at 296 nm (ε=4.3 mM$^{-1}$ cm$^{-1}$). Assay solutions were prepared as discussed above, except that DCIP is not present and the solution is depleted of oxygen by the inclusion of an oxidase/reductase system, such as, 0.1 mg/ml of glucose oxidase, 0.02 mg/ml catalase and 50 mM glucose. The data obtained was fitted to equation 1, to determine the IC$_{50}$ values of the representative compounds.

$$v_i = \frac{v_o}{1 + \frac{[I]}{IC_{50}}}$$ Equation 1

Table 5 shows the IC$_{50}$ and EC$_{50}$ values for an illustrative set of compounds against *Plasmodium falciparum*.

TABLE 5

| Structure | IC50 pfDHOD (μM) | EC50 Pfalciparum 3D7 (μM) |
|---|---|---|
| (tetrahydronaphthalenyl-NH-imidazotriazolopyrimidine) | 0.5 | 1.8 |
| (4-CF$_3$-phenyl-NH-imidazopyrimidine) | 0.077 | 0.33 |
| (indanyl-NH-imidazotriazolopyrimidine) | 0.5 | 2.4 |
| (4-Cl-phenyl-NH-triazolopyrimidine-CF$_3$) | 0.09 | 0.26 |
| (3,5-dimethylphenyl-NH-triazolopyrimidine-CF$_3$) | 0.22 | 0.7 |

TABLE 5-continued
| Structure | IC50 pfDHOD (μM) | EC50 Pfalciparum 3D7 (μM) |
|---|---|---|
| 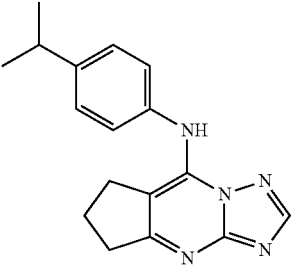 [SMILES: CC(C)c1ccc(Nc2c3c(nc4ncnn24)CCC3)cc1] | 0.25 | 1.8 |
| 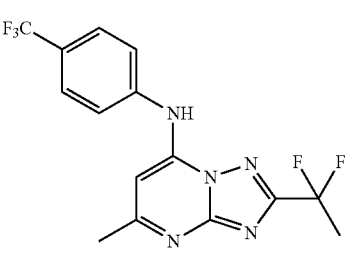 | 0.038 | 0.007 |
| 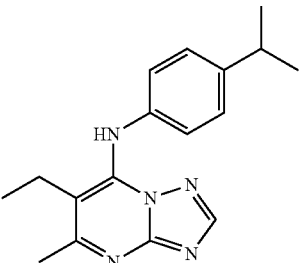 | 1.66 | >10 |
| 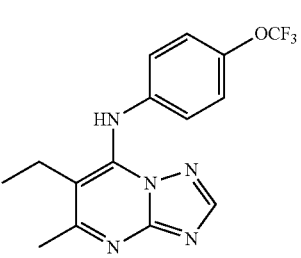 [SMILES: CCc1c(C)nc2ncnn2c1Nc1ccc(OC(F)(F)F)cc1] | 3.17 | >10 |
| 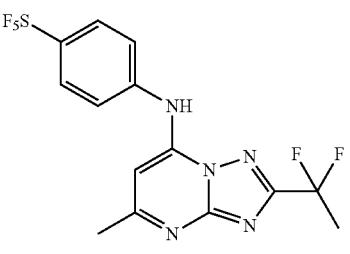 | 0.03 | 0.019 |
TABLE 5-continued
| Structure | IC50 pfDHOD (μM) | EC50 Pfalciparum 3D7 (μM) |
|---|---|---|
| 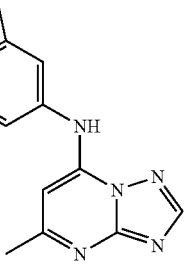 | 0.09 | 0.07 |
| 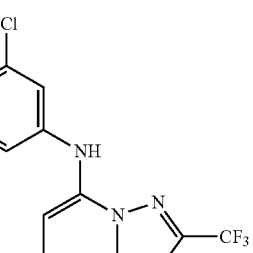 | 0.13 | 0.8 |
| 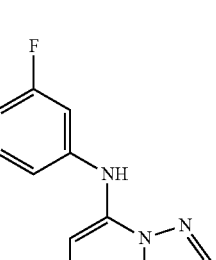 | 0.19 | 0.24 |
| 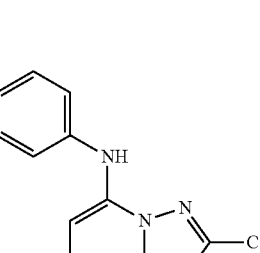 | 0.035 | 0.073 |
| 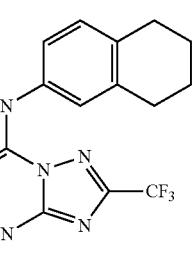 | 0.043 | |

TABLE 5-continued

| Structure | IC50 pfDHOD (μM) | EC50 Pfalciparum 3D7 (μM) |
|---|---|---|
| 3-Cl-C6H4-NH-[2-methoxy-5-methyl-[1,2,4]triazolo[1,5-a]pyrimidin-7-yl] | 0.5 | 1.0 |
| 5,6-dichloroindan-2-yl-NH-[5-methyl-[1,2,4]triazolo[1,5-a]pyrimidin-7-yl] | 1.2 | >5 |
| 4-CF3-3-F-C6H3-NH-[6-methylimidazo[1,2-a]pyrimidin-...] | 0.14 | 0.6 |
| 4-SF5-C6H4-NH-[6-methylimidazo[1,2-a]pyrimidin-...] | 0.2 | 0.6 |
| 5,6,7,8-tetrahydronaphthalen-2-yl-NH-[2-methyl-[1,2,4]triazolo[1,5-a]pyrimidin-7-yl] | 0.1 | 0.3 |
| indan-5-yl-NH-[2-methylimidazo[1,2-a]pyrimidin-...] | 0.13 | 0.6 |
| 4-(CF3CH2)-C6H4-NH-[5-methyl-[1,2,4]triazolo[1,5-a]pyrimidin-7-yl] | 2.47 | 11.0 |
| 4-Cl-3-F-C6H3-NH-[5-methyl-[1,2,4]triazolo[1,5-a]pyrimidin-7-yl] | 0.51 | 3.5 |
| 5,6-difluoroindan-2-yl-NH-[5-methyl-[1,2,4]triazolo[1,5-a]pyrimidin-7-yl] | 1.0 | 1.5 |
| 4-(CF3S)-C6H4-NH-[5-methyl-[1,2,4]triazolo[1,5-a]pyrimidin-7-yl] | 0.61 | >4.0 |
| 5-F-indan-2-yl-NH-[5-methyl-[1,2,4]triazolo[1,5-a]pyrimidin-7-yl] | 0.61 | 1.3 |

TABLE 5-continued

| Structure | IC50 pfDHOD (μM) | EC50 Pfalciparum 3D7 (μM) |
|---|---|---|
| H3CO/H3CO-indane-NH-[5-methyl-triazolopyrimidine] | 4.62 | 7.7 |
| Br-indane-NH-[5-methyl-triazolopyrimidine] | 0.99 | 6.6 |
| F5S-phenyl-NH-[5-methyl-2-CF3-triazolopyrimidine] | 0.13 | 0.14 |
| 4-F-phenyl-NH-[5-methyl-2-CF3-triazolopyrimidine] | 0.74 | 8.5 |
| 4-Br-phenyl-NH-[tetrahydro-triazoloquinazoline] | 2.12 | 9.9 |
| 4-tBu-3-F-phenyl-NH-[5-methyl-triazolopyrimidine] | 0.06 | 0.1 |
| 6-F-tetralin-NH-[5-methyl-triazolopyrimidine] | 0.63 | 2.5 |
| 3,4-bis(CF3)-phenyl-NH-[5-methyl-triazolopyrimidine] | 0.54 | 2.3 |
| 4-SF5-phenyl-NH-[2,5-dimethyl-triazolopyrimidine] | 0.51 | 0.42 |
| 4-Cl-3-F-phenyl-NH-[5-methyl-2-CF3-triazolopyrimidine] | 0.52 | 0.25 |

TABLE 5-continued

| Structure | IC50 pfDHOD (μM) | EC50 Pfalciparum 3D7 (μM) |
|---|---|---|
| (3-F-4-Me-phenyl-NH-6,7-dihydro-5H-cyclopenta[d][1,2,4]triazolo[1,5-a]pyrimidine) | 1.43 | 8.3 |
| (5,6,7,8-tetrahydronaphthalen-2-yl-NH-5-methyl-[1,2,4]triazolo[1,5-a]pyrimidine) | 0.032 | 0.2 |
| (4-CF3-phenyl-NH-5-CF3-[1,2,4]triazolo[1,5-a]pyrimidine) | 1.7 | >10 |
| (6-Cl-1,2,3,4-tetrahydronaphthalen-2-yl-NH-5-methyl-[1,2,4]triazolo[1,5-a]pyrimidine) | 0.67 | 10 |
| (1,2,3,4-tetrahydronaphthalen-2-yl-NH-5-methyl-2-CF3-[1,2,4]triazolo[1,5-a]pyrimidine) | 1.2 | |

TABLE 5-continued

| Structure | IC50 pfDHOD (μM) | EC50 Pfalciparum 3D7 (μM) |
|---|---|---|
| (3-F-4-CF3-phenyl-NH-5-methyl-2-C(CH3)F2-[1,2,4]triazolo[1,5-a]pyrimidine) | 0.035 | 0.0093 |
| (3,5-diF-4-CF3-phenyl-NH-5-methyl-2-C(CH3)F2-[1,2,4]triazolo[1,5-a]pyrimidine) | 0.020 | 0.030 |
| (4-SF5-phenyl-NH-5-methyl-2-OMe-[1,2,4]triazolo[1,5-a]pyrimidine) | 0.042 | 0.064 |
| (4-CF3-phenyl-NH-5-methyl-2-iPr-[1,2,4]triazolo[1,5-a]pyrimidine) | 0.11 | 0.098 |
| (4-CF3-phenyl-NH-5-methyl-2-C(Et)F2-[1,2,4]triazolo[1,5-a]pyrimidine) | 0.19 | 0.045 |

TABLE 5-continued

| Structure | IC50 pfDHOD (μM) | EC50 Pfalciparum 3D7 (μM) |
|---|---|---|
| F₃C-phenyl-NH-[triazolopyrimidine]-cyclopropyl | 0.14 | 0.15 |
| F₅S-phenyl-NH-[triazolopyrimidine] | 0.16 | 018 |
| F₃C,F,F-phenyl-NH-[triazolopyrimidine]-CF₃ | 0.022 | 0.0048 |
| F₅S-phenyl-NH-[triazolopyrimidine]-ethyl | 0.15 | 0.1 |
| F₅S-phenyl-NH-[triazolopyrimidine]-isopropyl | 0.1 | 0.42 |
| F₅S-phenyl-NH-[triazolopyrimidine]-CF₂-ethyl | 0.075 | 0.55 |
| F₅S-phenyl-NH-[triazolopyrimidine]-cyclopropyl | 0.093 | 0.5 |
| Cl-phenyl-NH-[triazolopyrimidine]-CHF₂ | 0.028 | 0.033 |

As shown in table 5, the compounds of the invention are potent inhibitors of the *Plasmodium falciparum* DHOD enzymes, with $IC_{50}$ values in the low to sub-micromolar range.

II. In vitro Evaluation of Compound Efficacy on the Human Malaria Parasite, *P. falciparum*.

To study inhibition of cell proliferation, $^3$H-hypoxanthine uptake is measured in drug-treated, *P. falciparum*-infected erythrocytes grown in culture, pursuant to the methodology of Desjardins, et al. (1979) *Antimicrobial Agents and Chemotherapy* 16, 710-718, and Zhang and Rathod (2002) *Science* 296, 545-547.

III. In vivo Evaluation of Compound Efficacy (A) The standard *P. berghei* mouse model for infection is utilized to evaluate the efficacy of candidate compounds, according to the invention, against parasites in vivo. See review of Fidock, et al. (2004) *Nature Rev. Drug Discovery* 3, 509-20. Compounds are dosed either orally or IP, with the exact regimens (e.g. frequency of dosing, drug concentrations at dosing) determined based on the pharmocokinetic profiles of the individual analogs. Inhibition of parasite growth is determined microscopically by staining a thin smear of blood obtained from the test animal using a Wright-Giemsa stain. Greater suppression of parasite growth is observed if drug is administered twice a day rather than a single dose. These results indicate that the compounds of the invention are potent inhibitors of PfDHODH enzyme and are candidate therapeutics for the treatment of malaria.

(B) In the event that the mouse model does not provide a positive indication for a given candidate compound, the humanized malarial mouse model is used for the testing, in accordance with Morosan, et al. (2006) *J. Infect. Dis.* 193, 996-1004. These results indicate that compounds of the invention have similar efficacy to marketed anti-malarials (e.g. chloroquine).

We claim:
1. A compound selected from:
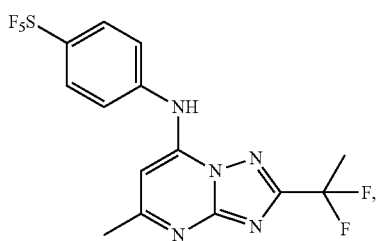
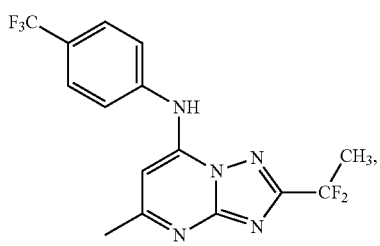
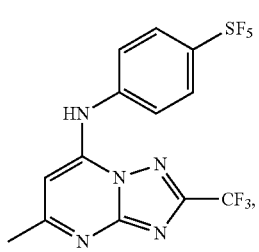
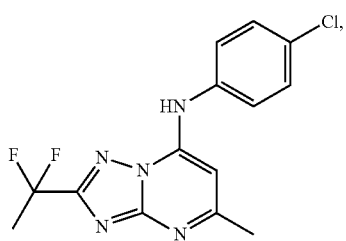
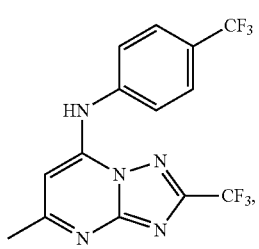
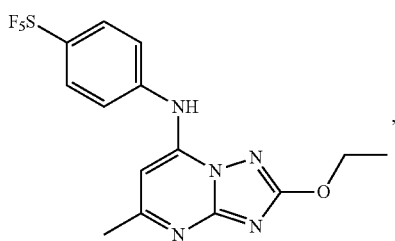
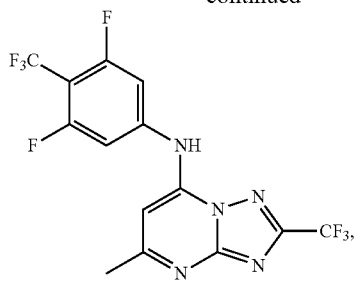
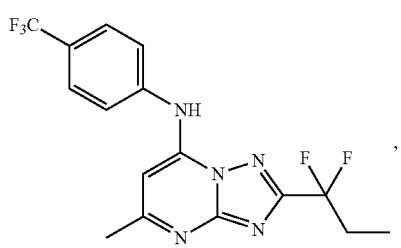
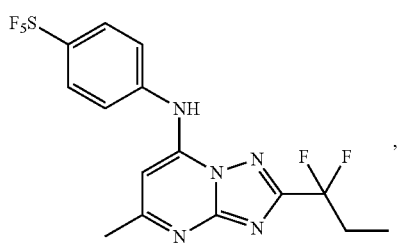
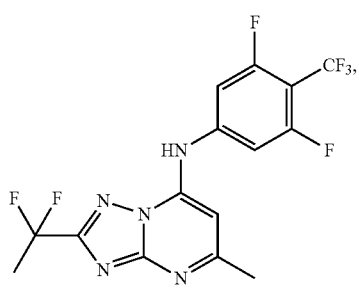
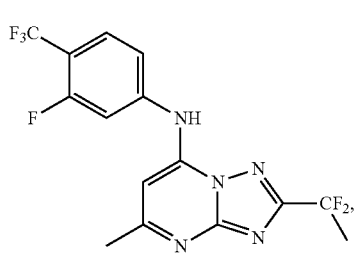
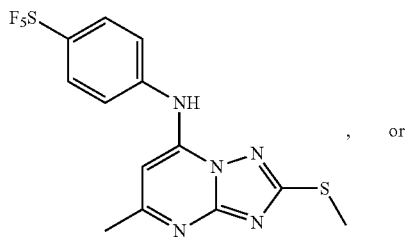, or

-continued

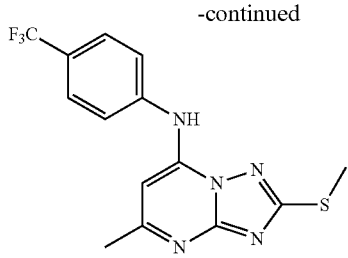

and stereoisomers, tautomers, solvates, prodrugs and pharmaceutically acceptable salts thereof.

2. The compound according to claim 1, wherein said compound has the following formula:

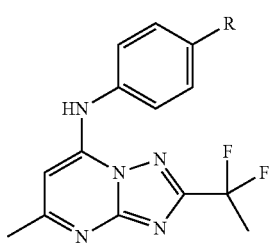

wherein R is selected from Cl, $CF_3$ or $SF_5$; and stereoisomers, tautomers, solvates, prodrugs and pharmaceutically acceptable salts thereof.

3. The compound according to claim 1 wherein said compound is

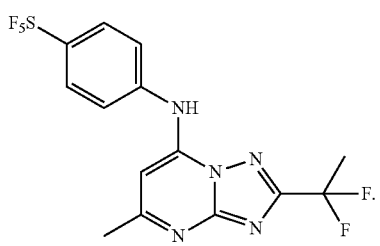

4. The compound according to claim 1, wherein the pharmaceutically acceptable salt of said compound is selected from acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, or valerate salts.

5. A pharmaceutical composition comprising a compound selected from the following group:

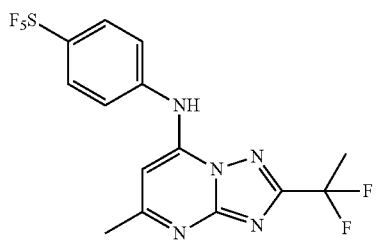

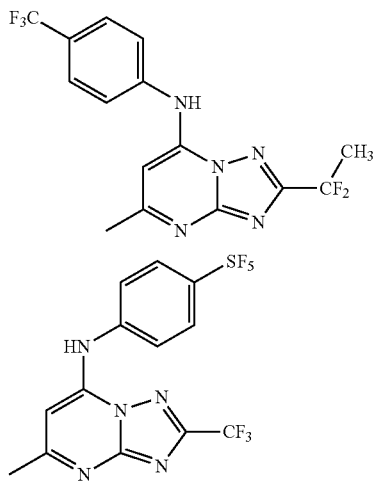

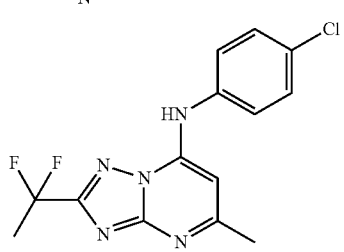

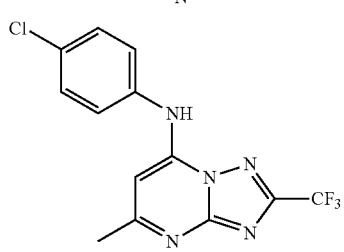

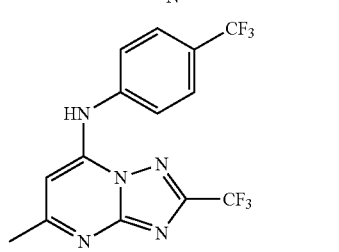

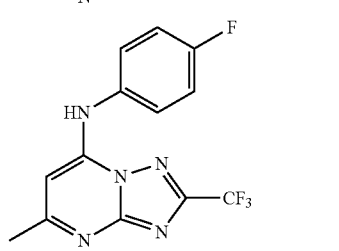

-continued

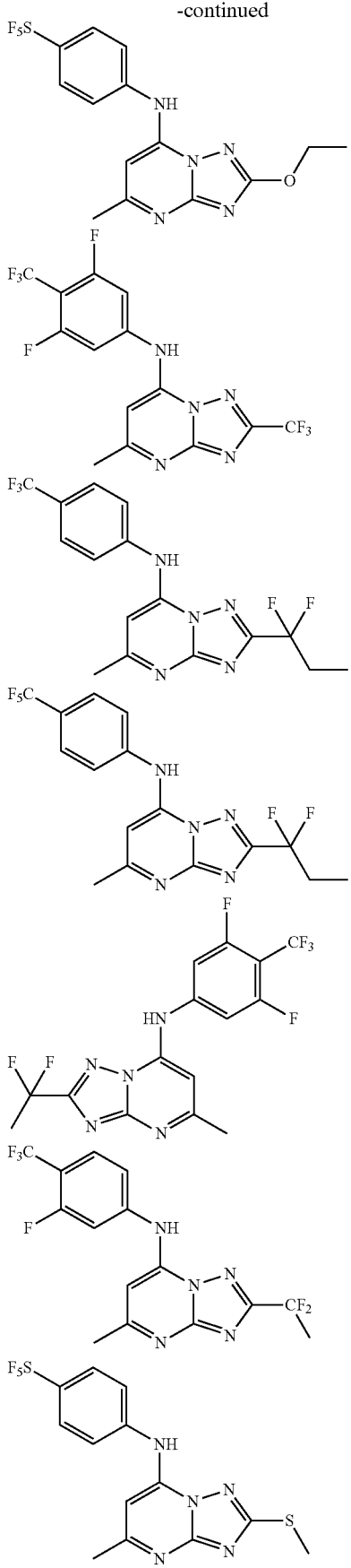

-continued

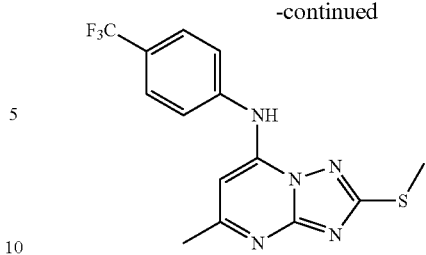

and a pharmaceutically acceptable carrier.

6. The pharmaceutical composition according to claim 5, wherein the composition is an oral formulation.

7. A method of inhibiting *Plasmodium* dihydroorotate dehydrogenase in a subject comprising the administration of a therapeutically effective amount of a compound according to claim 1 or a pharmaceutical composition thereof to a subject in need thereof.

8. The method according to claim 7, wherein the compound is administered at a daily dosage of from about 1 mg to about 50 mg per kilo body weight.

9. The method according to claim 7, wherein the compound is administered at a daily dosage of from about 5 mg to about 25 mg per kilo body weight.

10. The method according to claim 7, wherein the compound administered is:

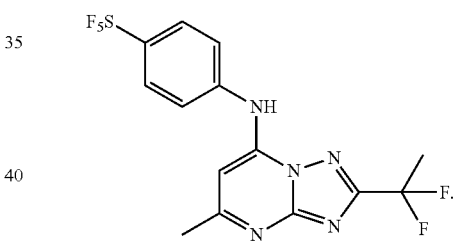

11. A method of treating a parasite infection by the inhibition of *Plasmodium* dihydroorotate dehydrogenase in a subject comprising the administration of a therapeutically effective amount of a compound according to claim 1 or a pharmaceutical composition thereof to a subject in need thereof.

12. The method according to claim 11, wherein the parasite infection is malaria.

13. The method according to claim 11, wherein the parasite infection is a *P. falciparum* infection.

14. The method according to claim 11, wherein the compound is administered at a daily dosage of from about 1 mg to about 50 mg per kilo body weight.

15. The method according to claim 11, wherein the compound is administered at a daily dosage of from about 5 mg to about 25 mg per kilo body weight.

16. The method according to claim 11, wherein the compound administered is:

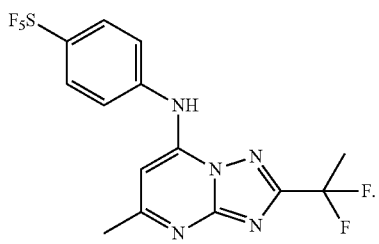

17. A pharmaceutical formulation according to claim 5 wherein the compound is of the following formula:

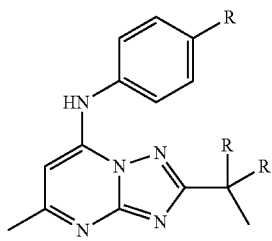

wherein R is selected from Cl, $CF_3$ and $SF_5$; and stereoisomers, tautomers, solvates, and pharmaceutically acceptable salts thereof.

18. A pharmaceutical formulation according to claim 5 wherein the compound is

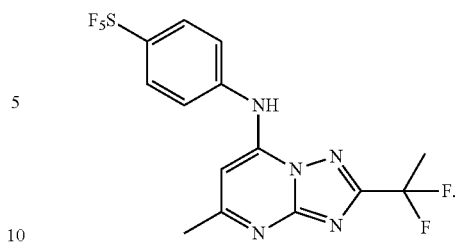

19. A pharmaceutical formulation according to claim 5 wherein the pharmaceutically acceptable salt is selected from acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts.

\* \* \* \* \*